(12) United States Patent
Therien et al.

(10) Patent No.: US 7,842,758 B2
(45) Date of Patent: Nov. 30, 2010

(54) CONJUGATED MATERIALS FEATURING PROQUINOIDAL UNITS

(75) Inventors: Michael J. Therien, Philadelphia, PA (US); Kimihiro Susumu, Washington, DC (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 96 days.

(21) Appl. No.: 12/160,265

(22) PCT Filed: Jan. 10, 2007

(86) PCT No.: PCT/US2007/000621

§ 371 (c)(1),
(2), (4) Date: Nov. 20, 2008

(87) PCT Pub. No.: WO2007/081991

PCT Pub. Date: Jul. 19, 2007

(65) Prior Publication Data

US 2009/0221762 A1    Sep. 3, 2009

Related U.S. Application Data

(60) Provisional application No. 60/757,653, filed on Jan. 10, 2006.

(51) Int. Cl.
C08C 19/20 (2006.01)
(52) U.S. Cl. ............... 525/349; 525/375; 525/389; 525/417; 525/535; 525/540; 528/377; 528/423; 540/121; 540/145; 544/234; 544/238; 548/134; 548/135
(58) Field of Classification Search ............ 525/348, 525/349, 375, 389, 417, 535, 540; 528/377, 528/423; 540/121, 145; 544/234, 238; 548/134, 548/135
See application file for complete search history.

(56) References Cited

U.S. PATENT DOCUMENTS

2005/0019265 A1    1/2005    Hammer et al.

OTHER PUBLICATIONS

Ajayaghosh, A., "Donor-acceptor type low band gap polymers: polysquaraines and related systems," Chem. Soc. Rev. 2003, 32, 181-191.
Anderson, H., "Conjugated Porphyrin Ladders," J. Inorg. Chem. 1994, 33, 972-981.
Angiolillo, P., "EPR Spectroscopy and Photophysics of the Lowest Photoactivated Triplet State of a Series of Highly Conjugated (Porphinato) Zn Arrays," J et al., J. Am. Chem. Soc. 1995, 117, 12514-12527.
Beljonne, D. et al., "Investigation of the linear and nonlinear optical response of edge-linked conjugated zinc porphyrin oligomers by optical spectroscopy and configuration interaction techniques," J. Chem. Phys. 1997, 106, 9439-9460.
Brabec, C.J. et al., "Plastic Solar Cells," Adv. Funct. Mater. 2001,11,15-261.
Bredas, J. L. et al., "Towards organic polymers with very small intrinsic band gaps. I. Electronic structure of polysothianaphthene and derivatives," .J. Chem. Phys. 1986, 85, 4673-4678.
Chen, M et al.,. "1micorn wavelength photo- and electroluminescence from a conjugated polymer," Appl. Phys. Lett. 2004, 84, 3570-3572.
Frolov, S. V. et al., "Exciton Dynamics in soluble Poly(p-phenylenevinylene): Towards an Ultrafast Excitonic Switch," Phys. Rev. Lett. 1997, 78, 4285-4288.
Gouterman, M., "Optical Spectra and Electronic Structure of Porphyrins and Related Rings," In The Porphyrins; Dolphin, D., Ed.; Academic Press: London, 1978; vol. III, p. 1-165.
Jenekhe, S. A., "A class of narrow-band-gap semiconducting polymers," Nature 1986, 322, 345-347.
Jiang, X. M. et al., "Spectroscopic Studies of Photoexcitations in Regioregular and Regiorandom Polythiophene Films," Adv. Funct. Mater. 2002, 12, 587-597.

(Continued)

*Primary Examiner*—David Wu
*Assistant Examiner*—Robert Jones, Jr.
(74) *Attorney, Agent, or Firm*—Woodcock Washburn, LLP

(57) ABSTRACT

The invention concerns compounds, oligomers, and polymers that contain: (I), (II), (III), or (IV) groups; where "-" indicates points of attachment.

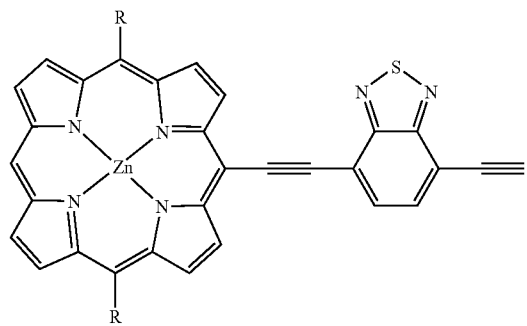

PZnE-BTD-EPZn

-continued
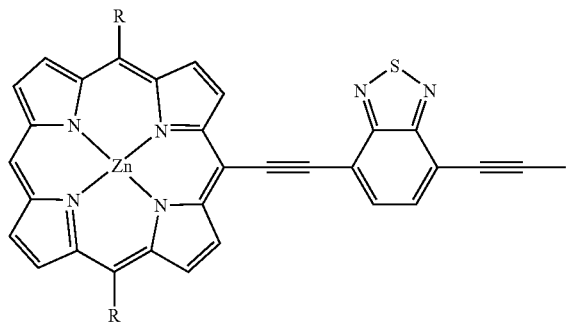
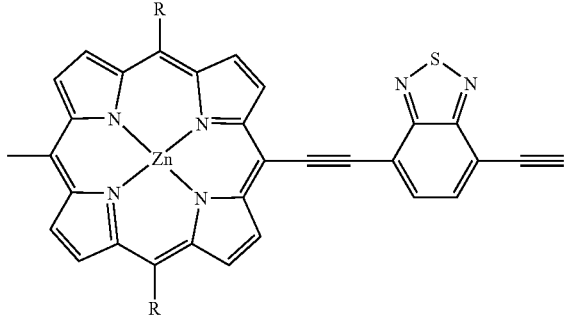
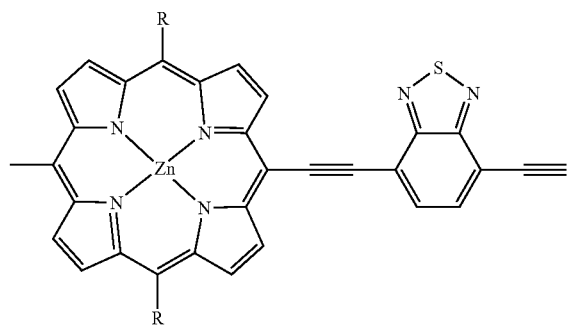
PZnE-BTD-EPZnE-BTD-EPZn
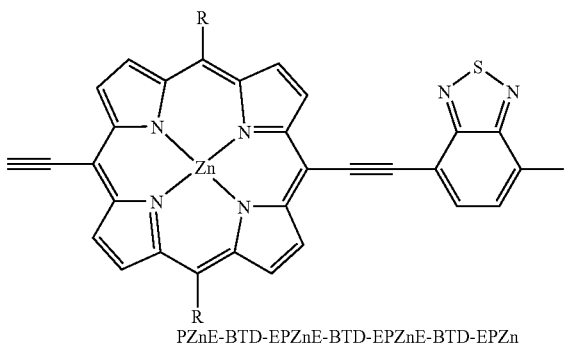
PZnE-BTD-EPZnE-BTD-EPZnE-BTD-EPZn
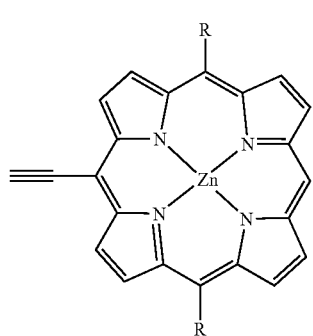
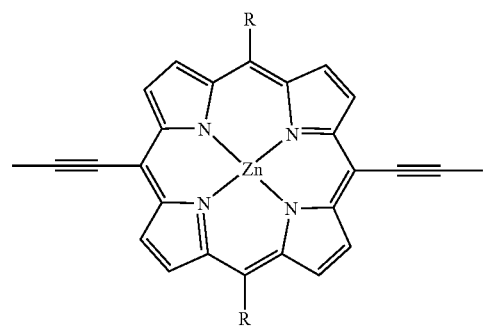
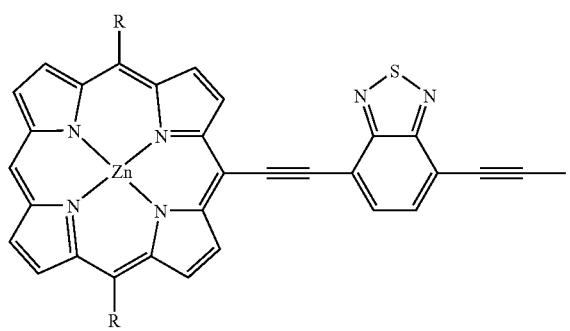
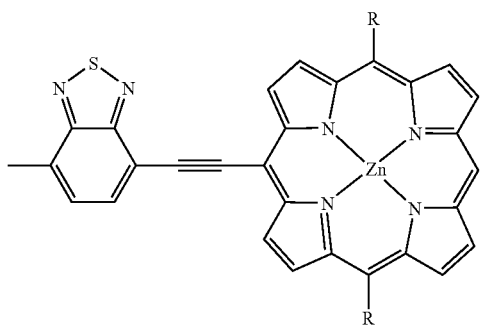

-continued
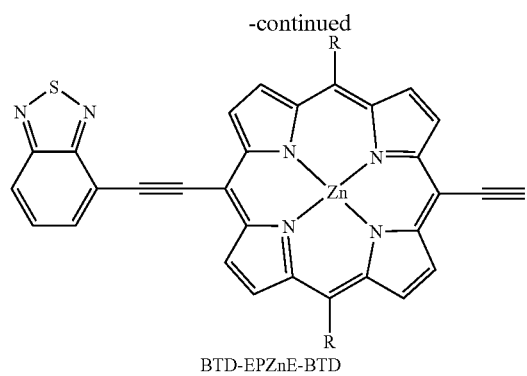
BTD-EPZnE-BTD
-continued
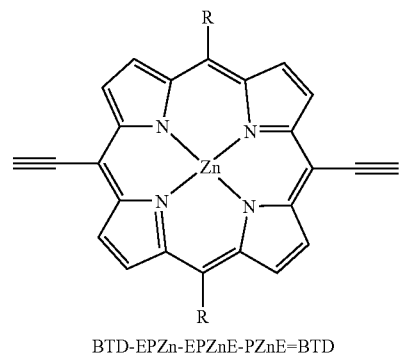
BTD-EPZn-EPZnE-PZnE=BTD
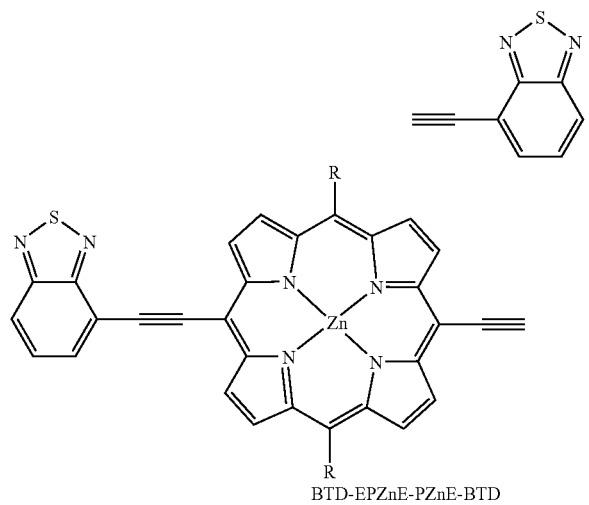
BTD-EPZnE-PZnE-BTD
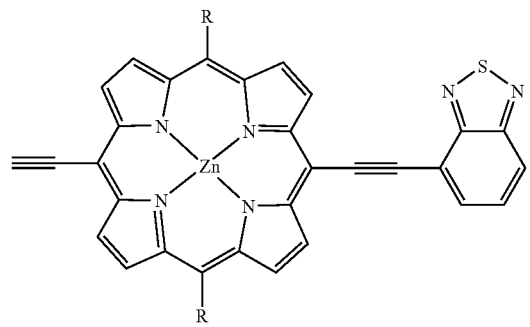
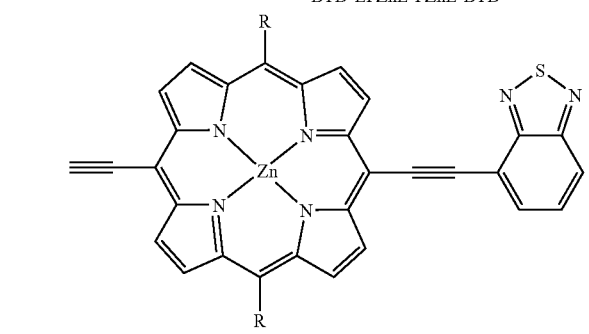
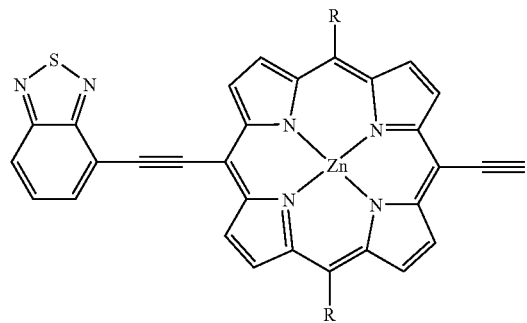
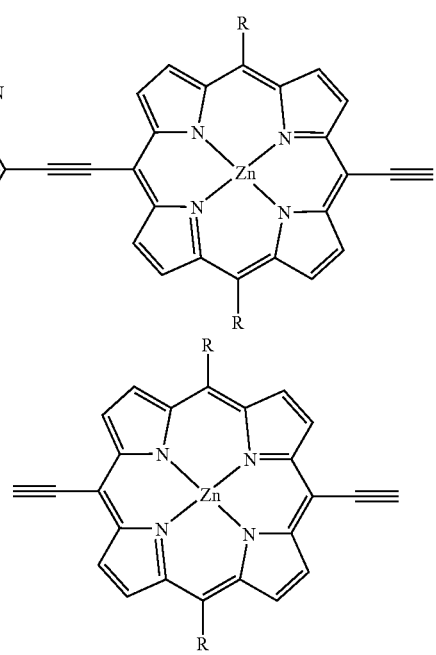
BTD-EPZn-EPZnE-PZn-EPZnE-PZnE-BTD -continued
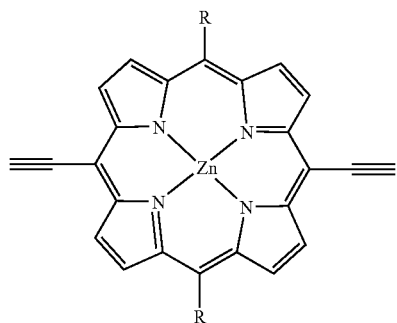
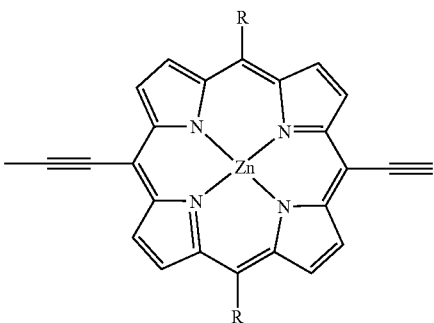
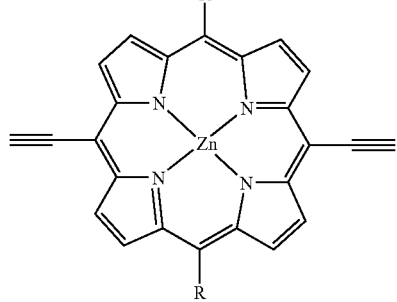
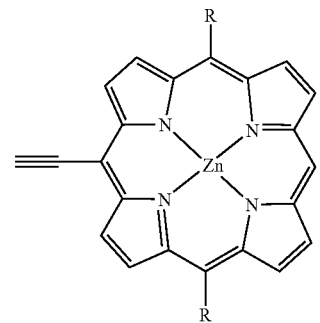
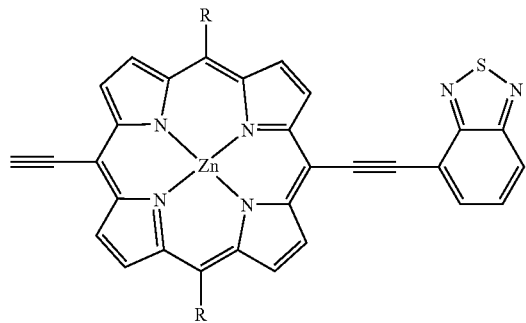
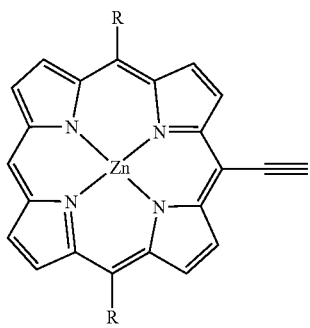
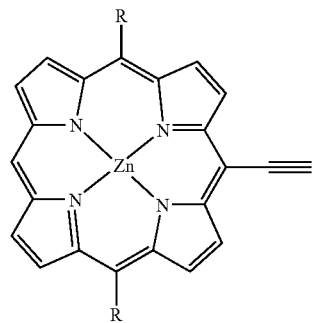
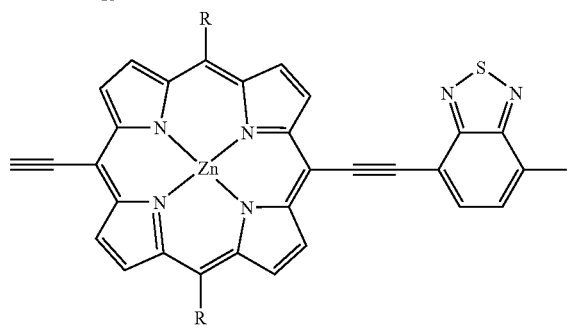
PZn-EPZnE-BTD-EPZnE-PZnE-BTD-EPZnE-PZn
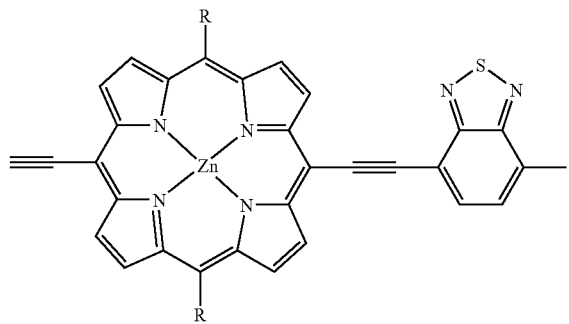
PZn-EPZnE-BTD-EPZnE-PZnE
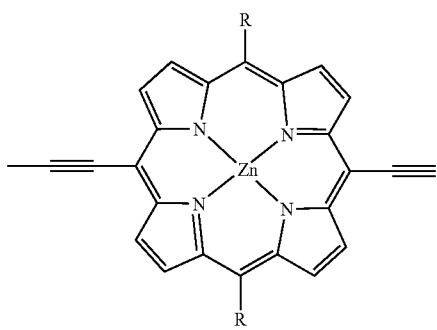

-continued
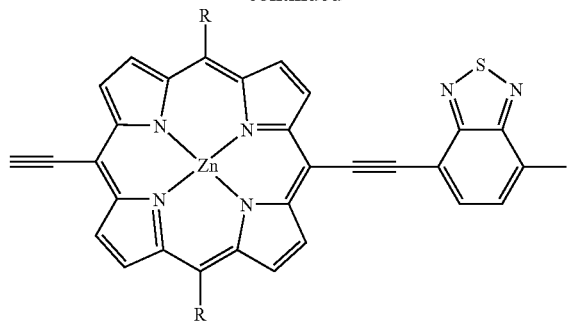
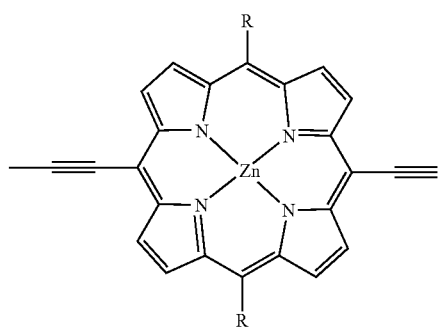
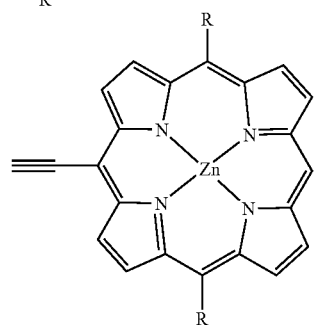
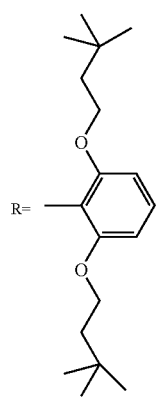
(I)
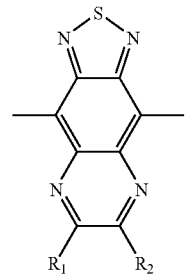
(II)
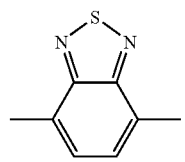
(III)
(IV)
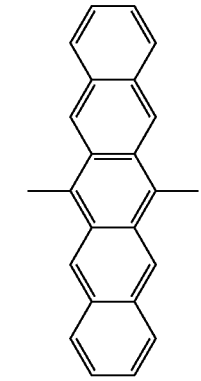
groups;
29 Claims, 14 Drawing Sheets

OTHER PUBLICATIONS

Karikomi, M. et al., "New Narrow-Bandgap Polymer Composed of Benzobis (1,2,5-thiadiazole) and Thiophenes," J. Am. Chem. Soc. 1995, 117, 6791-6792.

Kasha, M. et al., "The Exciton Model in Molecular Spectroscopy," Pure AppL Chem. 1965, 11, 371-392.

Katz, H. E et al., "Synthetic Chemistry for Ultrapure, Processable, and High-Mobility Organic Transistor Semiconductors," Ace. Chem. Res. 2001, 34, 359-369.

Katz, H. E., "Organic Molecular Solids as Thin Film Transistor Semiconductors," J. Mater. Chem. 1997, 7, 369-376.

Kitamura, C. et al., "Design of Narrow-Bandgap Polymers. Syntheses and Properties of Monomers and Polymers Containing Aromatic-Donor and o-Quinoid-Acceptor Units ," Chem. Mater. 1996, 8, 570-578.

Kobayashi, M. et al.,. "The Electronic and Electrochemical Properties of Poly(isothianapthene)," J. Chem. Phys. 1985, 82, 5717-5723.

Kraabel, B, "Subpicosecond study of excitons in a phenylenevinylene conjugated polymer: exciton-exciton interactions and infrared photoinduced absorption features," Chem. Phys. Lett. 2000, 330, 403-409.

Kraabel, B. et al., "Unified picture of the photoexcitations in phenylene-based conjugated polymers: Universal spectral and dynamical features in subpicosecond transient absorption," Phys. Rev. B 2000, 61, 8501-8515.

Kumble, R. et al., "Ultrafast Dynamics of Highly Conjugated Porphyrin Arrays," J.. Am. Chem. Soc. 1998, 120, 11489-11498.

Lanzani, G. et al., "Visible and near-infrared ultrafast optical dynamics of hexamethylsexithiophene in solution," Phys. Rev. B 1996, 53, 4453-4457.

LeCours, S. M. et al.,. "Exceptional Electronic Modulation of Porphyrins through meso-Arylethynyl Groups. Electronic Spectroscopy, Electronic Structure, and Electrochemistry of [5,15-Bis[(aryl)ethynyl]-10,20-diphenylporphinato]zinc(II) Complexes. X-ray Crystal Structuress of [5,15- Bis[4'-fluorophenyl)ethynyl]-10,20-diphenylporphinato]sinc(II) and 5,15- Bis[(4'-methoxyphenyl)ethynyl]-10,20-diphenylporphyrin," J. Am. Chem. Soc. 1996, 118, 11854-11864.

Lee, Y.-S. et al. "The effect of heteroatomic substitutions on the band gap of polyacetylene and polyparaphenylene derivatives," J. Chem. Plays. 1988, 88, 2609-2617.

Lin, V. S.-Y. et al., "Highly Conjugated, Acetylenyl Bridged Porphyrins: New Models for Light-Harvesting Antenna Systems," Science 1994, 264, 1105-1111.

Lin, V. S.-Y. et al., "The Role of Porphyrin-to-Porphyrin Linkage Topology in the Extensive Modulation of the Absorptive and Emissive Properties of a Series of Ethynyl-and Butadiynyl-Bridged Bis- and Tris(porphinato) zinc Chomophores," Chem. Eur. J. 1995, 1, 645-651.

Martin, R. E. et al., "Linear Monodisperse pi-conjugated oligomers," Angew. Chem. Int. Ed. 1999, 38, 1350-1377.

Mitschke, U.; Bauerle, "The electroluminescence of organic materials," P. J. Mater. Chem. 2000, 10, 1471-1507.

Moraes, F. et al., "Photoexcitations in poly(thiophene): Photoinduced infrared absorption and photoinduced electron-spin resonance," Phys. Rev. B 1984, 30, 2948-2950.

Nalwa, H. S., "Organic Materials for Third-Order Nonlinear Optics," Adv. Mater. 1993, 5, 341-358.

O'Keefe, G. E. et al., "Femtosecond transient photoinduced transmission measurements on a novel conjugated zinc porphyrin system," J. Chem. Phys. 1996, 104, 805-811.

Ono, C. et al., "Benzobis(thiadiazole)s Containing Hypervalent Sulfur Atoms: Novel Heterocycles with High Electron Affinity and Short Intermolecular Contacts between Heteroatoms," Angew. Chem. Int. Ed. Engl. 1994, 33, 1977-1979.

Pilgram, K. et al., "Bromination of 2,1,3-Benzothiadiazoles," J. Heterocycl. Chem. 1970, 7, 629-633.

Quimby, D.J. et al., "Luminescence studies on several tetraarylprophins and their zinc derivatives," J. Am. Chem. Soc., 1975, 97, 5111-5117.

Roncali, I. "Synthetic Principles for Bandgap Control in Linear Conjugated Systems," Chem. Rev. 1997, 97,173-205.

Rubtsov, I. V. et al., "Ultrafast Singlet Excited-State Polarization in Electronically Asymmetric Ethyne-Bridged Bis[9porphinato)Zinc(II)] Complexes," J. Am. Chem. Soc. 2003, 125, 2687-2696.

Salzner, U., "Does the Donor-Acceptor Concept Work for Designing Synthetic Metals?.1. Theoretical Investigation of Poly(3-Cyano-3'-hydroxybithiophene)," Plays. Chem. B, 2002, 106, 9214-9220.

Segura, J L..., "The Chemistry of Electroluminescent Organic Materials," Acta Polym. 1998, 49, 319-344.

Shediac, R. et al., "Singlet and Triplet Excited States of Emissive, Conjugated Bis(porphyrin) Compounds Probed by Optical and EPR Spectroscopic Methods," J. Am. Chem. Soc. 2000, 122, 7017-7033.

Sonmez, G et al., "Very Stable Low Band Gap Polymer for Charge Storage Purposes and Near-Infrared Applications," Chem. Mater. 2003,15,4923-4929.

Strickler, S.J. et al.," Relationship between Absorption Intensity and Fluorescence Lifetime of Molecules," J. Chem. Phys., 1962, 37, 814-820.

Susumu et al., in "Potentiometric, Electronic Structural, and Ground -and Excited-State Optical Properties of Conjugated Bis[(Porphinato)zinc(II)] Compounds Featuring Proquinoidal Spacer Units," J. Am. Chem. Soc., 2005, 127(14), 5186-5195.

Susumu, K et al.,"Decoupling Optical and Potentiometric Band Gaps in Pi-Conjugated Materials," J. Am. Chem. Soc. 2002,124, 8550-8552.

Susumu, K. et al., "Theoretical Approach to the design of Supramolecular conjugated porphyrin polymers," J. Mater. Chem. 2001, 11, 2262-2270.

Tour, J. M., "Conjugated Macromolecules of Precise Length and Constitution. Organic Synthesis for the Construction of Nanoarchitectures," Chem. Rev., 1996, 96, 537-553.

Tykwinski, R. R. et al., "Structure-Property Relationships in Third-Order Nonlinear Optical Chromophores," J. Phys. Chem. 1998, 102, 4451.

Uyeda, H. T, "Design, Synthesis, and Optoelectronic Properties of Strongly Coupled Porphyrin Based Donor-Acceptor Systems," Doctoral Dissertation, University of Pennsylvania, Philadelphia, 20021.

Uyeda, H. T. et al., "Unusual Frequency Dispersion Effects of the Nonlinear Optical Response in Highly Cojugated (Polypyridyl)metal-(Porphinato)zinc(II) Chromophores," J. Am. Chem. Soc. 2002, 124, 13806-13813.

van Mullekom, H. A. M. et al., "Developments in the chemistry and band gap engineering of donor-acceptor substituted conjugated polymers," Mater. Sci. Eng. 2001, 32, 1-40.

van Mullekorn, H. A. M. et al, "Band-gap engineering of donor-acceptor-substituted pi-conjugated polymers," Chem. Eur. J. 1998, 4, 1235-1243.

Woo, H.S. et al., "Photoinduced absorption and photoluminescence in poly(2,5-dimethoxy-p-phenylene vinylene)," Phys. Rev. B 1992, 46, 7379-7389.

Yamashita, Y. et al., "Synthesis and Properties of Benzobis(thiadiazole)s with Nonclassical pi-Electron Ring Systems," Tetrahedron:1997, 53, 10169-10178.

Yu, G, et al., "Polymer Photovoltaic Cells: Enhanced Efficiencies via a Network of Internal Donor-Acceptor Heterojunctions," Science 1995, 270, 1789-1790.

CONJUGATED MATERIALS FEATURING PROQUINOIDAL UNITS

RELATED APPLICATIONS

This application is the National Stage of International Application No. PCT/US2007/000621, filed Jan. 10, 2007, which claims benefit to U.S. Provisional Application No. 60/757,653, filed Jan. 10, 2006, the disclosure of which is incorporated herein by reference in its entirety.

GOVERNMENT RIGHTS

This invention was made with government support under a grant through the National Cancer Institute (NO1-CO-29008) and the MRSEC Program of the National Science Foundation (DMR00-79909). The government has certain rights in the invention.

FIELD OF THE INVENTION

The present invention concerns novel conjugated materials, multi[(porphinato)metal] compounds having proquinoidal spacer units, polymersomes containing such compounds, and methods of use of such compositions.

BACKGROUND OF THE INVENTION

Organic π-conjugated oligomers and polymers constitute a class of promising semiconducting materials having demonstrated utility in device applications ranging from light-emitting diodes [Segura, J. L. *Acta Polym.* 1998, 49, 319-344; Mitschke, U.; Bäuerle, P. *J. Mater. Chem.* 2000, 10, 1471-1507]; photovoltaic cells [Yu, G.; Gao, J.; Hummelen, J. C; Wudl. F.; Heeger, A. J. *Science* 1995, 270, 1789-1791; Brabec, C. J.; Sariciftci, N. S.; Hummelen, J. C. *Adv. Funct. Mater.* 2001, 11, 15-26], field-effect transistors [Katz, H. E. *J. Mater. Chem.* 1997, 7, 369-376; Katz, H. E.; Bao, Z.; Gilat, S. L. *Acc. Chem. Res.* 2001, 34, 359-369] to nonlinear optics [Nalwa, H. S. *Adv. Mater.* 1993, 5, 341-358; Tykwinski, R. R.; Gubler, U.; Martin, R. E.; Diederich, F.; Bosshard, C; Günter, P. *J. Phys. Chem. B* 1998, 102, 4451-4465]. Reducing and tuning energy gaps between the highest occupied molecular orbital (HOMO) and the lowest unoccupied molecular orbital (LUMO) of such π-conjugated species play crucial roles in optimizing the performance of electronic and optical devices based on active organic components [Tour, J. M. *Chem. Rev.* 1996, 96, 537-553; Roncali, *J. Chem. Rev.* 1997, 97, 173-205; van Mullekom, H. A. M.; Vekemans, J. A. J. M.; Meijer, E. W. *Chem. Eur. J.* 1998, 4, 1235-1243; Martin, R. E.; Diederich, F. *Angew. Chem. Int. Ed.* 1999, 38, 1350-1377; van Mullekom, H. A. M.; Vekemans, J. A. J. M.; Having a, E. E.; Meijer, E. W. *Mater. Sci. Eng.* 2001, 32, 1-40; Ajayaghosh, A. *Chem. Soc. Rev.* 2003, 32, 181-191; Sonmez, G.; Meng, H.; Wudl, F. *Chem. Mater.* 2003, 15, 4923-4929; Chen, M.; Perzon, E.; Andersson, M. R.; Marcinkevicius, S.; Jönsson, S. K. M.; Fahlman, M.; Berggren, M. *Appl. Phys. Lett.* 2004, 84, 3570-3572].

Porphyrins are tetrapyrrolic conjugated macrocyclic systems that possess modest potentiometrically determined HOMO-LUMO gaps ($E_p$; $E_{1/2}^{0/+}$-$E_{1/2}^{-/0}$) relative to those of the common monomeric aromatic building blocks used to construct traditional electronic polymers. The electronic properties of (porphinato)metal compounds can be modulated extensively by variation of the macrocycle peripheral meso- or β-substituents, as well as by selection of the central metal ion; further, a variety of modes of porphyrinoid-porphyrinoid connectivity provides sufficiently strong interchromophore electronic interactions to facilitate extensive electronic derealization. Of these families of multipigment ensembles that feature substantial ground- and excited-state interchromophore electronic interactions, those that feature direct ethyne-, butadiyne-, and oligoyne-based macrocycle-to-macrocycle connectivity have evinced a wide range of particularly impressive electrooptic properties. As increasing conjugation length diminishes significantly optical ($E_{op}$) and potentiometric ($E_p$) band gaps within these families of structures, multiporphyrin compounds that exploit cylindrically π-symmetric linkers define a point of reference from which to engineer further electronic modulation of conjugated organic materials.

An established means to further reduce the $E_{op}$ and $E_p$ gaps of π-conjugated materials involves introducing quinoid-like character into the conjugation main-chain [Roncali, J. *Chem. Rev.* 1997, 97, 173-205; van Mullekom, H. A. M.; Vekemans, J. A. J. M.; Having a, E. E.; Meijer, E. W. *Mater. Sci. Eng.* 2001, 32, 1-40; Ajayaghosh, A. *Chem. Soc. Rev.* 2003, 32, 181-191]. Solution-phase spectroscopic experiments [Lin, V. S.-Y.; DiMagno, S. G.; Therien, M. J. *Science* 1994, 264, 1105-1111; Lin, V. S.-Y.; Therien, M. J. *Chem. Eur. J.* 1995, 1, 645-651; Susumu, K.; Therien, M. J. *J. Am. Chem. Soc.* 2002, 124, 8550-8552; LeCours, S. M.; DiMagno, S. G.; Therien, M. J. *J. Am. Chem. Soc.* 1996, 118, 11854-11864] and X-ray crystallographic data [Uyeda, H. T. Doctoral Dissertation, University of Pennsylvania, Philadelphia, 2002] obtained for bis[(5,5',-10,20-di(aryl)porphinato)zinc(II)] ethyne compounds demonstrate that the bridging ethyne possesses conventional triple bond character in the ground state; electronic absorption [Lin, V. S.-Y.; DiMagno, S. G.; Therien, M. J. *Science* 1994, 264, 1105-1111; Lin, V. S.-Y.; Therien, M. J. *Chem. Eur. J.* 1995, 1, 645-651, Shediac, R.; Gray, M. H. B.; Uyeda, H. T.; Johnson, R. C; Hupp, J. T.; Angiolillo, P. J.; Therien, M. J. *J. Am. Chem. Soc.* 2000, 122, 7017-7033; Susumu, K.; Therien, M. I. *J. Am. Chem. Soc.* 2002, 124, 8550-8552], electroabsorption [Shediac, R.; Gray, M. H. B.; Uyeda, H. T.; Johnson, R. C; Hupp, J. T.; Angiolillo, P. J.; Therien, M. J. *J. Am. Chem. Soc.* 2000, 122, 7017-7033] and pump-probe spectroscopic methods [Kumble, R.; Palese, S.; Lin, V. S.-Y.; Therien, M. J.; Hochstrasser, R. M. *J. Am. Chem. Soc.* 1998, 120, 11489-11498; Rubtsov, I. V.; Susumu, K.; Rubtsov, G. I.; Therien, M. J. *J. Am. Chem. Soc.* 2003, 125, 2687-2696] are consistent with an excited state electronic structure for this species that features a modest degree of cumulenic (quinoidal) character. Porphyrin-to-porphyrin bridging motifs involving ethynes and spacers that induce a quinoidal structural perturbation with appropriately positioned frontier orbital energy levels, should enhance ground- and excited-state π-conjugation, and effect further reduction in $E_{op}$ and $E_p$ in the corresponding oligomeric and polymeric structures Polymer band-gap reduction through augmentation of π-backbone quinoidal character has been explored both experimentally [Kobayashi, M.; Colaneri, N.; Boysel, M.; Wudl, F.; Heeger, A. J. *J. Chem. Phys.* 1985, 82, 5717-5723; Jenekhe, S. A. *Nature* 1986, 322, 345-347] and theoretically [Brédas, J. L.; Heeger, A. J.; Wudl, F. *J. Chem. Phys.* 1986, 85, 4673-4678; Lee, Y.-S.; Kertesz, M. *J. Chem. Phys.* 1988, 88, 2609-2617]. In this regard, benzo[1,2-c:4,5-c']bis([1,2,5] thiadiazole) (BBTD), exemplifies an established conjugated unit with suitable electronic structure to induce substantial quinoidal character in a conjugated backbone [Ono, K.; Tanaka, S.; Yamashita, Y. *Angew. Chem. Int. Ed. Engl.* 1994, 33, 1977-1979; Karikomi, M.; Kitamura, C.; Tanaka, S.; Yamashita, Y. *J. Am. Chem. Soc.* 1995, 117, 6791-6792; Kitamura, C; Tanaka, S.; Yamashita, Y. *Chem. Mater.* 1996, 8, 570-578; Yamashita, Y.; Ono, K.; Tomura, M.; Tanaka, S. *Tetrahedron* 1991, 53, 10169-10178].

Near infrared emissive fluorophores (NIRFs) have found many uses, including optical imaging. As their utilization increases, new NIRFs are needed.

SUMMARY OF THE INVENTION

In some aspects, the invention concerns compositions that contain:
PM-(Sp-PQ-Sp-PM)$_n$, PQ-(Sp-PQ)$_n$, PQ-(Sp-PQ-Sp'-PQ')$_n$, PQ-(Sp'-PQ'-Sp-PQ)$_n$, PQ-(Sp-PQ-X)$_n$, X-Sp-PQ-(Sp-PQ-X)$_n$, PQ-(Sp-PQ-Sp'-PQ'-X)$_n$, X-Sp-PQ-(Sp-PQ-Sp'-PQ'-X)$_n$, PQ'-(Sp'-PQ'-Sp-PQ-X)$_n$, X-Sp'-PQ'-(Sp'-PQ'-Sp-PQ-X)$_n$, X-Sp-PQ-(Sp-PQ-X)$_n$, X-Sp-PQ-(Sp'-PQ'-Sp-PQ-X)$_n$, or X-(Sp-PQ-X-Sp'-PQ'-X)$_n$
wherein:
n is 1 or 2;
PM is a (porphinato)(metal) moiety;
Sp is ethynyl;
PQ is

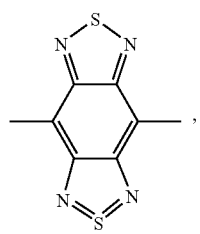 , 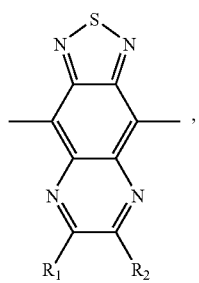 ,

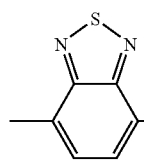 , or 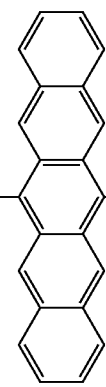 ;

where "-" indicates points of attachment;
R$_1$ and R$_2$ are H, C$_1$-C$_{12}$ alkyl, alkoxy, aryl, or glycol; and
n is an integer greater than or equal to 1;
Sp' is ethenyl, ethynyl,

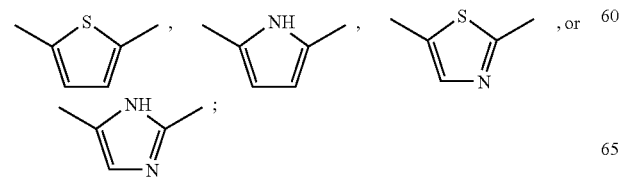 ;

PQ' is

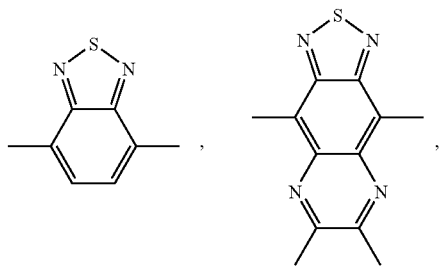

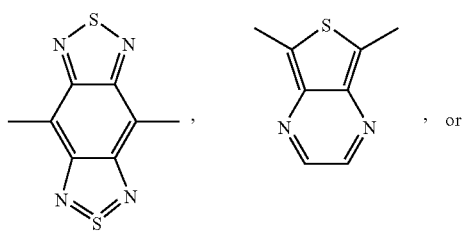 , or

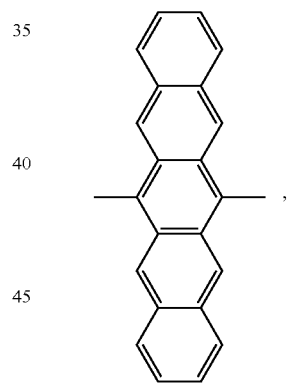

where "-" indicates points of attachment; and
X is a conjugated structure;
wherein at least one of PQ and PQ' are

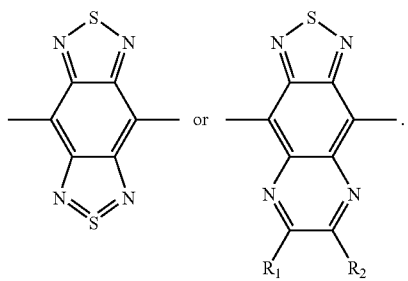

In some embodiments, the composition is a compound, oligomer or polymer.

In some embodiments, PQ is

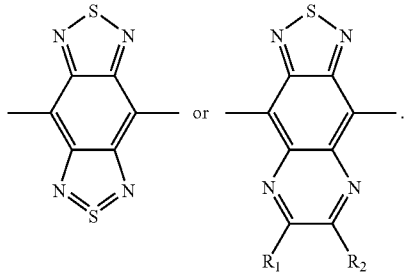

In some embodiments, n is 1 or 2.

In certain embodiments, PM is ethynyl-10-20-bis(2',6'-bis(3,3-dimethyl)-butoxy)phenyl]porphinato)zinc(II). In some embodiments, PM is a (porphinato)metal compound where the metal is Zn, Mg, Si, Sc, Ti, V, Cr, Fe, Co, Ni, Cu, Zr, Nb, Mo, Ru, Rho, Pd, As, Cd, Ge, Sn, Hf, Ta, W, Re, Os, Ir, Pt, Au, Pb.

In some embodiments, the invention concerns compound of the formula:

PM-(Sp-PQ-Sp-PM)$_n$ wherein:

PM is a (porphinato)zinc(II) moiety;

Sp is an unsaturated spacing group (such as ethenyl or ethynyl), and

PQ is

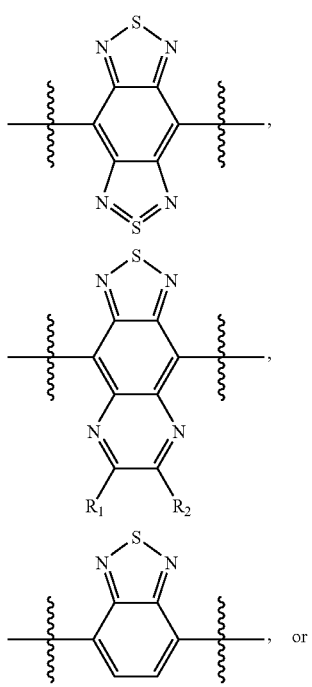

-continued

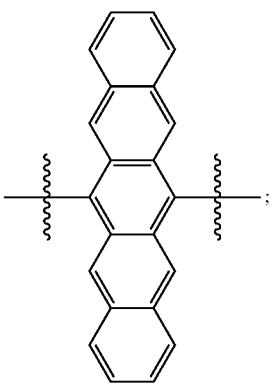

$R_1$ and $R_2$ are H, $C_1$-$C_{12}$ alkyl, alkoxy, aryl, or glycol; and n is an integer greater than or equal to 1.

In some embodiments, $R_1$ and $R_2$ are each, independently, $C_1$-$C_3$ alkyl. In certain of these embodiments, $R_1$ and $R_2$ are each methyl.

In some compounds of the invention, PM-Sp is [(10,20-bis[2',6'-bis(3,3-dimethyl-1-butyloxy)phenyl]porphinato)zinc (II)-5-ylethynyl.

In some compounds of the invention, PM-Sp is [(10,20-bis [aryl]porphinato)metal-5-ylethynyl.

In some compounds of the invention, PM-Sp is [(10,20-bis [alkyl]porphinato)metal-5-ylethynyl.

In some compounds of the invention, PM-Sp is [(10,20-bis [alkoxy]porphinato)metal-5-ylethynyl In some compounds of the invention, PM-Sp is a [(10,20-bis[alky]porphinato)metal-5-ylethynyl, [(10,20-bis[alkoxy] porphinato)metal-5-ylethynyl, or [(10,20-bis[aryl]porphinato)metal-5-ylethynyl compound that bears net charge.

In some compounds of the invention, PM-Sp is a (porphinato)metal-ylethynyl, compound.

As used herein, "PM" and "PZn" are sometimes used interchangeably. PZn refers to the moiety with zinc metal but it should be understood that other suitable metals can be used in place of zinc.

In other aspects, the invention concerns compounds, oligomers, and polymers of the formula:

PQ-(Sp-PQ)$_n$ wherein:

Sp-Q is:

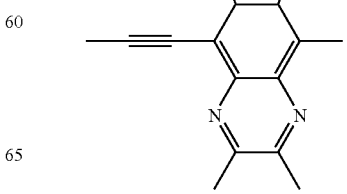

-continued
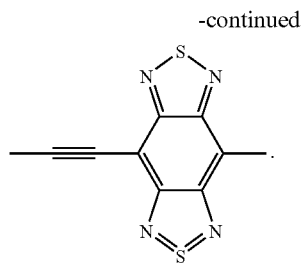
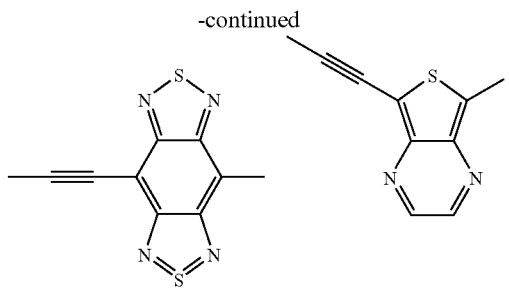
In other aspects, the invention concerns compounds, oligomers, and polymers of the formula:
PQ-(Sp-PQ-Sp'-PQ')$_n$ or PQ-(Sp'-PQ'-Sp-PQ)$_n$
wherein:
Sp-PQ is:
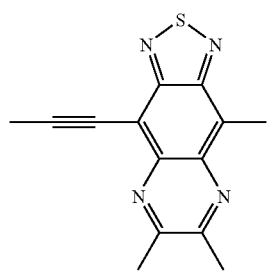
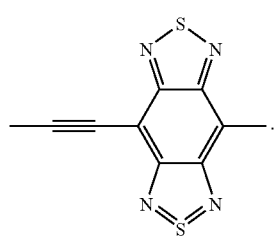
and Sp'-PQ' is selected from:
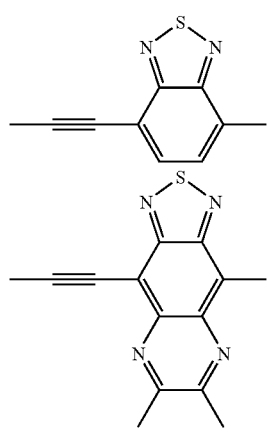
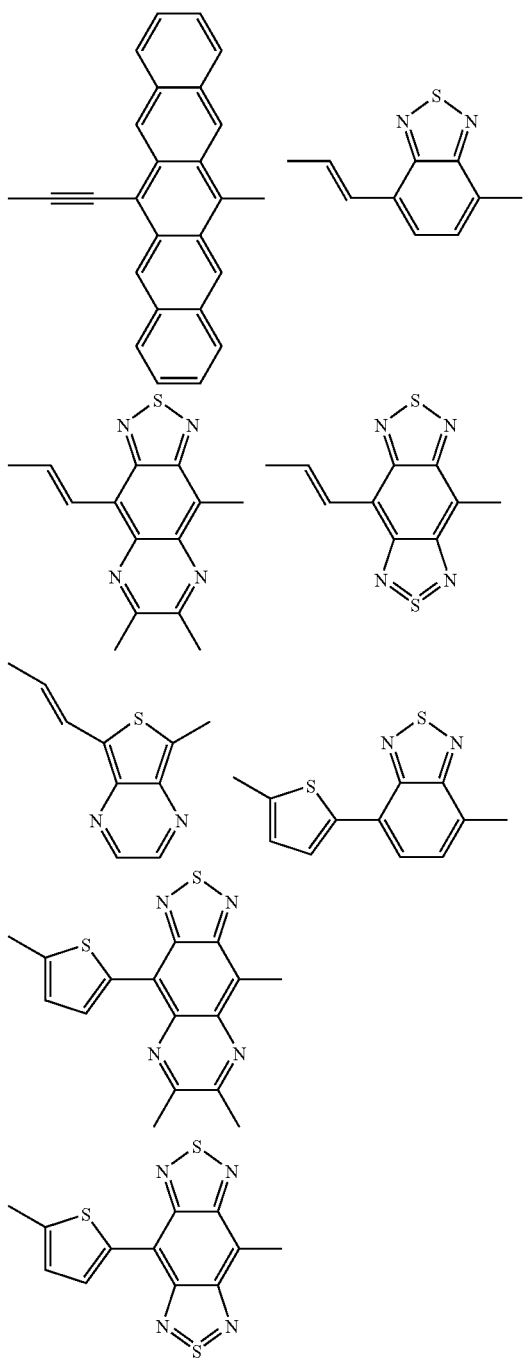

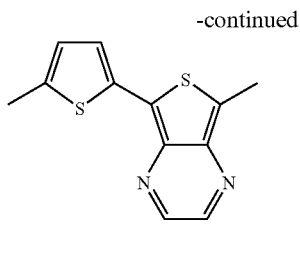

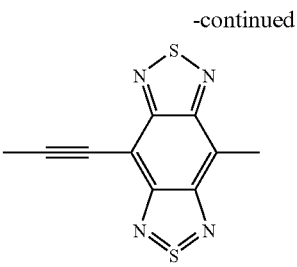

and X is a conjugated structure such as:

a porphycene, porphyrin, rubyrin, rosarin, hexaphyrin, sapphyrin, chlorophyl, chlorin, phthalocyanine, porphyrazine, bacteriochlorophyl, pheophytin, or a texaphyrin macrocyclic-based component, or a structure based on one of the corresponding metalated derivatives of these species, or a fluorophore, lumophore, or phosphor, or derived from established laser dyes that include, for example, p-terphenyl, sulforhodamine B, p-quaterphenyl, rhodamine 101, curbostyryl 124, cresyl violet perchlorate, popop, DODC iodide, coumarin 120, sulforhodamine 101, coumarin 2, oxozine 4 perchlorate, coumarin 339, PCM, coumarin 1, oxazine 170 perchlorate, coumarin 138, nile blue A perchlorate, coumarin 106, oxatine 1 perchlorate, coumarin 102, pyridine 1, coumarin 314T, styryl 7, coumarin 338, HTDC iodide, coumarin 151, PTPC iodide, coumarin 4, cryptocyanine, coumarin 314, DOTC iodide, coumarin 30, HITC iodide, coumarin 500, HITC perchlorate, coumarin 307, PTTC iodide, coumarin 334, DTTC perchlorate, coumarin 7, IR-144, coumarin 343, HDITC perchlorate, coumarin 337, IR-NO, coumarin 6, IR-132, coumarin 152, IR-125, coumarin 153, boron-dipyrromethere, HPTS, flourescein, rhodamine 110, 2,7-dichlorofluorescein, rhodamine 65, rhodamin 19 perchlorate, and rhodamine b, or ethynyl, ethenyl, allenyl, naphthyl, butadiynyl, polyvinyl, thiophenyl, furanyl, pyrrolyl, p-diethylylarenyl, pyridinyl, pyrenyl, anthracenyl, phenanthracenyl, pentacenyl, anilinyl, a conjugated heterocycle, or any conjugated heterocycle that bears diethynyl, di(polyynynyl), divinyl, di(polyvinyl), di(thiophenyl), or dipyrrolyl, or aryl having about 3-20 carbon atoms, heteroaryl having about 4 to about 20 carbon atoms, alkenyl or heteroalkenyl having from 2 to about 20 carbon atoms, alkynyl or heteroalkynyl having from 2 to about 20 carbon atoms.

In other aspects, the invention concerns oligomers and polymers of the formula:

PQ-(Sp-PQ-Sp'-PQ'-X)$_n$,X-Sp-PQ-(Sp-PQ-Sp'-PQ'-X)$_n$, X-Sp'-PQ'-(Sp-PQ-Sp'-PQ'-X)$_n$,PQ'-(Sp'-PQ'-Sp-PQ-X)$_n$,X-Sp'-PQ'-(Sp'-PQ'-Sp-PQ-X)$_n$, X-Sp-PQ-(Sp'-PQ'-Sp-PQ-X)$_n$, or X-(Sp-PQ-X-Sp'-PQ'-X)$_n$

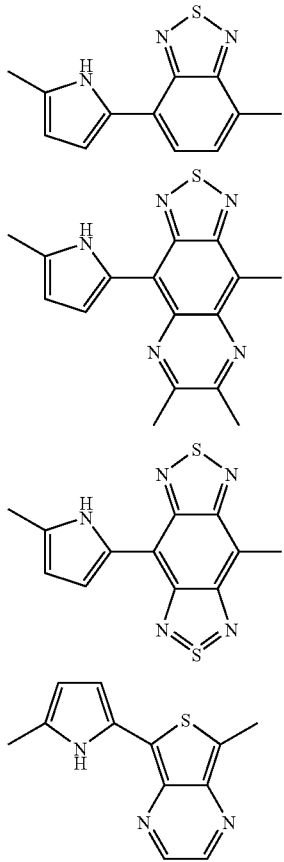

In other aspects, the invention concerns oligomers and polymers of the formula:

PQ-(Sp-PQ-X)$_n$ or X-Sp-PQ-(Sp-PQ-X)$_n$ wherein:
Sp-PQ is:

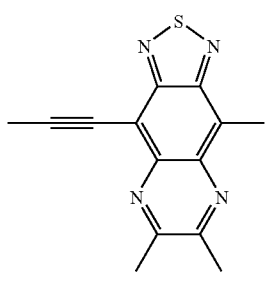

wherein:
Sp-PQ is:
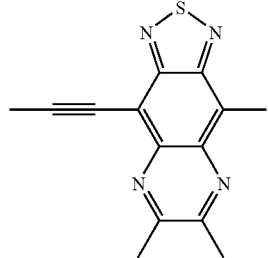
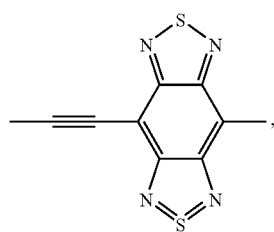
Sp'-PQ' is selected from:
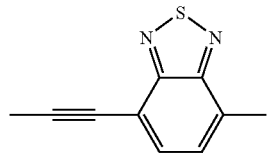
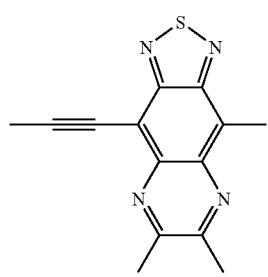
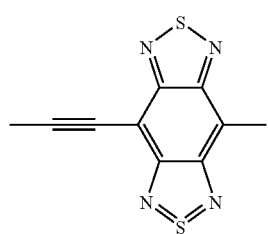
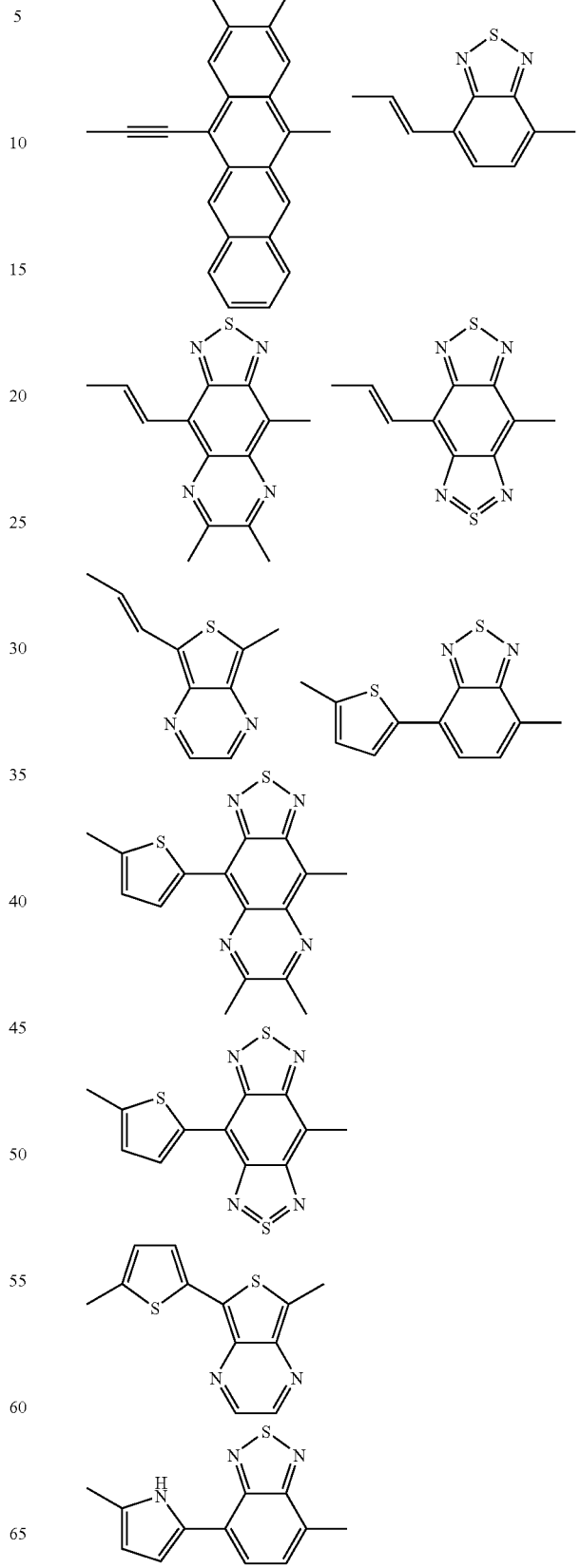

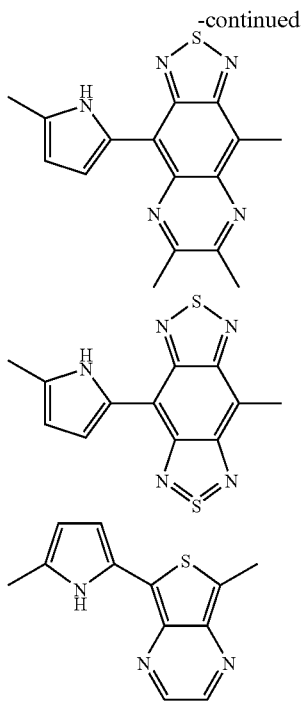

and X is a conjugated structure such as:

a porphycene, porphyrin, rubyrin, rosarin, hexaphyrin, sapphyrin, chlorophyl, chlorin, phthalocyanine, porphyrazine, bacteriochlorophyl, pheophytin, or a texaphyrin macrocyclic-based component, or a structure based on one of the corresponding metalated derivatives of these species, or a fluorophore, lumophore, or phosphor, or derived from established laser dyes that include, for example, p-terphenyl, sulforhodamine B, p-quaterphenyl, rhodamine 101, curbostyryl 124, cresyl violet perchlorate, popop, DODC iodide, coumarin 120, sulforhodamine 101, coumarin 2, oxozine 4 perchlorate, coumarin 339, PCM, coumarin 1, oxazine 170 perchlorate, coumarin 138, nile blue A perchlorate, coumarin 106, oxatine 1 perchlorate, coumarin 102, pyridine 1, coumarin 314T, styryl 7, coumarin 338, HEDC iodide, coumarin 151, PTPC iodide, coumarin 4, cryptocyanine, coumarin 314, DOTC iodide, coumarin 30, HTTC iodide, coumarin 500, HITC perchlorate, coumarin 307, PTTC iodide, coumarin 334, DTTC perchlorate, coumarin 7, JJR-144, coumarin 343, HDITC perchlorate, coumarin 337, IR-NO, coumarin 6, IR-132, coumarin 152, IR-125, coumarin 153, boron-dipyrromethere, HPTS, flourescein, rhodamine 110, 2,7-dichlorofluorescein, rhodamine 65, rhodamin 19 perchlorate, and rhodamine b, or ethynyl, ethenyl, allenyl, naphthyl, butadiynyl, polyvinyl, thiophenyl, furanyl, pyrrolyl, p-diethylylarenyl, pyridinyl, pyrenyl, anthracenyl, phenanthracenyl, pentacenyl, anilinyl, a conjugated heterocycle, or any conjugated heterocycle that bears diethynyl, di(polyynynyl), divinyl, di(polyvinvyl), di(thiophenyl), or dipyrrolyl, or aryl having about 3-20 carbon atoms, heteroaryl having about 4 to about 20 carbon atoms, alkenyl or heteroalkenyl having from 2 to about 20 carbon atoms, alkynyl or heteroalkynyl having from 2 to about 20 carbon atoms.

When it is stated that X is the derivative of a particular moiety, one skilled in the art understands that the X is incorporated into the compound of the invention by conventional techniques. For example, X may be incorporated into the structure through carbon-carbon bond-forming reactions that involve appropriately functionalized Sp, PQ, and/or PQ' moieties.

In other aspects, the invention concerns conjugated oligomers and polymers wherein the conjugated backbone features one or a plurality of Sp-PQ selected from:

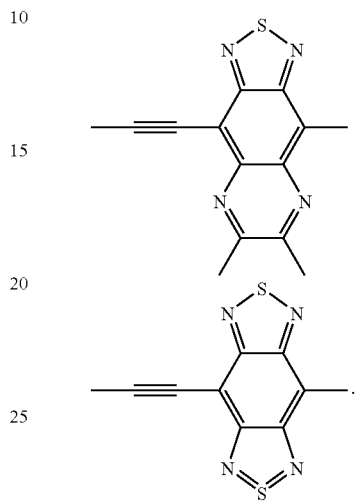

In some embodiments, the invention concerns a device comprising a compound of described herein. In certain embodiments, . the device is a light-emitting diode, a photovoltaic cell, a supercapacitor, a field-effect transistor, or a non-linear optical device, or a device in which a compound described herein serves as a 2-photon-absorbing material, a hole transport material, an electron transport material, a photoconductive material, an electrooptic material, a photorefractive material, an imaging agent, an electro-optic modulator, a waveguiding material, a phase-shifting, material, a signal processing material, a frequency doubling material, an optical limiting material, a lasing material, or a nonlinear optical material. In some embodiments, the device is a light-emitting diode, a photovoltaic cell, a field-effect transistor, a thin-film transistor, an RFED tag, a printed electronic circuit, or a non-linear optical device.

In yet another aspect, the invention relates to a composition comprising:

a polymersome comprising a plurality of amphiphilic copolymers and at least one of the aforementioned compounds. In some embodiments, the amphiphilic copolymer is an amphiphilic block copolymer comprising at least one hydrophilic polymer bonded to at least on hydrophobic polymer. In certain embodiments, the polymersome additionally comprises at least one targeting moiety associated with the surface of said polymersome. In some preferred embodiments, the polymersome is bioresorbable.

DETAILED DESCRIPTION OF ILLUSTRATIVE EMBODIMENTS

In some aspects, the invention concerns compounds, oligomers, or polymers that contain:
PM-(Sp-PQ-Sp-PM)$_n$, PQ-(Sp-PQ)$_n$, PQ-(Sp-PQ-Sp'-PQ')$_n$, PQ-(Sp'-PQ'-Sp-PQ)$_n$, PQ-(Sp-PQ-X)$_n$, X-Sp-PQ-(Sp-PQ-X)$_n$, PQ-(Sp-PQ-Sp'-PQ'-X)$_n$, X-Sp-PQ-(Sp-PQ-Sp'-PQ'-X)$_n$, X-Sp'-PQ'-(Sp-PQ-Sp'-PQ'-X)$_n$, PQ'-(Sp'-PQ'-Sp-PQ-X)$_n$, X-Sp'-PQ'-(Sp'-PQ'-Sp-PQ-X)$_n$, X-Sp-PQ-(Sp'-PQ'-Sp-PQ-X)$_n$, or X-(Sp-PQ-X-Sp'-PQ'-X)$_n$ wherein:
n is 1 or 2;
PM is a (porphinato)(metal) moiety;
Sp is ethynyl;
PQ is

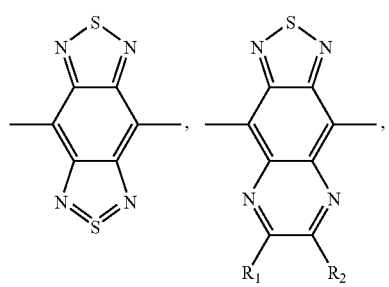

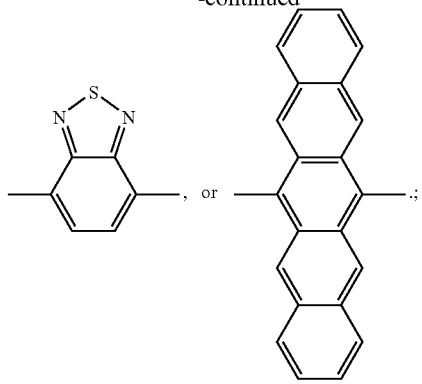

where "-" indicates points of attachment;
Sp' is ethenyl, ethynyl,

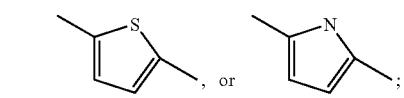

PQ' is

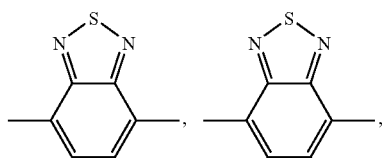

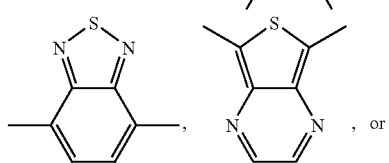

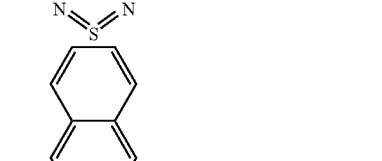

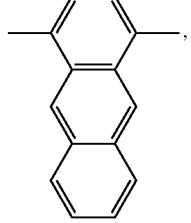

where "-" indicates points of attachment; and
X is a conjugated structure. In some embodiments, PM is a (porphinato)zinc(II) moiety.

Figure 1:
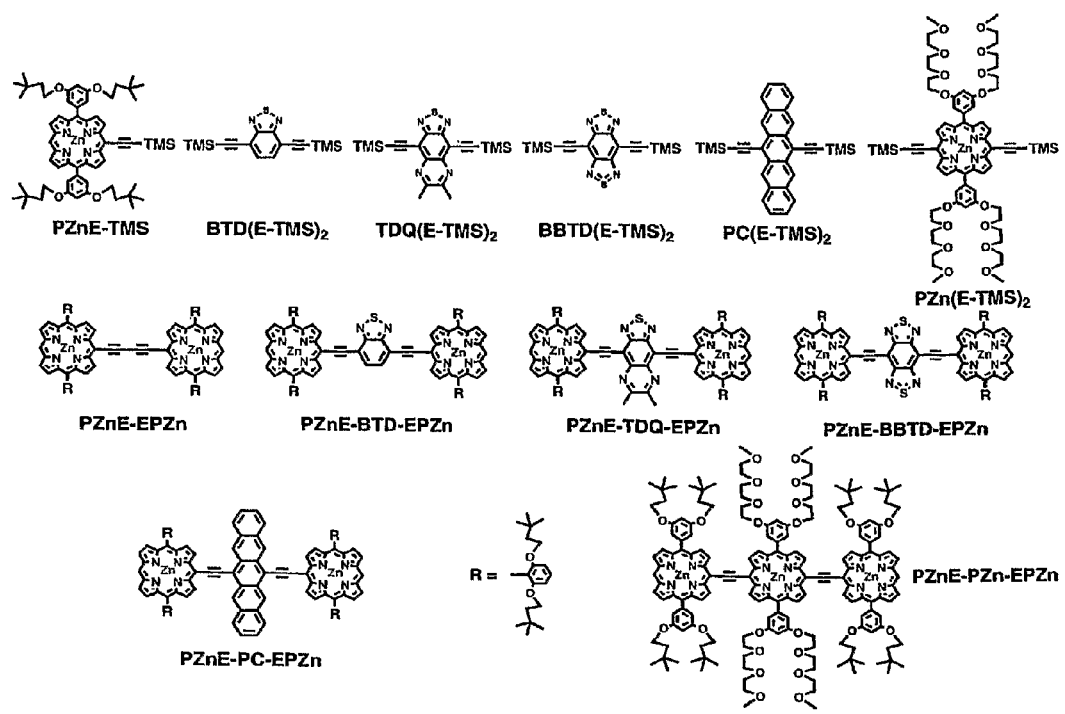
FIG. 1 shows structures of the bis[(porphinato)zinc(II)] derivatives PZnE-EPZn, PZnE-BTD-EPZn, PZnE-PC-EPZn, PZnE-TDQ-EPZn, and PZnE-BBTD-EPZn along with key reference compounds.

In some aspects, the present invention concerns conjugated (porphinato)zinc(II)-spacer-(porphinato)zinc(II) (PZn-Sp-PZn) complexes that feature conjugated Sp structures having varying degrees of proquinoidal character (FIG. 1). These complexes include those of the formula:

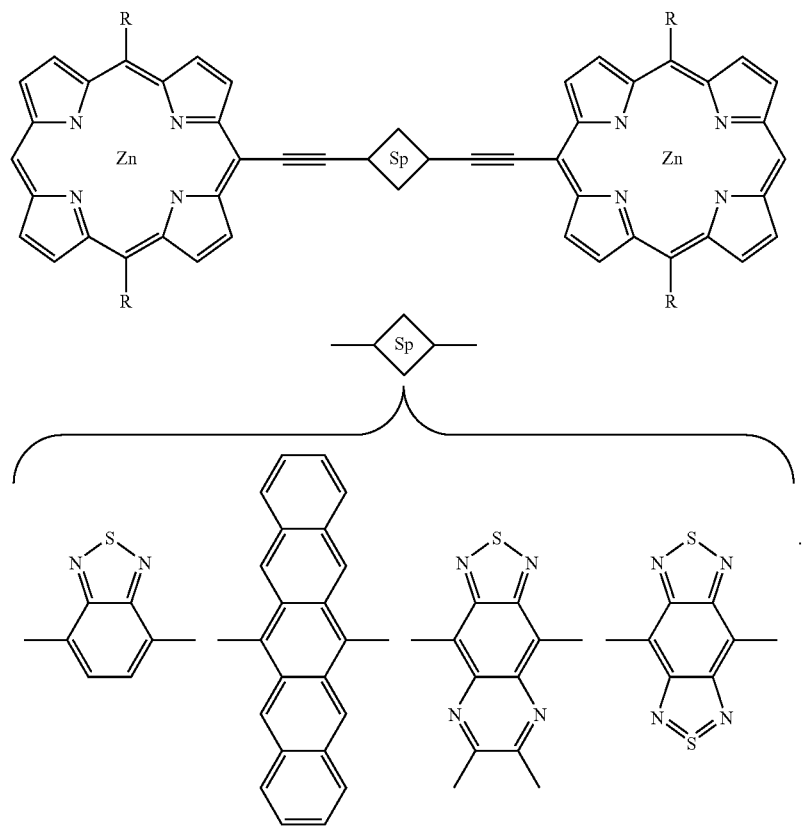

Certain of these Sp moieties, {4,7-diethynylbenzo[c][1,2,5]thiadiazole (E-BTD-E), 6,13-diethynylpentacene (E-PC-E), 4,9-diethynyl-6,7-dimethyl[1,2,5]thiadiazolo[3,4-g]quinoxaline (E-TDQ-E), and 4,8-diethynylbenzo[1,2-c:4,5-c'] bis([1,2,5]thiadiazole) (E-BBTD-E)}, progressively increase the extent of the cumulenic resonance contribution to the PZn-Sp-PZn $S_0$- and $S_1$-state structures, and magnify the electronic communication between the component PZnE units relative to that evinced for a bis[(5,5',-10,20-di(aryl) porphinato)zinc(II)]butadiyne benchmark (PZnE-EPZn). Electronic structural differences, as well as the relative magnitudes of the optical ($E_{op}$) and potentiometric ($E_p$) band gaps of these new conjugated PZn-Sp-PZn structures are rationalized within the context of perturbation theory.

Such compounds are useful in device applications ranging from light-emitting diodes, photovoltaic cells, supercapacitors, field-effect transistors, 2-photon-absorbing materials, hole transport materials, electron transport materials, photoconductive material, nanoelectronics, nanophotonics, photorefractivity, imaging, electro-optic modulation, waveguiding, phase-shifting, signal processing, frequency doubling, optical limiting, lasing, and nonlinear optics.

The compounds are also useful as emissive agents which are associated with a polymersome. Such polymersome compositions find utility in the treatment of disease and in imaging methodology. Certain polymersomes additionally comprise a therapeutic agent. Other polymersomes additionally comprising one or more distinct emissive species.

In some embodiments, the polymersome additionally comprises a secondary emitter, a cytotoxic agent, a magnetic resonance imaging (MRI) agent, positron emission tomography (PET) agent, radiological imaging agent, ultrasound agent, or a photodynamic therapy (PDT) agent. In some embodiments, the polymersome additionally comprises at least one of a secondary emitter, a cytotoxic agent, a magnetic resonance imaging (MRI) agent, positron emission tomography (PET) agent, photodynamic therapy (PDT) agent, radiological imaging agent, ferromagnetic agent, or ferrimagnetic agent, where the emitter or agent is compartmentalized within the aqueous polymersome interior.

The invention also concerns a method of delivering an agent to a biological situs in a tissue or organism comprising administering to the tissue or organism a polymersome having the agent and comprising (a) a plurality of amphophilic block copolymers, each of the amphiphilic block copolymers comprising at least one hydrophilic polymer bonded to at least one hydrophobic polymer; (b) at least one emissive agent of the instant invention that is dispersed within the polymersome membrane; and (b) at least one targeting moiety associated with a surface of the polymersome.

In some embodiments, the invention also concerns a method of ascertaining the presence or absence of a disease state in an organism or tissue comprising: administering a polymersome to a patient, the polymersome comprising (a) a plurality of amphiphilic block copolymers, each of the amphiphilic block copolymers comprising at least one hydrophilic polymer bonded to at least one hydrophobic polymer;

(b) at least one emissive agent of the instant invention that is dispersed within the polymersome membrane; and (c) at least one targeting moiety associated with a surface of the polymersome; providing an instrument optically coupled to a light source, a light detector, or both, and operating the instrument to monitor the amount or distribution of the phorphinato imaging agent within the organism or tissue.

In yet other embodiments, the invention relates to an in vivo method of diagnostics or imaging comprising: contacting a polymersome with tissue within an organism, the polymersome comprising (a) a plurality of amphiphilic block copolymers, each of the amphiphilic block copolymers comprising at least one hydrophilic polymer bonded to at least one hydrophobic polymer; (b) at least one visible- or near infra-red-emissive agent that is dispersed within the polymersome membrane; and (c) at least one targeting moiety associated with a surface of the polymersome; providing an instrument optically coupled to a light source, a light detector, or both, and using the instrument to monitor the amount of the polymersome at a situs within the tissue.

In yet other embodiments, the invention concerns an in vitro diagnostic method comprising: contacting a polymersome with isolated cells, mixtures of cells, or specific cell lines, with the polymersome comprising (a) a plurality of amphiphilic block copolymers, each of the amphiphilic block copolymers comprising at least one hydrophilic polymer bonded to at least one hydrophobic polymer; (b) at least one emissive agent of the instant invention; and (c) at least one targeting moiety associated with a surface of the polymersome; providing an instrument optically coupled to a light source, a light detector, or both, and using the instrument to monitor cell-surface-to-polymersome binding.

Definitions

The term "alkyl", as used herein, whether used alone or as part of another group, refers to a substituted or unsubstituted aliphatic hydrocarbon chain and includes, but is not limited to, straight and branched chains containing from 1 to 20, in some embodiments, 1 to 12 carbon atoms, and in some preferred embodiments 1 to 6 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted. The carbon number as used in the definitions herein refers to carbon backbone and carbon branching, but does not include carbon atoms of the substituents, such as alkoxy substitutions and the like.

"Aryl," as used herein, refers to an aromatic 5- to 13-membered mono- or bi-carbocyclic ring such as phenyl or naphthyl. Preferably, groups containing aryl moieties are monocyclic having 5 to 7 carbon atoms in the ring. Phenyl is one preferred aryl. In some embodiments, phenyl moieties are optionally substituted with $C_1$-$C_6$ alkyl, $C_2$-$C_7$ alkenyl, halogen, hydroxyl, $C_1$-$C_6$ alkoxy, —CN, —$NO_2$, amino, $C_1$-$C_6$ alkylamino, dialkylamino of 1-6 carbon atoms per alkyl group, thio, $C_1$-$C_6$ alkylthio, $C_1$-$C_6$ alkylsulfinyl, $C_1$-$C_6$ alkylsulfonyl, $C_2$-$C_7$ alkoxycarbonyl, of 2-7 carbon atoms alkylcarbonyl, trifluroalkoxy, benzylnitrile or benzoyl.

The term "alkoxy," as used herein, refers to the group R—O— where R is an alkyl group as is defined herein.

The term "glycol" refers to a class of alcohols having 2 hydroxyl groups in each molecule. A glycol group, appearing as a substituent, can be of the formula —O—R—OH where R is an alkyl group. In some embodiments, the alkyl group is a $C_2$, $C_3$, $C_4$, $C_5$, $C_6$, $C_7$, $C_8$, $C_9$, $C_{10}$, $C_{11}$, or $C_{12}$ group.

The present invention is exemplified by the following examples which are not intended to be limiting.

Experimental Section

Materials. All manipulations were carried out under nitrogen previously passed through an $O_2$ scrubbing tower (Schweitzerhall R3-11 catalyst) and a drying tower (Linde 3-Å molecular sieves) unless otherwise stated. Air sensitive solids were handled in a Braun 150-M glove box. Standard Schlenk techniques were employed to manipulate air-sensitive solutions. All solvents utilized in this work were obtained from Fisher Scientific (HPLC grade); tetrahydrofuran (THF) was distilled from K/4-benzoylbiphenyl under $N_2$. Diisopropalamine, Triethylamine, MeOH, and $CH_2Cl_2$ were distilled from $CaH_2$ under $N_2$. Pyridine and piperidine were also dried over $CaH_2$ and distilled under reduced pressure. The catalysts $Pd(PPh_3)_4$, $Pd(PPh_3)_2Cl_2$, tris(dibenzylideneacetone)dipalladium(0) ($Pd_2dba_3$), triphenylarsine ($AsPh_3$) and $P(o-tol)_3$ were purchased from Strem Chemicals and used as received. 4-Bromo-benzo[c][1,2,5]thiadiazole, 4,7-dibromobenzo[c][1,2,5]thiadiazole, were prepared by literature methods (Pilgram, K.; Zupan, M.; Skiles, R. J. Heterocycl. Chem. 1970, 7, 629-633). All NMR solvents were used as received. The supporting electrolyte used in the electrochemical experiments, tetra-re-butylammonium hexafluorophosphate, was recrystallized twice from ethanol and dried under vacuum at 70° C. overnight prior to use. All the other chemicals were used as received.

Synthetic procedures and characterization data for new compounds [4,7-bis[(10,20-bis[2',6'-bis(3,3-dimethyl-1-butyloxy)phenyl]porphinato(II)-5-ylethynyl]benzo[c][1,2,5]thiadiazole (PZnE-BTD-EPZn), 6,13-bis[(10,20-bis[2',6'-bis(3,3-dimethyl-1-butyloxy)phenyl]porphinato)zinc(II)-5-ylethynyl]pentacene (PZnE-PC-EPZn), 4,9-bis[(10,20-bis[2',6'-bis(3,3-dimethyl-1-butyloxy)phenyl]porphinato)zinc(II)-5-ylethynyl]-6,7-dimethyl[1,2,5]thiadiazolo[3,4-g]quinoxaline (PZnE-TDQ-EPZn), 4,8-bis[(10,20-bis[2',6'-bis(3,3-dimethyl-1-butyloxy)phenyl]porphinato)zinc(II)-5-ylethynyl]benzo[1,2-c:4,5-c'][1,2,5]bis([1,2,5]thiadiazole) (PZnE-BBTD-EPZn)] are provided below.

Techniques. Chemical shifts for $^1$H NMR spectra are relative to the tetramethylsilane (TMS) signal in the deuterated solvent (TMS, δ=0.00 ppm). All J values are reported in Hertz. Flash and size exclusion column chromatography were performed on the bench top, using respectively silica gel (EM Science, 230-400 mesh) and Bio-Rad Bio-Beads SX-1 as media. Chemical ionization (CI) and electrospray ionization (ESI) mass spectra were acquired at the Mass Spectrometry Center at the University of Pennsylvania. MALDI-TOF mass spectroscopic data were obtained with a Perspective Voyager DE instrument; samples for these experiments were prepared as micromolar solutions in THF or $CH_2Cl_2$, and dithranol in THF or α-cyano-4-hydroxycinnamic acid in OHbCla/isopropyl alcohol (4:1) were utilized as the matrix.

Instrumentation. Electronic absorption spectra were recorded on an OLIS UV/vis/near-IR spectrophotometry system that is based on the optics of a Cary 14 spectrophotometer. NMR spectra were recorded on 360 MHz DMX-360 or 300 MHz DMX-300 Brisker spectrometers. Cyclic voltammetric measurements were carried out on an EG&G Princeton Applied Research model 273A Potentiostat/Galvanostat. The electrochemical cell used for these experiments utilized a platinum disk working electrode, a platinum wire counter electrode, and a saturated calomel reference electrode (SCE). The reference electrode was separated from the bulk solution by a junction bridge filled with the corresponding solvent/supporting electrolyte solution. The ferrocene/ferrocenium redox couple was utilized as an internal potentiometric standard.

Electronic Structure Calculations. All electronic structure calculations were carried out using the GAUSSIAN 98 programs. See, Frisch, M. J.; Trucks, G. W.; Schlegel, H. B.; Scuseria, G. E.; Robb, M. A.; Cheeseman, J. R.; Zakrzewski, V. G.; Montgomery, J. A.; Stratmann, R. E.; Burant, J. C; Dapprich, S.; Millam, J. M.; Daniels, A. D.; Kudin, K. N.; Strain, M. C; Farkas, O.; Tomasi, J.; Barone, V.; Cossi, M.; Cammi, R.; Mennucci, B.; Pomelli, C; Adamo, C; Clifford, S.; Ochterski, J.; Petersson, G. A.; Ayala, P. Y.; Cui, Q.; Morokuma, K.; Malick, D. K.; Rabuck, A. D.; Raghavachari, K.; Foresman, J. B.; Cioslowski, J.; Ortiz, J. V.; Stefanov, B. B.; Liu, G.; Liashenko, A.; Piskorz, P.; Komaromi, I.; Gomperts, R.; Martin, R. L.; Fox, D. J.; Keith, T.; Al-Laham, M. A.; Peng, C. Y.; Nanayakkara, A.; Gonzalez, C; Challacombe, M.; Gill, P. M. W.; Johnson, B. G.; Chen, W.; Wong, M. W.; Andres, J. L.; Head-Gordon, M.; Replogle, E. S.; Pople, J. A. Gaussian 98, Revision A.9; Gaussian, Inc: Pittsburgh, Pa., 1998. Geometry optimizations and semiempirical electronic structural calculations were performed using the PM3 method. In order to minimize computational effort, the solubilizing alkoxy substituents of the PZn-Sp-PZn structures, the PZnE trimethylsilyl group, and the methyl groups of 6,7-dimethyl[1,2,5]thiadiazolo[3,4-g]quinoxaline were replaced by hydrogen. Structural models for PZnE-EPZn, PC, BBTD, PZnE-PC-EPZn and PZnE-BBTD-EPZn were optimized within $D_{2h}$ constraints, while optimal PZnE, BTD, TDQ, PZnE-BTD-EPZn and PZnE-TDQ-EPZn structures were computed for $C_{2v}$ symmetry. Orbital contour plots were visualized with the gOpenMol program. See, Laaksonen, L. gOpenMol, Version 2.0; Espoo, Finland, 2001.

Synthesis. Structures of the PZn-Sp-PZn supermolecules along with related ethynylated Sp and PZn reference compounds are shown in FIG. 1. These PZn-Sp-PZn species were synthesized by palladium (Pd)-mediated cross-coupling reactions involving appropriately substituted (porphinato) zinc(II) (PZn) compounds and Sp units (see Supporting Information). The PZn-containing structures of FIG. 1 exploit 2',6'-bis(3,3-dimethyl-1-butyloxy)phenyl groups as 10- and 20-meso-porphyrin substituents, which facilitate excellent solubility and straightforward assignment of $^1$H-NMR spectra [Susumu, K.; Therien, M. J. *J. Am. Chem. Soc.* 2002, 124, 8550-8552; Uyeda, H. T.; Zhao, Y.; Wostyn, K.; Asselberghs, I.; Clays, K.; Persoons, A.; Therien, M. J. *J. Am. Chem. Soc.* 2002, 124, 13806-13813]. 4,7-Diethynylbenzo[c][1,2,5]thiadiazole (E-BTD-E), 6,13-diethynylpentacene (E-PC-E), 4,9-diethynyl-6,7-dimethyl[1,2,5]thiadiazolo[3,4-g]quinoxaline (E-TDQ-E), and 4,8-diethynylbenzo[1,2-c:4,5-c']bis([1,2,5] thiadiazole) (E-BBTD-E) were selected as proquinoidal Sp units.

The nature of the functionalized PZn and Sp moieties used in the synthesis of the corresponding PZn-Sp-PZn complexes varied with Sp electronic structure. For the PZn-Sp-PZn structure featuring a E-BTD-E Sp unit (PZnE-BTD-EPZn, FIG. 1), the coupling reaction between (5-ethynyl-10,20-bis [2',6'-bis(3,3-dimethyl-1-butyloxy)phenyl]porphinato)zinc (II) and 4,7-dibromobenzo[c][1,2,5]thiadiazole gave a mixture of products that included not only the target molecule, but also the butadiyne-bridged bis[(porphinato)zinc(II)] complex (PZnE-EPZn). As these two species were difficult to separate by both silica gel and size exclusion column chromatography under the conditions employed, PZnE-BTD-EPZn was synthesized via a Pd-mediated coupling reaction involving (5-iodo-10,20-bis[2',6'-bis(3,3-dimethyl-1-butyloxy)phenyl]porphinato)zinc(II) and 4,7-bis(trimethylsilylethynyl) benzo[c][1,2,5]thiadiazole in which in situ deprotection of the trimethylsilyl (TMS) group with $K_2CO_3$ was utilized. An identical in situ deprotection strategy was utilized in the synthesis of PZnE-PC-EPZn, as 6,13-diethynylpentacene (E-PC-E) possesses low solubility. Respective PZn-Sp-PZn complexes utilizing thiadiazoloquinoxaline and benzobis (thiadiazole) moieties as Sp components (PZnE-TDQ-EPZn and PZnE-BBTD-EPZn, FIG. 1) were synthesized successfully from (5-ethynyl-10,20-bis[2',6'-bis(3,3-dimethyl-1-butyloxy)phenyl]porphinato)zinc(II) and the corresponding dibromo proquinoid spacer derivatives, as trace PZnE-EPZn contaminants could easily be separated from the PZn-Sp-PZn product by silica gel column chromatography.

Steady-State Absorption Spectra. Electronic absorption spectra for the PZn-Sp-PZn complexes, along with the spectrum for the bis[(5,5',-10,20-di(aryl)porphinato)zinc(II)] butadiyne (PZnE-EPZn) benchmark, are displayed in FIG. 2. Analogous electronic spectra for trimethylsilyl-protected analogues of proquinoidal Sp reference compounds E-BTD-E, E-PC-E, E-TDQ-E and E-BBTD-E, as well as comprehensive tabulated electronic absorption spectral data, are contained in the Supporting Information. As expected for the mode of porphyrin-to-porphyrin connectivity and the nature of the conjugated components, extensive electronic interactions are manifest between the PZn and Sp components of these structures. The electronic absorption spectrum for PZnE-EPZn (FIG. 2A), as well as the linear electronic spectra of these PZn-Sp-PZn compounds (FIG. 2B-E), are dominated by two absorption manifolds derived from the classic porphyrin B (Soret)-($S_0 \rightarrow S_2$) and Q-band ($S_0 \rightarrow S_1$) transitions. The gross spectral features of these species evince the hallmarks of extensive π conjugation and exciton coupling, and have been analyzed in detail for a wide-range of structurally related compounds. See, Lin, V. S.-Y.; DiMagno, S. G.; Therien, M. J. *Science* 1994, 264, 1105-1111; Lin, V. S.-Y.; Therien, M. J. *Chem. Eur. J.* 1995, 1, 645-651; Kumble, R.; Palese, S.; Lin, V. S.-Y.; Therien, M. J.; Hochstrasser, R. M. *J. Am. Chem. Soc.* 1998, 120, 11489-11498; Shediac, R.; Gray, M. H. B.; Uyeda, H. T.; Johnson, R. C; Hupp, J. T.; Angiolillo, P. J.; Therien, M. J. *J. Am. Chem. Soc.* 2000, 122, 7017-7033; Susumu, K.; Therien, M. J. *J. Am. Chem. Soc.* 2002, 124, 8550-8552; Rubtsov, I. V.; Susumu, K.; Rubtsov, G. I.; Therien, M. J. *J. Am. Chem. Soc.* 2003, 125, 2687-2696.

The Soret band regions of these PZn-Sp-PZn compounds show splittings characteristic of extensive excitonic interactions [Kasha, M.; Rawls, H. R.; El-Bayoumi, M. A. *Pure*

Figure 2:
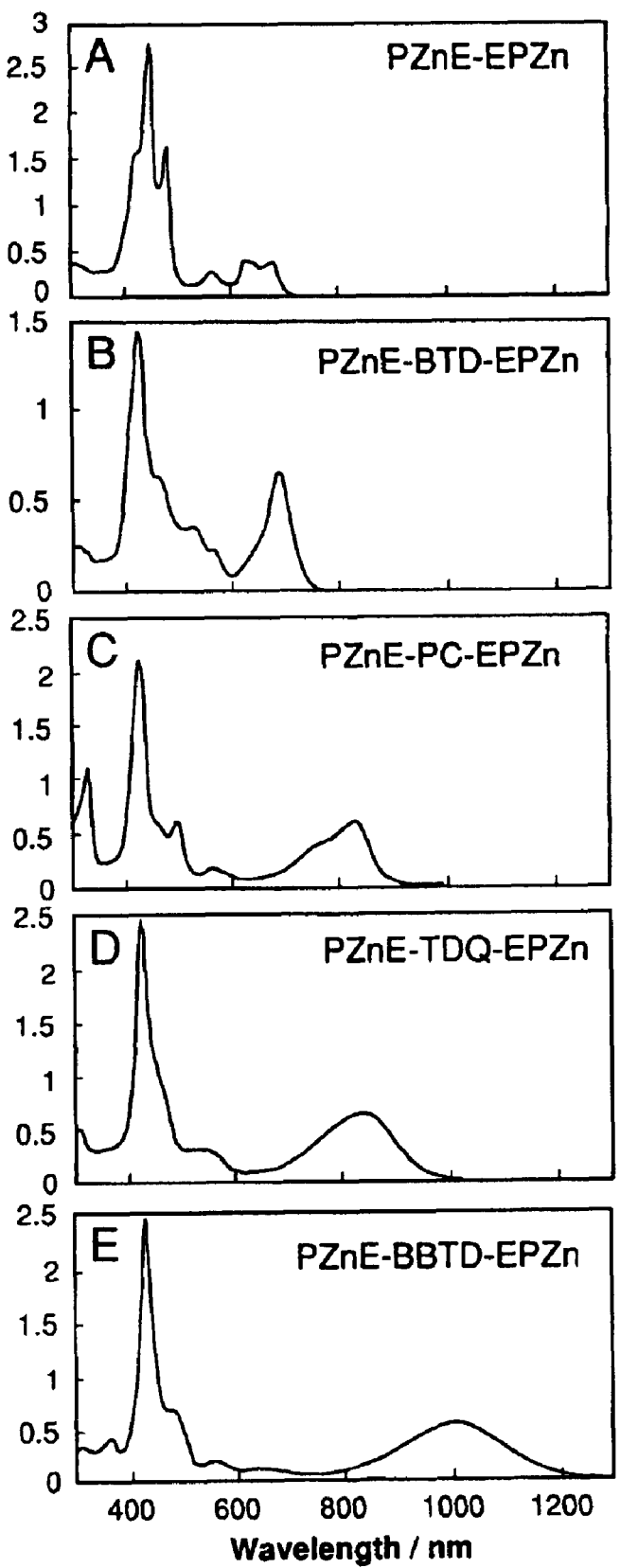
FIG. 2 shows electronic absorption spectra of: (A) PZnE-EPZn, (B) PZnE-BTD-EPZn, (C) PZnE-PC-EPZn, (D) PZnE-TDQ-EPZn, and (E) PZnE-BBTD-EPZn recorded in THF solvent.

Appl. Chem. 1965, 11, 371-392]. Note that the PZnE-BTD-EPZn, PZnE-PC-EPZn, PZnE-TDQ-EPZn, and PZnE-BBTD-EPZn spectra (FIG. 2) display a sharp B-state absorption close in energy to that of 5-ethynyl(porphinato)zinc(II) reference compound (PZnE, FIG. 1; see Supporting Information); interestingly, this high energy component of the B-state manifold of these compounds displays less structure than that observed in the PZnE-EPZn spectrum (FIG. 2A). Congruent with the body of spectroscopic data obtained for PZnE-EPZn and related ethyne- and butadiyne-bridged bis(PZn) compounds [Lin, V. S.-Y.; DiMagno, S. G.; Therien, M. J. *Science* 1994, 264, 1105-1111; Lin, V. S.-Y.; Therien, M. J. *Chem. Eur. J.* 1995, 1, 645-651; Kumble, R.; Palese, S.; Lin, V. S.-Y.; Therien, M. J.; Hochstrasser, R. M. *J. Am. Chem. Soc.* 1998, 120, 11489-11498; Shediac, R.; Gray. M. H. B.; Uyeda, H. T.; Johnson, R. C; Hupp, J. T.; Angiolillo, P. J.; Therien, M. J. *J. Am. Chem. Soc.* 2000, 122, 7017-7033; Susumu, K.; Therien, M. J. *J. Am. Chem. Soc.* 2002, 124, 8550-8552; Rubtsov, I. V.; Susumu, K.; Rubtsov, G. I.; Therien, M. J. *J. Am. Chem. Soc.* 2003, 125, 2687-2696; Anderson, H. L. *Inorg. Chem.* 1994, 33, 972-981; Beljonne, D.; O'Keefe, G. E.; Hamer, P. J.; Friend, R. H.; Anderson, H. L.; Brédas, J. L. *J. Chem. Phys.* 1997, 106, 9439-9460; Angiolillo, P. J.; Lin, V. S.-Y.; Vanderkooi, J. M.; Therien, M. J. *J. Am. Chem. Soc.* 1995, 117, 12514-12527; O'Keefe, G. E.; Denton, G. J.; Harvey, E. J.; Phillips, R. T.; Friend, R. H.; Anderson, H. L. *J. Chem. Phys.* 1996, 104, 805-811]. This spectral signature reflects the diminished y-polarized B-state dipolar interaction (y taken orthogonal to the highly conjugated axis of the structure) that occurs with increasing PZn-PZn distance for the PZnE-BTD-EPZn, PZnE-PC-EPZn, PZnE-TDQ-EPZn, and PZnE-BBTD-EPZn supermolecules, consistent with expectations based on the point-dipole approximation of the general exciton model originally developed by Kasha, Kasha, M.; Rawls, H. R.; El-Bayoumi, M. A. *Pure Appl. Chem.* 1965, 11, 371-392. In contrast, the low energy, x-polarized B-state transitions along the vector defined by the ethyne moieties of these PZn-Sp-PZn compounds are markedly reduced in absolute intensity with respect to the $B_x$ band centered at 481 nm in the PZnE-EPZn spectrum, and less significant relative to their respective prominent y-polarized B-state absorptions (FIG. 2, Table 12).

TABLE 1

Prominent absorption band wavelength, energies, and extinction coefficients of conjugated PZn-Sp-PZn compounds relative to the PZnE-TMS benchmark in THF solvent.

| | UV-region | | | B-band region | | | Q-band region | | |
|---|---|---|---|---|---|---|---|---|---|
| | λ(nm) | ν(cm$^{-1}$) | log(ε) | λ(nm) | ν(cm$^{-1}$) | log(ε) | λ(nm) | ν(cm$^{-1}$) | log(ε) |
| PZnE-TMS | | | | 428 | 23,364 | (5.53) | 562 | 17,794 | (4.17) |
| | | | | | | | 603 | 16,584 | (3.92) |
| PZnE-EPZn | 308 | 32,468 | (4.56) | 423 | 23,640 | (5.19) | 566 | 17,668 | (4.42) |
| | | | | 449 | 22,272 | (5.46) | 628 | 15,924 | (4.60) |
| | | | | 481 | 20,790 | (5.21) | 678 | 14,749 | (4.58) |
| PZnE-BTD-EPZn | 313 | 31,949 | (4.39) | 426 | 23,474 | (5.16) | 524 | 19,084 | (4.55) |
| | | | | 465 | 21,505 | (4.79) | 566 | 17,668 | (4.34) |
| | | | | | | | 689 | 14,514 | (4.81) |
| PZnE-PC-EPZn | 326 | 30,675 | (5.05) | 421 | 23,753 | (5.32) | 555 | 18,018 | (4.26) |
| | | | | 493 | 20,284 | (4.79) | 823 | 12,151 | (4.78) |
| PZnE-TDQ-EPZn | 305 | 32,787 | (4.71) | 423 | 23,641 | (5.38) | 531 | 18,832 | (4.51) |
| | | | | | | | 839 | 11,919 | (4.80) |
| PZnE-BBTD-EPzn | 308 | 32,468 | (4.56) | 429 | 23,310 | (5.39) | 551 | 18,149 | (4.33) |
| | 363 | 27,548 | (4.65) | 479 | 20,877 | (4.84) | 638 | 15,674 | (4.16) |
| | | | | | | | 1006 | 9,940 | (4.75) |

Figure 3:
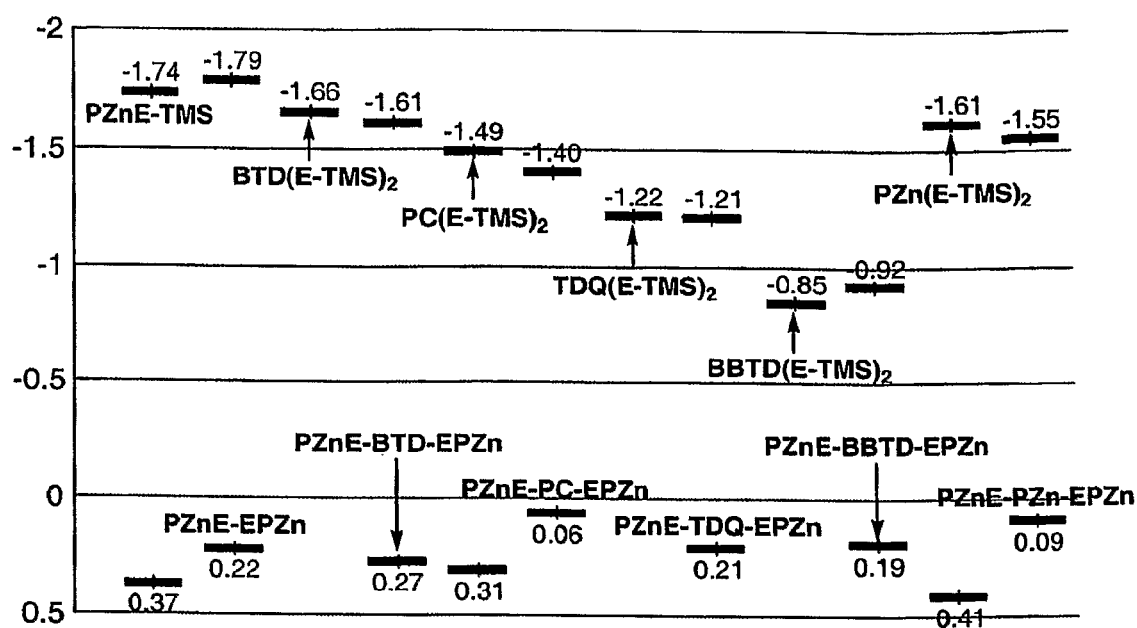
FIG. 3 shows schematic highlighting the potentiometrically determined HOMO and LUMO energy levels of the PZn-Sp-PZn complexes relative to those of ethyne-functionalized PZn and proquinoidal Sp moieties. Redox potentials shown are relative to the ferrocene/ferrocenium (Fc/Fc$^+$) redox couple, which was used as an internal standard in these experiments.
Figure 4:
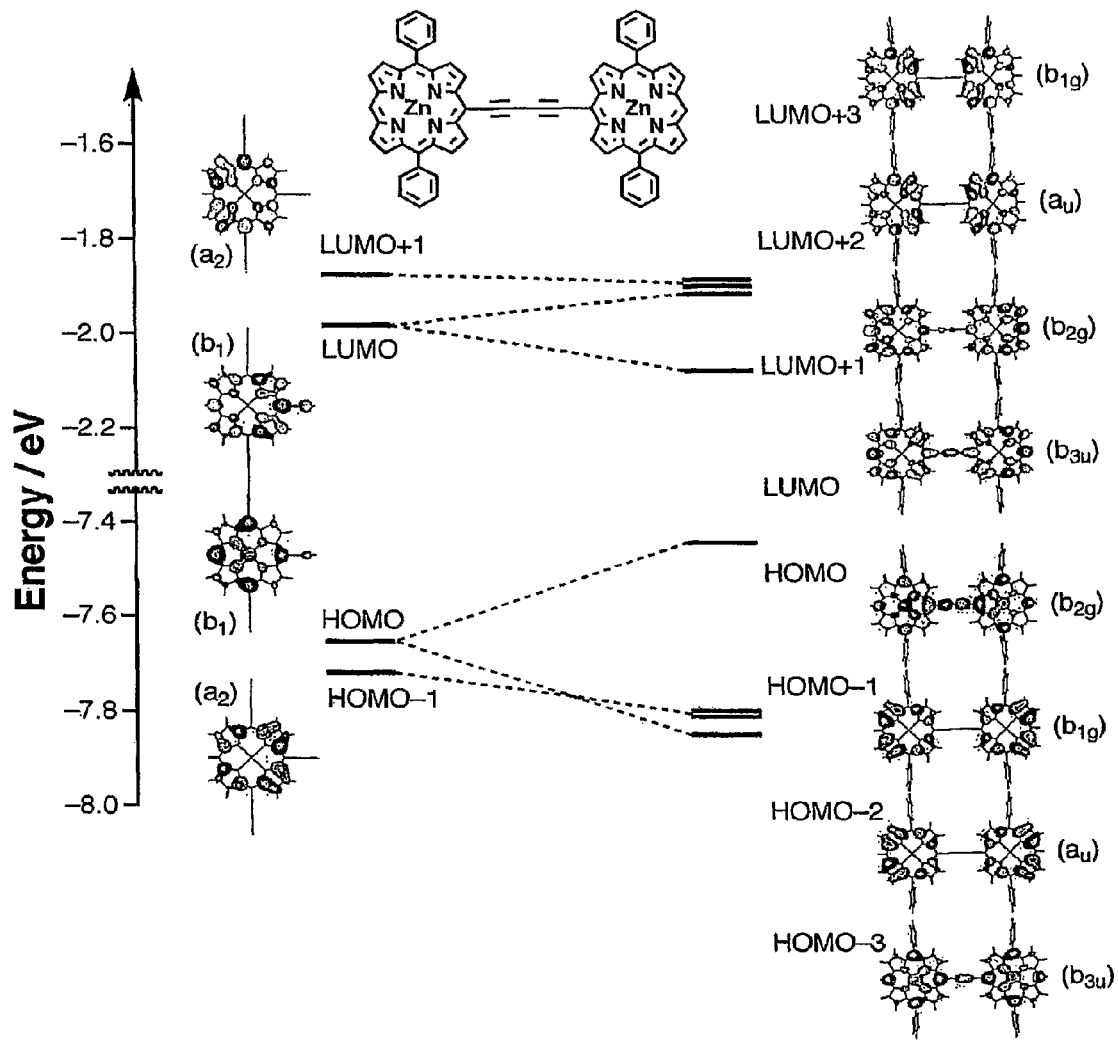
FIG. 4 shows frontier orbital correlation diagram for PZnE and PZnE-EPZn.
Figure 5:
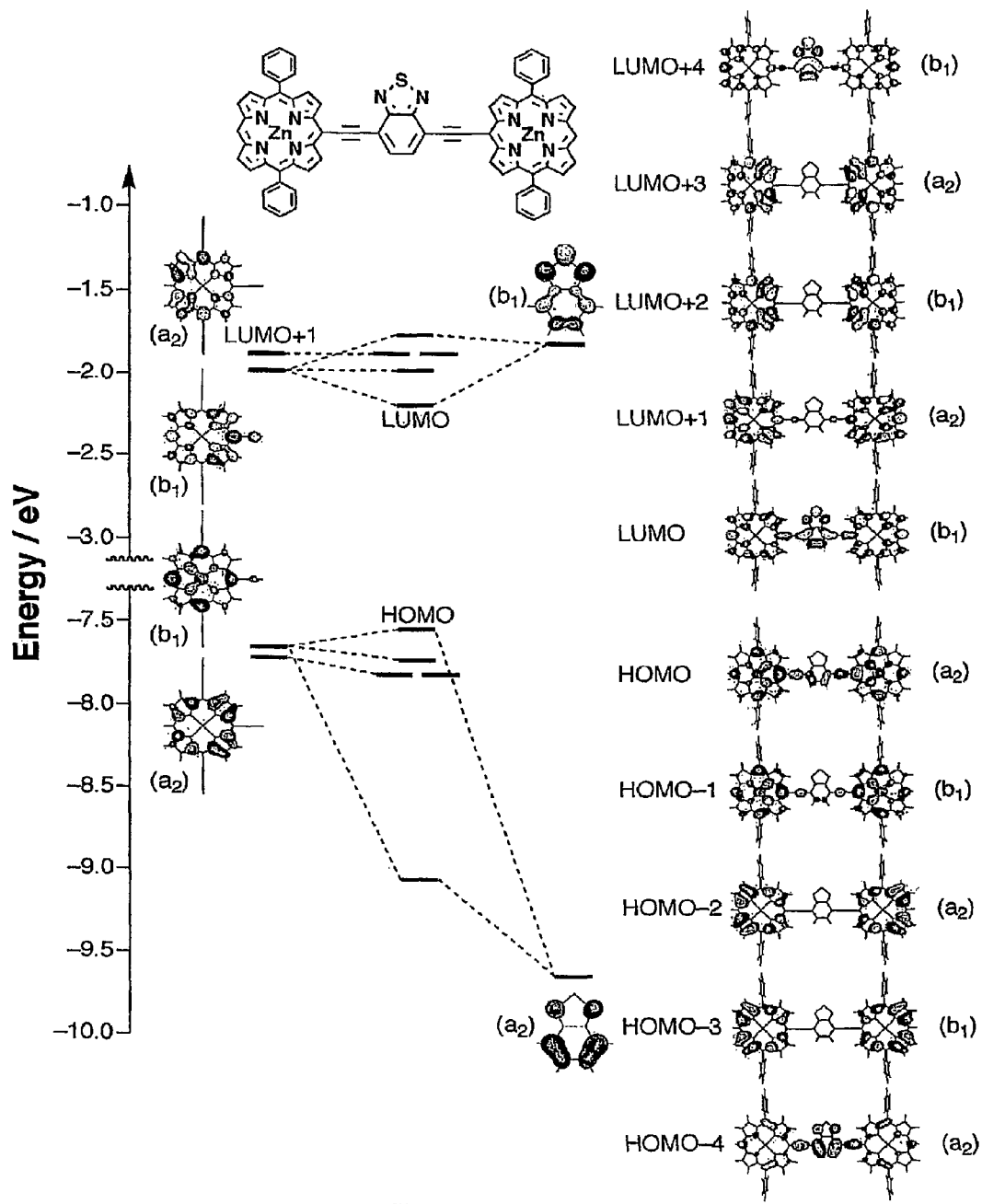
FIG. 5 shows frontier orbital correlation diagram for PZnE, benzothiadiazole (BTD), and PZnE-BTD-EPZn.

This decrease in x-polarized B-state oscillator strength observed in the FIG. 2 spectra for PZnE-BTD-EPZn, PZnE-PC-EPZn, PZnE-TDQ-EPZn, and PZnE-BBTD-EPZn relative to that manifest for PZnE-EPZn, reflects enhanced $B_x$-state intensity borrowing by the corresponding Q-state absorptions driven by the proquinoidal PZn-to-PZn bridging units [Shediac, R.; Gray, M. H. B.; Uyeda, H. T.; Johnson, R. C; Hupp, J. T.; Angiolillo, P. J.; Therien, M. J. *J. Am. Chem. Soc.* 2000, 122, 7017-7033; Gouterman, M. In *The Porphyrins*; Dolphin, D., Ed.; Academic Press: London, 1978; Vol. III, p 1-165]. This augmentation of x-polarized Q-state absorption oscillator strength increases concomitantly with the ability of the $S_0$ and $S_1$ states of these species to delocalize charge (Tables 1 and 2, vide infra), [Lin, V. S.-Y.; DiMagno, S. G.; Therien, M. J. *Science* 1994, 264, 1105-1111; Lin, V. S.-Y.; Therien, M. J. *Chem. Eur. J.* 1995, 1, 645-651; Susumu, K.; Therien, M. J. *J. Am. Chem. Soc.* 2002, 124, 8550-8552] and tracks with the magnitude of the $Q_x$ absorption wavelength [Compound, ($\lambda_{max}(Q_x$ band)): PZnE-EPZn (678 nm), PZnE-BTD-EPZn (689 nm), PZnE-PC-EPZn (823 nm), PZnE-TDQ-EPZn (839 nm) and PZnE-BBTD-EPZn (1006 nm)]. Note that the full spectral width at half maximum (FWHM) of the $Q_x$-state absorption manifold follows a similar trend with PZnE-EPZn<PZnE-BTD-EPZn<PZnE-PC-EPZn<PZnE-TDQ-EPZn-PZnE-BBTD-EPZn (FIG. 2, Table 1). In this regard, note that the $Q_x$ manifold spectral band shapes for PZnE-TDQ-EPZn and PZnE-BBTD-EPZn tail extensively at low energy, with the PZnE-BBTD-EPZn spectrum displaying measurable oscillator strength well beyond 1200 nm (FIG. 2). Absorption wavelengths, energies, and extinction coefficients for the prominent transitions of these compounds are tabulated in Table 2.

tionalized PZn and proquinoidal Sp moieties, PZnE-EPZn, and a related tris[(porphinato)zinc(II)] complex, (5,15-bis [[(5',-10',20'-bis[3,5-di(3,3-dimethyl-1-butyloxy)phenyl] porphinato)zinc(II)]ethynyl]-10,20-bis[3,5-di(9-methoxy-1, 4,7-trioxanonyl)phenyl]porphinato)zinc(II) (PZnE-PZn-EPZn). The cyclic voltammetric data shown in this figure highlight a number of electronic structural features of these PZn-Sp-PZn species. PZn-Sp-PZn $E_{1/2}^{0/+}$ values vary modestly with Sp electronic structure over a 0.21 eV range, with HOMO level destabilization increasing in the order PZnE-BTD-EPZn<PZnE-EPZn PZnE-TDQ-EPZn<PZnE-BBTD-EPZn<PZnE-PC-EPZn (FIG. 3). In contrast, measured PZn-Sp-PZn $E_{1/2}^{-/0}$ values span a 0.87 eV potentiometric domain, mirroring closely the relative changes observed for $E_{1/2}^{-/0}$ determined for their corresponding trimethylsilyl-elaborated Sp [Sp(E-TMS)$_2$] structures, and evincing LUMO level stabilization that escalates in the order PZnE-EPZn<PZnE-BTD-EPZn<PZnE-PC-EPZn<PZnE-TDQ-EPZn<PZnE-BBTD-EPZn. This strong dependence of PZn-Sp-PZn $E_{1/2}^{-/0}$ values upon the nature of the building block ethyne-elaborated Sp moiety plays the predominant role in determining the magnitude of the potentiometrically determined HOMO-LUMO gaps ($E_p$; $E_{1/2}^{0/+}-E_{1/2}^{-/0}$) within this series of supermolecular bis(PZn) compounds that feature proquinoidal Sp units [Compound, ($E_p$): PZnE-EPZn (2.01 eV), PZnE-BTD-EPZn (1.88 eV), PZnE-PC-EPZn (1.46 eV), PZnE-TDQ-EPZn (1.42 eV) and PZnE-BBTD-EPZn (1.11 eV); see FIG. 3, Table 3]. Note that despite augmented PZn-to-PZn centroid-to-centroid distances, the magnitudes of the potentiometrically evaluated HOMO-LUMO gaps for these PZn-Sp-PZn structures are markedly diminished relative to the PZnE-EPZn benchmark. Further, given that PZnE-PZn-EPZn can be considered a bis(PZn) complex bridged by a 5,15-diethynyl(porphinato)zinc(II) (PZnE$_2$) Sp moiety, the fact that $E_p$ for this structure (FIG. 3) exceeds that determined for PZnE-

TABLE 2

Comparative integrated oscillator strengths and absorptive domains of the blue and red spectral regions of conjugated porphyrin dimers relative to the PZnE-TMS benchmark.[a]

| Compound | FWHM[b] B-band region [cm$^{-1}$, (nm)] | Oscillator Strength B-band region[d] | FWHM[e] Q-band region [cm$^{-1}$, (nm)] | Oscillator Strength Q-band region[f] | Total Oscillator Strength[g] |
|---|---|---|---|---|---|
| PZnE-TMS | 696 (428) | 1.059 | 756 (562) | 0.062 | 1.121 |
|  |  |  | 457 (603) |  |  |
| PZnE-EPZn | 1976 (449)[c] | 3.643 | 1512 (566) | 0.467 | 5.197 |
|  | 592 (481)[c] |  | 588 (628) |  |  |
|  |  |  | 536 (678) |  |  |
| PZnE-BTD-EPZn | 2323 (426)[c] | 2.108 | 1180 (689) | 0.719 | 3.519 |
| PZnE-PC-EPZn | 1745 (421) | 2.667 | 1992 (823) | 0.737 | 5.456 |
|  | 1014 (493)[c] |  |  |  |  |
| PZnE-TDQ-EPZn | 1945 (423) | 3.076 | 2510 (839) | 1.144 | 5.515 |
| PZnE-BBTD-EPZn | 1623 (429) | 2.803 | 2341 (1006) | 0.972 | 5.167 |
|  | 2053 (479)[c] |  |  |  |  |

[a]From electronic absorption spectra recorded in THF solvent.
[b]Taken as the spectral width of the B-band region at half the height of the absorption noted.
[c]Taken as twice value of half the spectral width of the B-band region at half the height of the absorption noted.
[d]Oscillator strengths calculated over the following wavelength domains: PZnE-TMS (360~470 nm); PZnE-EPZn (360~530 nm); PZnE-BTD-EPZn (360~510 nm); PZnE-PC-EPZn (360~535 nm); PZnE-TDQ-EPZn (360~510 nm); PZnE-BBTD-EPZn (380~525 nm).
[e]Entries correspond to the spectral breadth of the transition envelope centered at the wavelength in parentheses.
[f]Oscillator strengths calculated over the following wavelength domains: PZnE-TMS (470~650 nm); PZnE-EPZn (530~750 nm); PZnE-BTD-EPZn (510~850 nm); PZnE-PC-EPZn (535~1000 nm); PZnE-TDQ-EPZn (510~1000 nm); PZnE-BBTD-EPZn (525~1400 nm).
[g]Oscillator strengths calculated over the following wavelength domains: PZnE-TMS (360~650 nm); PZnE-EPZn (280~750 nm); PZnE-BTD-EPZn (280~850 nm); PZnE-PC-EPZn (280~1000 nm); PZnE-TDQ-EPZn (280~1100 nm); PZnE-BBTD-EPZn (280~1400 nm).

Electrochemical Properties. FIG. 3 highlights the potentiometrically determined HOMO and LUMO energy levels of the PZn-Sp-PZn complexes relative to those of ethyne-func- TDQ-EPZn, PZnE-PC-EPZn, and PZnE-BBTD-EPZn, demonstrates that proquinoidal Sp electronic structure, in contrast to Sp π-aromatic size, can be the more important determinant of the extent of π-conjugation in π-conjugated oligomers and polymers.

TABLE 3

Optical HOMO-LUMO gaps ($E_{op}$S) and potentiometrically determined HOMO-LUMO gaps ($E_p$S) of the PZn-Sp-PZn complexes relative to those of ethyne-functionalized PZn and proquinoidal Sp moieties.

| | PZnE-TMS | PZnE-EPZn | BTD(E-TMS)$_2$ | PZnE-BTD-EPZn | PC(E-TMS)$_2$ | PZnE-PC-EPZn | TDQ(E-TMS)$_2$ | PZnE-TDQ-EPZn | BBTD(E-TMS)$_2$ | PZnE-BBTD-EPZn |
|---|---|---|---|---|---|---|---|---|---|---|
| $E_{op}(max)^a$ | 2.06 | 1.83 | 3.25 | 1.80 | 1.94 | 1.51 | 2.46 | 1.48 | 2.18 | 1.23 |
| $E_{op}(edge)^b$ | 2.01 | 1.77 | 2.95 | 1.69 | 1.89 | 1.41 | 2.31 | 1.31 | 2.01 | 1.05 |
| $E_p$ | 2.11 | 2.01 | d | 1.88 | 1.80 | 1.46 | d | 1.42 | d | 1.11 |

[a] Optical HOMO-LUMO gap determined from the lowest absorption maximum measured in THF.
[b] Optical HOMO-LUMO gap determined from the absorption edge measured in THF. The absorption edge is defined as the wavelength on the red side of the lowest energy absorption band where the slope changes abruptly.
[c] Potentiometrically determined HOMO-LUMO gap ($E_{1/2}^{0/+} - E_{1/2}^{-/0}$) measured in $CH_2Cl_2$.
[d] Irreversible oxidation; value not determined.

While the magnitudes of PZnE-BTD-EPZn and PZnE-PC-EPZn $E_p$ values suggest respective HOMOs and LUMOs that feature substantial conjugative interactions between the PZn, Sp, and ethyne units (FIG. 3), the highly stabilized LUMOs of PZnE-TDQ-EPZn and PZnE-BBTD-EPZn are unusual: note that the PZnE-TDQ-EPZn and PZnE-BBTD-EPZn one-electron reduction potentials resemble those obtained respectively for TDQ(E-TMS)$_2$ and BBTD(E-TMS)$_2$, potentially indicating that radical anion state electron density is largely localized on the Sp fragments of these PZn-Sp-PZn supermolecules. While electronic structure calculations provide further insight into this matter, it is important to note that the optical band gaps ($E_{op}$ values) of PZnE-BTD-EPZn, PZnE-PC-EPZn, PZnE-TDQ-EPZn, and PZnE-BBTD-EPZn track closely with their corresponding $E_p$s (FIGS. 2-3, Tables 2-3). These data, coupled with the facts that: (i) the steady state absorption spectra indicate that the visible and NIR x-polarized excitations evince extensive mixing of PZn- and Sp-derived electronic states, (ii) the magnitude of the LUMO-level stabilization in the PZnE-BTD-EPZn, PZnE-PC-EPZn, PZnE-TDQ-EPZn, and PZnE-BBTD-EPZn series is extensive with respect to the corresponding HOMO-level destabilization evinced in these structures, suggest that the quinoidal resonance contribution to the low lying singlet electronically excited states exceeds greatly that for the ground-state, thus giving rise to the expectation that the excited singlet wavefunctions of these PZn-Sp-PZn compounds should feature unusual degrees of electronic delocalization (vide infra).

Figure 7:
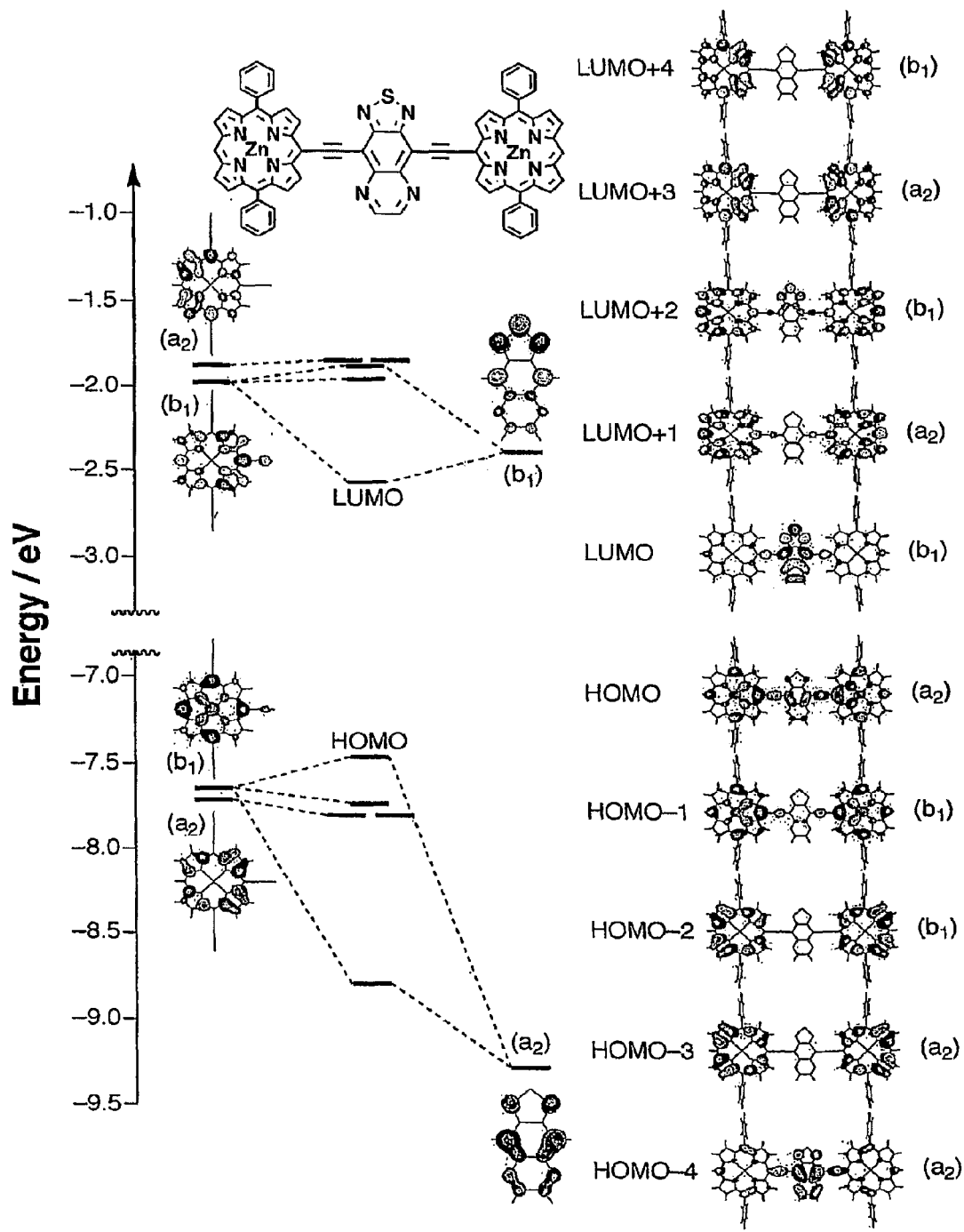
FIG. 7 shows frontier orbital correlation diagram for PZnE, thiadiazoloquinoxaline (TDQ), and PZnE-TDQ-EPZn.
Figure 8:
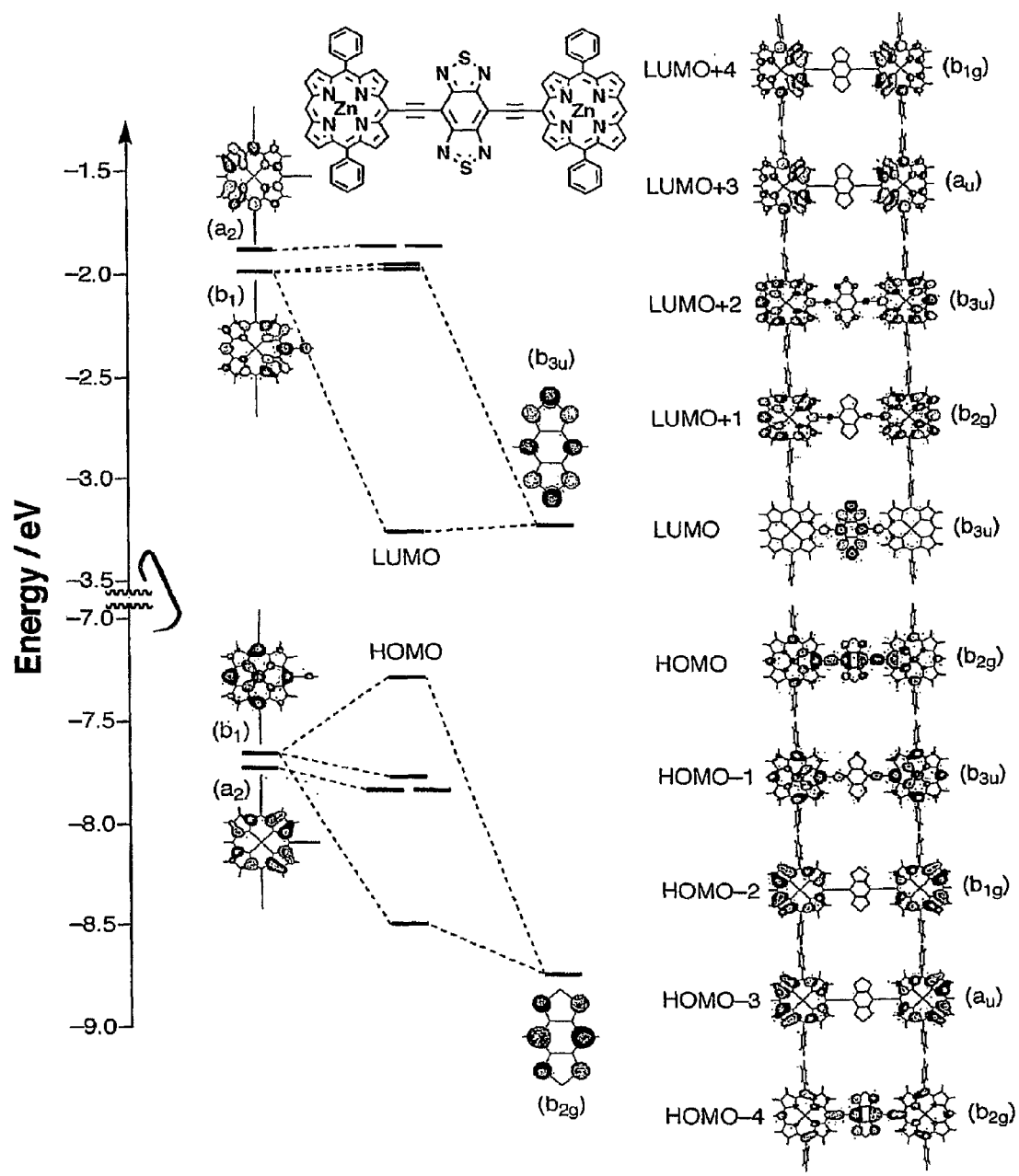
FIG. 8 shows frontier orbital correlation diagram for PZnE, benzobis(thiadiazole) (BBTD), and PZnE-BBTD-EPZn.
Figure 9:
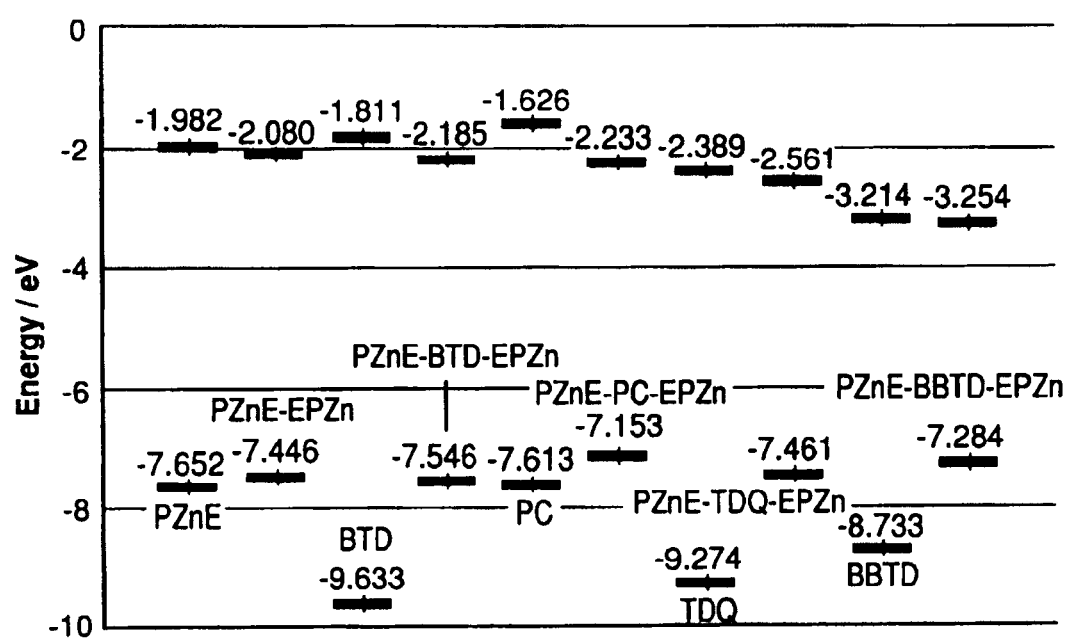
FIG. 9 shows diagrammatic representation of PZn-Sp-PZn and Sp HOMO and LUMO energy levels calculated using the PM3 semiempirical method.

Electronic Structure Calculations. Further insight into the electrooptic properties of these supermolecules can be garnered from an electronic structural analysis of PZn-Sp-PZn frontier orbitals (FOs) as a function of the intervening proquinoidal Sp moiety. FIGS. 4-8 display respectively the FOs of PZnE-EPZn, PZnE-BTD-EPZn, PZnE-PC-EPZn, PZnE-TDQ-EPZn, and PZnE-BBTD-EPZn. In these electronic structure calculations, geometry optimizations and semiempirical electronic structural calculations were performed using the PM3 method. Models for the PZn-Sp-PZn structures that featured planar macrocycles and Sp units constrained to lie in a common molecular plane, were utilized in the geometrical optimizations. PZn-Sp-PZn FOs presented in FIGS. 4-8 are depicted in an orbital correlation diagram format that shows the corresponding FOs and energies of their respective component PZnE and Sp building blocks. FIG. 9 displays the relative calculated HOMO and LUMO energies of all the FIG. 4-8 model compounds.

The FOs of PZnE-EPZn (FIG. 4) resemble those computed for meso-to-meso ethyne-bridged bis(PZn) (PZn-E-PZn) [Shediac, R.; Gray, M. H. B.; Uyeda, H. T.; Johnson, R. C; Hupp, J. T.; Angiolillo, P. J.; Therien, M. J. *J. Am. Chem. Soc.* 2000, 122, 7017-7033; Susumu, K.; Therien, M. J. *J. Am. Chem. Soc.* 2002, 124, 8550-8552; Beljonne, D.; O'Keefe, G. E.; Hamer, P. J.; Friend, R. H.; Anderson, H. L.; Brédas, J. L. *J. Chem. Phys.* 1997, 106, 9439-9460; Susumu, K.; Maruyama, H.; Kobayashi, H.; Tanaka, K. *J. Mater. Chem.* 2001, 11, 2262-2270]. (i) the HOMO exhibits substantial butadiyne-, $C_{meso}$-, and N-centered electron density, with the $C_{meso}$ carbons that constitute a portion of the conjugated macrocycle-to-macrocycle bridge displaying substantial π overlap with their respective $C_\alpha$ carbons; (ii) the LUMO manifests similarly comprehensive electronic derealization, exhibiting extensive cumulenic character along the $C_2$ axis defined by the butadiyne moiety. The evolution of FO electron density distributions in bis(porphyrin) compounds that feature a meso-to-meso linkage topology and a cylindrically α-symmetric bridge, relative to classic monomelic porphyrin building blocks, has been discussed in detail [see, Shediac, R.; Gray, M. H. B.; Uyeda, H. T.; Johnson, R. C; Hupp, J. T.; Angiolillo, P. J.; Therien, M. J. *J. Am. Chem. Soc.* 2000, 122, 7017-7033]. Note that both the PZnE-EPZn electron density distribution within the frontier orbital set, and the magnitude of the energy separation between these orbitals, are consistent with the x-polarized nature of its low lying electronically excited state. The PZnE-EPZn HOMO is 0.206 eV destabilized with respect to that of the PZnE benchmark, while its LUMO is 0.098 eV stabilized relative to this ethyne-elaborated monomer. This diminished computed HOMO-LUMO gap for PZnE-EPZn relative to PZnE is larger than that calculated for PZn-E-PZn, consistent with the expectation, and extensive spectroscopic evidence indicating, that interporphyryl electronic interactions diminish with increasing macrocycle-macrocycle distances.

An analogous computational study carried out on PZnE-BTD-EPZn evinces both a delocalized HOMO and LUMO (FIG. 5), similar to that noted for PZnE-EPZn. The PZnE-BTD-EPZn HOMO illustrates antibonding interactions between the PZn, ethyne, and BTD units that define the highly conjugated axis of the supermolecule, while the LUMO features an extensive degree of quinoidal character, with bonding interactions between the PZn-$C_{meso}$ and ethyne $C_\alpha$-carbon atoms, antibonding interactions between the ethyne $C_0$ and $C_\beta$ atoms, and bonding interactions between the ethyne $C_\beta$ and benzothiadiazole 4- and 7-carbon atoms. The HOMO energy level of PZnE-BTD-EPZn is destabilized by 0.106 eV relative to that of PZnE, while its LUMO energy level is stabilized by 0.203 eV with respect to this benchmark.

Figure 6:
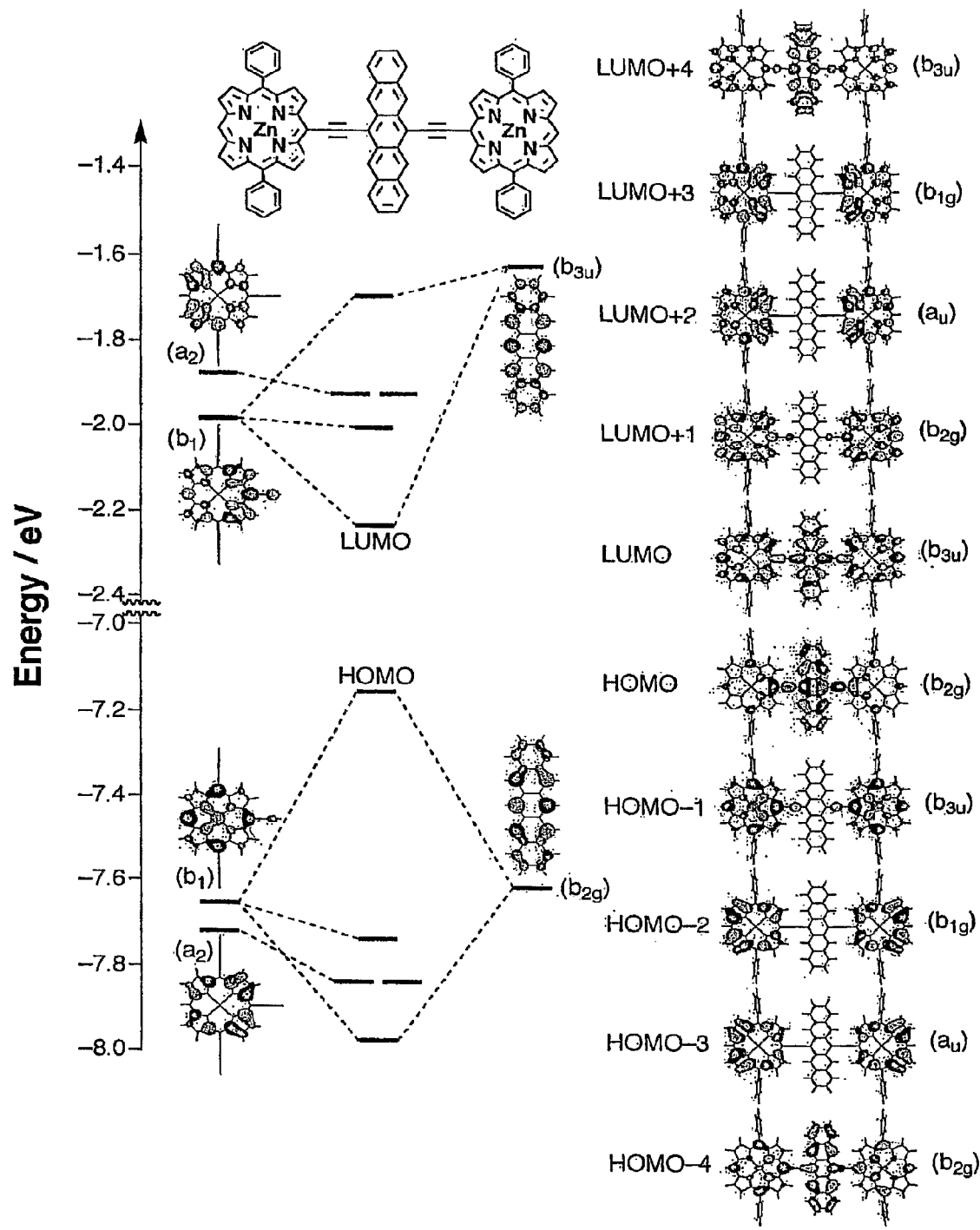
FIG. 6 shows frontier orbital correlation diagram for PZnE, pentacene (PC), and PZnE-PC-EPZn.

PZnE-PC-EPZn displays FO electron density distributions similar to that noted for PZnE-BTD-EPZn, with substantial electronic interactions evident between PZnE and PC Sp moieties in both the HOMO and LUMO (FIG. 6). The energy to which the PZnE-PC-EPZn HOMO is destabilized relative to PZnE (0.499 eV) has increased with respect to that observed for PZnE-BTD-EPZn; likewise, the PZnE-PC-EPZn LUMO is considerably more stabilized (0.251 eV, FIG. 9) than that computed for PZnE-BTD-EPZn. Note in this regard that both (i) large atomic orbital coefficients at the porphyrin meso- and pentacene 6,13-carbon positions in PZnE-PC-EPZn, and (ii) excellent energy matching within the PZnE and PC FO sets drive these substantial HOMO and LUMO energy level perturbations relative to that observed for the PZnE-BTD-EPZn case. The energy difference between the PZnE and Sp LUMOs increases as the Sp fragment LUMO energy levels become increasingly stabilized ($|E_{LUMO}(PZnE)-E_{LUMO}(Sp)|$=0171 (PZnE/BTD), 0.356 (PZnE/PC), 0.407 (PZnE/TDQ), 1.232 (PZnE/BBTD) eV; FIGS. 4-9). Given that the extent of the orbital interaction is inversely proportional to the energy difference between the interacting orbitals [Salzner, U. *J. Phys. Chem. B* 2002, 106, 9214-9220], this orbital energy mismatch attenuates the extent of LUMO delocalization in these PZn-Sp-PZn supermolecules, causing the LUMO becomes increasingly localized on the Sp unit. Thus, while contour plots of the PZnE-BTD-EPZn, PZnE-PC-EPZn, PZnE-TDQ-EPZn and PZnE-BBTD-EPZn HOMOs all show global delocalization, significant LUMO delocalization is evident only in PZnE-BTD-EPZn and PZnE-PC-EPZn (FIGS. 5 and 6), with PZnE-TDQ-EPZn and PZnE-BBTD-EPZn showing highly Sp-localized LUMOs (FIGS. 7 and 8). Note that the relative calculated HOMO and LUMO energy levels shown in FIG. 9 mirror the differences in the potentiometrically determined PZn-Sp-PZn HOMO and LUMO energy levels (FIG. 3). While these computational and electrochemical data underscore the cardinal role that PZnE and Sp fragment orbital energy differences play in fixing the radical cation and anion state energy levels in these PZn-Sp-PZn structures, it is important to appreciate that in contrast to many simple conjugated organic building blocks, whose low-lying excited states are described adequately by one-electron transitions, extensive configuration interaction (CI) is necessary to describe correctly porphyrin electronically excited states [Susumu, K.; Therien, M. J. *J. Am. Chem. Soc.* 2002, 124, 8550-8552 and Gouterman, M. In *The Porphyrins*; Dolphin, D., Ed.; Academic Press: London, 1978; Vol. III, p 1-165]. While absolute HOMO and LUMO energies largely determine $E_{1/2}^{0/+}$–$E_{1/2}^{-/0}$ values, large CI guarantees orbital contributions from multiple high-lying filled and low-lying empty levels for PZn-Sp-PZn electronically excited states. Such CI assures that the low-lying singlet of these species will possess both global derealization and extensive quinoidal character (vide infra).

Transient Optical Spectra of PZn-Sp-PZn Initially Prepared Electronically Excited Singlet States.

Figure 10:
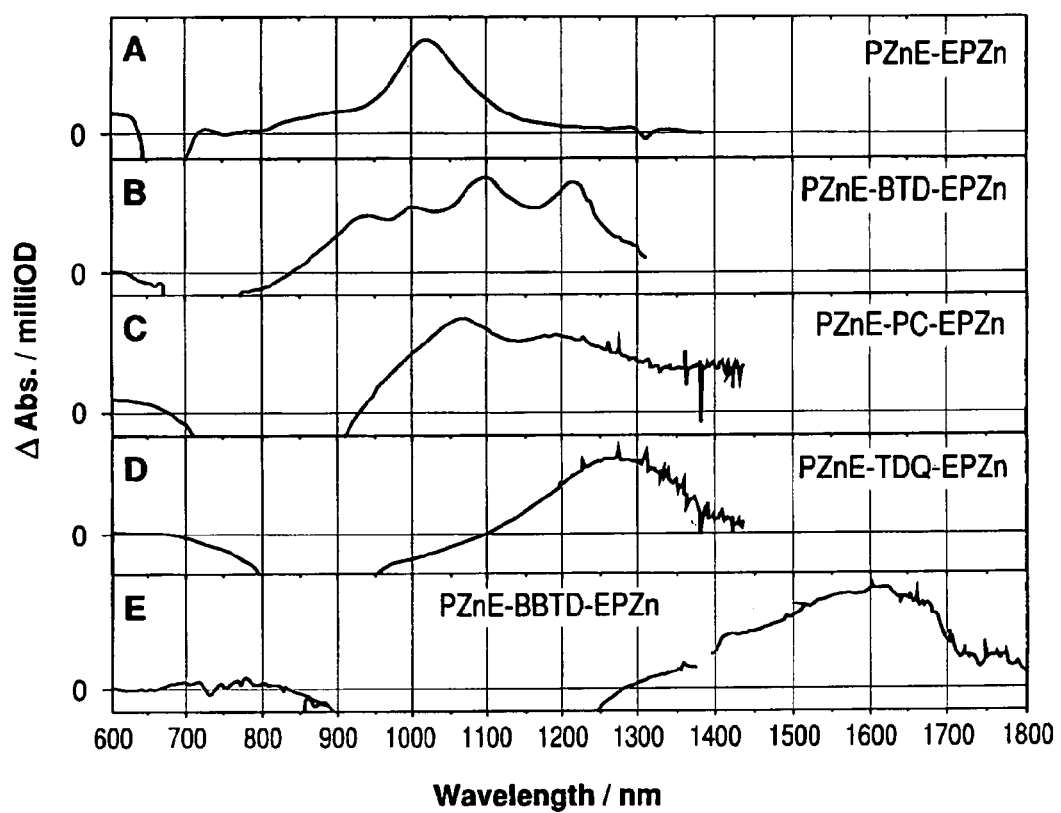
FIG. 10 shows scaled magic angle transient absorption spectra recorded for: (A) PZnE-EPZn, (B) PZnE-BTD-EPZn, (C) PZnE-PC-EPZn, (D) PZnE-TDQ-EPZn, and (E) PZnE-BBTD-EPZn measured at delay times of 300 fs. Experimental conditions: solvent=THF; T=25° C.; $\lambda_{ex}$=655 nm (A), 662 nm (B), 775 nm (C), 775 nm (D), and 650 nm (E).

The combination of steady-state electronic absorption, potentiometric, and computational data, coupled with the expectation that substantial CI drives global electronic derealization in electronically excited PZn-Sp-PZn species, suggests that quinoidal resonance contributions to $S_1$-$S_n$ states exceed that for the corresponding ground ($S_0$) states. Pump-probe transient absorption spectroscopic experiments that interrogate the $S_1$-$S_n$ transition manifolds of these supermolecules further support this view. FIG. 10 shows transient absorption spectra recorded at 300 fs time delay for PZnE-EPZn, PZnE-BTD-EPZn, PZnE-PC-EPZn, PZnE-TDQ-EPZn and PZnE-BBTD-EPZn) in the NIR spectral region.

Qualitatively, these $S_1$-$S_n$ spectra bear many features in common with those previously delineated for meso-to-meso ethyne-bridged bis[(porphinato)zinc(II)] (PZn-E-PZn) structures [Rubtsov, I. V.; Susumu, K.; Rubtsov, G. I.; Therien, M. J. *J. Am. Chem. Soc.* 2003, 125, 2687-2696]. Like PZn-E-PZn species, PZn-Sp-PZn supermolecules display intense NIR $S_1$-$S_n$ transitions; these absorptions possess integrated oscillator strengths of comparable magnitude to their corresponding B- and Q-state manifold bleaching transitions. While the benchmark PZnE-EPZn transient absorption spectrum (FIG. 10A) bears features closely aligned with that reported for PZn-E-PZn chromophores (bis[(5,5'-10,20-bis[3,5-bis(3,3-dimethyl-1-butyloxy)phenyl]porphinato)zinc(II)]ethyne and [(5,-10,20-bis[3,5-bis(3,3-dimethyl-1-butyloxy)phenyl]por-phinato)zinc(II)]-[(5',-15'-ethynyl-10',20'-bis[10,20-bis (heptafluoropropyl)porphinato)zinc(II)]ethyne), PZnE-BTD-EPZn, PZnE-PC-EPZn, PZnE-TDQ-EPZn and PZnE-BBTD-EPZn manifest $S_1$>$S_n$ absorption manifolds that shift to progressively lower energies (FIG. 10B-E), tracking with expectations based on the relative frontier orbital energy levels of these supermolecules determined by potentiometric and computational methods (vide supra).

The wavelength of the most intense transition within the NIR absorption manifold [$\lambda_{max}(S_1$->$S_n)$] for PZnE-BTD-EPZn, PZnE-PC-EPZn, PZnE-TDQ-EPZn and PZnE-BBTD-EPZn occurs at 1207, ~1187, 1270 and 1610 nm, respectively, 1700-3800 cm$^{-1}$ red-shifted from the analogous $\lambda_{max}(S_1$->$S_n)$ determined for PZnE-EPZn (~1000 nm). Note that the corresponding FWHM values for the $S_1$-$S_n$ manifolds of these PZn-Sp-PZn species [Compound, (FWHM): PZnE-BTD-EPZn (~2800 cm$^{-1}$), PZnE-PC-EPZn (>2500 cm$^{-1}$), PZnE-TDQ-EPZn ($\geq$1160 cm$^{-1}$) and PZnE-BBTD-EPZn ($\geq$1150 cm$^{-1}$)] determined at 300 fs following optical excitation, meet or exceed that evinced for PZnE-EPZn (1100 cm$^{-1}$).

Further, the FIG. 10B-E spectra bear absorptive signatures that indicate that the nature of the proquinoidal bridge plays a pivotal role in determining the degree of excited-state conjugation and the extent to which nuclear relaxation dynamics impact the early-time evolution of the excited state. As a case in point, note that while sharp differences exist between the $S_0$->$S_1$ absorption manifolds of PZnE-BTD-EPZn and PZnE-PC-EPZn (FIG. 2), the low energy excited states for these species present 300 fs following optical excitation are similar, with significant NIR-absorptive spectral breadths and substantial $S_1$->$S_n$ absorptive oscillator strengths at wavelengths longer than 1300 nm. In this regard, we underscore that there are relatively few examples of electronically excited chromophoric singlet states that absorb strongly in the NIR; systems that possess such singlet excited-state manifold absorptive properties are largely confined to a select group of semi-conducting π-conjugated polymers. See, Moraes, F.; Schaffer, H.; Kobayashi, M.; Heeger, A. J.; Wudl, F. *Phys. Rev. B* 1984, 30, 2948-2950; Woo, H. S.; Graham, S. C; Halliday, D. A.; Bradley, D. D. C.; Friend, R. H.; Burn, P. L.; Holmes, A. B. *Phys. Rev. B* 1992, 46, 7379-7389; Lanzani, G.; Nisoli, M.; De Silvestri, S.; Barbarella, G.; Zambianchi, M.; Tubino, R. *Phys. Rev. B* 1996, 53, 4453-4457; Frolov, S. V.; Liess, M.; Lane, P. A.; Gellermann, W.; Vardeny, Z. V.; Ozaki, M.; Yoshino, K. *Phys. Rev. Lett.* 1997, 78, 4285-4288; Kraabel, B.; Klimov, V. I.; Kohlman, R.; Xu, S.; Wang, H.-L.; McBranch, D. W. *Phys. Rev. B* 2000, 61, 8501-8515; Kraabel, B.; McBranch, D. W. *Chem. Phys. Lett.* 2000, 330, 403-409; Jiang, X. M.; Österbacka, R.; Korovyanko, O.; An, C. P.; Horovitz, B.; Janssen, R. A. J.; Vardeny, Z. V. *Adv. Fund. Mater.* 2002, 12, 587-597.

EXAMPLES

Example 1

4,7-Bis[(trimethylsilyl)ethynyl]benzo[c][1,2,5]thiadiazole 4,7-Dibromobenzo[c][1,2,5]thiadiazole (1.02 g, $3.47 \times 10^{-3}$ mol), Pd(PPh$_3$)$_4$ (0.207 g, $1.79 \times 10^{-4}$ mol), CuI (0.029 g, $1.5 \times 10^{-4}$ mol), THF (30 ml), diethylamine (3.0 ml) and (trimethylsilyl)acetylene (6.00 ml, $4.25 \times 10^{-2}$ mol) were added to a 100-ml Schlenk tube. N$_2$ was bubbled through the mixture for 5 min, following which the reaction was stirred at 45° C. for 20 h under N$_2$. After cooling, the solvent was evaporated and the residue was chromatographed on silica gel with 1:1 hexanes:CHCl$_3$ as the eluant. Yield=1.05 g (92% based on 1.02 g of 4,7-dibromobenzothiadiazole). $^1$H NMR (360 MHz, CDCl$_3$): δ 7.70 (s, 2H, Ph-H), 0.33 (s, 18H, —Si—CH$_3$). Chemical Ionization MS m/z: 328.0880 (M$^+$) (calcd 328.089).

Example 2

4,9-Dibromo-6,7-dimethyl[1,2,5]thiadiazolo[3,4-g]quinoxaline 5,6-Diamino-4,7-dibromobenzo[c][1,2,5]thiadiazole (0.257 g, $7.93 \times 10^{-4}$ mol) was dissolved in acetic acid (30 ml). 2,3-Butanedione (0.30 ml, $3.4 \times 10^{-3}$ mol) was added, and the reaction mixture was stirred for 19 h at room temperature under N$_2$. Water (50 ml) was added, and the resulting precipitate was filtered, dissolved in CH$_2$Cl$_2$, washed with water, and dried over Na$_2$SO$_4$. After the solvent was evaporated, the residue was chromatographed on silica gel with CHCl$_3$. Yield=0.256 g (86% based on 0.257 g of 5,6-diamino-4,7-dibromobenzo[c][1,2,5]thiadiazole). $^1$H NMR (360 MHz, CDCl$_3$): δ 2.88 (s, 6H, —CH$_3$). Chemical Ionization MS m/z: 371.8675 (M$^+$) (calcd 371.868).

Example 3

6,7-Dimethyl-4,9-bis[(trimethylsilyl)ethynyl][1,2,5]thiadiazolo[3,4-g]quinoxaline 4,9-Dibromo-6,7-dimethyl[1,2,5]thiadiazolo[3,4-g]quinoxaline (68.0 mg, $1.82 \times 10^{-4}$ mol), Pd$_2$dba$_3$ (36.0 mg, $3.93 \times 10^{-5}$ mol), AsPh$_3$ (62.2 mg, $2.03 \times 10^{-4}$ mol), (trimethylsilyl)acetylene (0.60 ml, $4.2 \times 10^{-3}$ mol), Et$_3$N (2.0 ml), and THF (15 ml) were added to a 100-ml Schlenk tube. The reaction mixture was stirred at 45° C. for 18.5 h under N$_2$. After the solvent was evaporated, the residue was chromatographed on silica gel using 8:1 hexanes:THF as the eluant. Yield=0.051 g (69% based on 68.0 mg of 4,9-dibromo-6,7-dimethyl[1,2,5]thiadiazolo[3,4-g]quinoxaline). $^1$H NMR (360 MHz, CDCl$_3$): δ 2.83 (s, 6H, —CH$_3$), 0.42 (s, 18H, —Si—CH$_3$). Chemical Ionization MS m/z: 408.1264 (M$^+$) (calcd 408.126).

Example 4

4,8-Bis[(trimethylsilyl)ethynyl]benzo[1,2-c:4,5-c']bis([1,2,5]thiadiazole)

4,8-Dibromobenzo[1,2-c:4,5-c']bis([1,2,5]thiadiazole) (0.049 g, $1.4 \times 10^{-4}$ mol), Pd$_2$dba$_3$ (0.015 g, $1.6 \times 10^{-5}$ mol), AsPh$_3$ (0.044 g, $1.8 \times 10^{-3}$ mol), (trimethylsilyl)acetylene (0.25 ml, $1.8 \times 10^{-3}$ mol), Et$_3$N (2.0 ml), and THF (30 ml) were added to a 100-ml Schlenk tube. The reaction mixture was stirred at 45° C. for 10.5 h under N$_2$. After the solvent was evaporated, the residue was chromatographed on silica gel using 8:1 hexanes:THF as the eluant. The product was further purified by size exclusion column chromatography (BioRad Bio-Beads SX-3 packed in THF, gravity flow). Yield=0.020 g (37% based on 0.049 g of 4,8-dibromobenzo[1,2-c:4,5-c']bis([1,2,5]thiadiazole)). $^1$H NMR (360 MHz, CDCl$_3$): δ 0.42 (s, 18H, —Si—CH$_3$). Chemical Ionization MS m/z: 386.0508 (M$^+$) (calcd for 386.051).

Example 5

(5-Iodo-10,20-bis[2',6'-bis(3,3-dimethyl-1-butyloxy)phenyl]porphinato)zinc(II)

5,10-Bis[2',6'-bis(3,3-dimethyl-1-butyloxy)phenyl]porphinato)zinc(II) (0.322 g, $3.48 \times 10^{-4}$ mol) and iodine (0.089 g, $3.5 \times 10^{-4}$ mol) were dissolved in CHCl$_3$ (50 ml) and pyridine (1 ml). AgPF$_6$ (0.089 g, $3.5 \times 10^{-4}$ mol) was added, and the reaction mixture was stirred at room temperature for 20 min, and filtered. After the solvent was evaporated, the residue was chromatographed on silica gel using 2:1 CHCl$_3$:hexanes as the eluant. Yield 0.247 g (67% based on 0.322 g of the porphyrin starting material). $^1$H NMR (360 MHz, CDCl$_3$): δ 10.09 (s, 1H, meso-H), 9.73 (d, 2H, J=4.7 Hz, β-H), 9.26 (d, 2H, J=4.3 Hz, β-H), 8.96 (d, 2H, J=4.7 Hz, β-H), 8.93 (d, 2H, J=4.7 Hz, β-H), 7.72 (t, 2H, J=8.4 Hz, Ph-H), 7.01 (d, 4H, J=8.6 Hz, Ph-H), 3.90 (t, 8H, J=7.2 Hz, —O—CH$_2$—C), 0.83 (t, 8H, J=7.2 Hz, —O—C—CH$_2$—C), 0.22 (s, 36H, —C—CH$_3$). ESI MS m/z: 1050.3503 (M$^+$) (calcd for 1050.346).

Example 6

4,7-Bis[(10,20-bis[2',6'-bis(3,3-dimethyl-1-butyloxy)phenyl]porphinato)zinc(II)-5-ylethynyl]benzo[c][1,2,5]thiadiazole (PZnE-BTD-EPZn)

(5-Iodo-10,20-bis[2',6'-bis(3,3-dimethyl-1-butyloxy)phenyl]porphinato)zinc(II) (0.106 g, $1.01 \times 10^{-4}$ mol), 4,7-bis(trimethylethynyl)benzo[c][1,2,5]thiadiazole (0.032 g, $9.7 \times 10^{-5}$ mol), Pd(PPh$_3$)$_4$ (22.0 mg, $1.90 \times 10^{-5}$ mol), CuI (7.0 mg, $3.7 \times 10^{-5}$ mol), K$_2$CO$_3$ (0.104 g, $7.52 \times 10^{-4}$ mol), THF (25 ml), MeOH (4.0 ml), and Et$_3$N (2.0 ml) were added to a 100-ml Schlenk tube. The reaction mixture was stirred at 40° C. for 6 h under N$_2$. After the solvent was evaporated, the residue was chromatographed on silica gel using 5:1 hexanes:THF as the eluant. The product was further purified by size exclusion column chromatography (BioRad Bio-Beads SX-1 packed in THF, gravity flow). Yield=0.048 g (47% based on 0.106 g of the porphyrin starting material). $^1$H NMR (360 MHz, CDCl$_3$): δ 10.17 (d, 4H, J=4.7 Hz, β-H), 10.08 (s, 2H, meso-H), 9.25 (d, 4H, J=4.1 Hz, β-H), 9.09 (d, 4H, J=4.2 Hz, β-H), 8.95 (d, 4H, J=4.6 Hz, □-H), 8.41 (s, 2H, Ph-H), 7.75 (t, 4H, J=8.4 Hz, Ph-H), 7.05 (d, 8H, J=8.6 Hz, Ph-H), 3.94 (t, 16H, J=7.3 Hz, —O—CH$_2$—C), 0.89 (t, 16H, J=7.6 Hz, —O—C—CH$_2$—C), 0.25 (s, 72H, —C—CH$_3$). MALDI-TOF MS m/z: 2029.98 (M$^+$) (calcd 2028.884).

Example 7

6,13-Bis[(10,20-bis[2',6'-bis(3,3-dimethyl-1-butyloxy)phenyl]porphinato)zinc(II)-5-ylethynyl]pentacene (PZnE-PC-EPZn)

(5-Bromo-10,20-bis[2',6'-bis(3,3-dimethyl-1-butyloxy)phenyl]porphinato)zinc(II) (0.080 g, 8.0×10$^{-5}$ mol), 6,13-bis[(trimethylsilyl)ethynyl]pentacene (19.2 mg, 4.08×10$^{-5}$ mol), Pd$_2$dba$_3$ (11 mg, 1.2×10$^{-5}$ mol), AsPh$_3$ (26 mg, 8.6×10$^{-5}$ mol), K$_2$CO$_3$ (0.082 g, 5.9×10$^{-4}$ mol), THF (25 ml), MeOH (4.0 ml), and Et$_3$N (2.0 ml) were added to a 100-ml Schlenk tube. The reaction mixture was stirred at 50° C. for 25.5 h under N$_2$. After the solvent was evaporated, the residue was chromatographed on silica gel with 5:1 hexanes:THF as the eluant. The product was further purified by size exclusion column chromatography (BioRad Bio-Beads SX-1 packed in THF, gravity flow). Yield=0.039 g (45% based on 0.080 g of the porphyrin starting material). $^1$H NMR (360 MHz, 1 drop pyridine-d$_5$ in CDCl$_3$): δ 10.28 (d, 4H, J=4.6 Hz, β-H), 10.24 (s, 4H, Ph-H), 9.92 (s, 2H, meso-H), 9.15 (d, 4H, J=4.5 Hz, β-H), 9.11 (d, 4H, J=4.6 Hz, β-H), 8.88 (d, 4H, J=4.3 Hz, β-H), 8.37 (dd, 4H, J=6.4 and 3.0 Hz, Ph-H), 7.77 (t, 4H, J=8.4 Hz, Ph-H), 7.55 (dd, 4H, J=6.4 and 3.0 Hz, Ph-H), 7.10 (d, 8H, J=8.3 Hz, Ph-H), 3.98 (m, 16H, —O—CH$_2$—C), 0.88 (t, 16H, J=6.9 Hz, —O—C—CH$_2$—C), 0.40 (s, 72H, —C—CH$_3$). MALDI-TOF MS m/z: 2170.62 (M$^+$) (calcd 2170.984).

Example 8

4,9-Bis[(10,20-bis[2',6'-bis(3,3-dimethyl-1-butyloxy)phenyl]porphinato)zinc(II)-5-ylethynyl]-6,7-dimethyl[1,2,5]thiadiazolo[3,4-g]quinoxaline (PZnE-TDQ-EPZn)

(5-Ethynyl-10,20-bis[2',6'-bis(3,3-dimethyl-1-butyloxy)phenyl]porphinato)zinc(II) (94.7 mg, 9.96×10$^{-5}$ mol), 4,9-dibromo-6,7-dimethyl[1,2,5]thiadiazolo[3,4-g]quinoxaline (24.1 mg, 6.44×10$^{-5}$ mol), Pd$_2$dba$_3$ (20.6 mg, 2.25×10$^{-5}$ mol), AsPh$_3$ (32.0 mg, 1.04×10$^{-4}$ mol) were added to a 100-ml Schlenk tube and degassed. THF (30 ml) and Et$_3$N (2.0 ml) were added under N$_2$, and the reaction mixture was stirred at 45° C. for 21 h. After the solvent was evaporated, the residue was chromatographed on silica gel using 5:1 hexanes:THF as the eluant. The product was further purified by size exclusion column chromatography (BioRad Bio-Beads SX-1 packed in THF, gravity flow). Yield=0.044 g (42% based on 94.7 mg of the porphyrin starting material).

$^1$H NMR (360 MHz, CDCl$_3$): δ 10.52 (d, 4H, J=4.6 Hz, β-H), 10.03 (s, 2H, meso-H), 9.21 (d, 4H, J=4.5 Hz, Ph-H), 9.09 (d, 4H, J=4.6 Hz, β-H), 8.90 (d, 4H, J=4.5 Hz, β-H), 7.76 (t, 4H, J=8.4 Hz, Ph-H), 7.06 (d, 8H, J=8.5 Hz, Ph-H), 3.95 (t, 16H, J=7.3 Hz, —O—CH$_2$—C), 3.31 (s, 6H, —CH$_3$), 0.88 (t, 16H, J=6.6 Hz, —O—C—CH$_2$—C), 0.29 (s, 72H, —C—CH$_3$). MALDI-TOF MS m/z: 2110.64 (M$^+$) (calcd 2108.922).

Example 9

4,8-Bis[(10,20-bis[2',6'-bis(3,3-dimethyl-1-butyloxy)phenyl]porphinato)zinc(II)-5-ylethynyl]benzo[1,2-c:4,5-c'][1,2,5]bis([1,2,5]thiadiazole) (PZnE-BBTD-EPZn)

(5-Ethynyl-10,20-bis[2',6'-bis(3,3-dimethyl-1-butyloxy)phenyl]porphinato)zinc(II) (56.5 mg, 5.94×10$^{-5}$ mol), 4,8-dibromobenzo[1,2-c:4,5-c']bis([1,2,5]thiadiazole) (19.3 mg, 5.48×10$^{-5}$ mol), Pd(PhCN)$_2$Cl$_2$ (6.7 mg, 1.7×10$^{-5}$ mol), CuI (3.5 mg, 1.8×10$^{-5}$ mol) were added to a 50-ml Schlenk tube and degassed. THF (20 ml), P(f-Bu)$_3$ (10 wt % solution in hexanes, 0.12 ml, 3.9×10$^{-5}$ mol), and diisopropylamine (0.20 ml, 1.4×10$^{-3}$ mol) were added under N$_2$, and the reaction mixture was stirred at 45° C. for 25 h. After the solvent was evaporated, the residue was chromatographed on silica gel using 8:1 hexanes:THF as the eluant. Yield=0.025 g (40% based on 56.5 mg of the porphyrin starting material). $^1$H NMR (360 MHz, CDCl$_3$): δ 10.36 (d, 4H, J=4.9 Hz, β-H), 10.01 (s, 2H, meso-H), 9.19 (d, 4H, J=4.4 Hz, Ph-H), 9.09 (d, 4H, J=4.6 Hz, β-H), 8.89 (d, 4H, J=4.4 Hz, β-H), 7.75 (t, 4H, J=8.4 Hz, Ph-H), 7.05 (d, 8H, J=8.6 Hz, Ph-H), 3.95 (t, 16H, J=7.3 Hz, —O—CH$_2$—C), 0.89 (t, 16H, J=7.3 Hz, —O—C—CH$_2$—C), 0.30 (s, 72H, —C—CH$_3$). MALDI-TOF MS m/z: 2086.77 (M$^+$) (calcd 2086.847).

Example 10

3,7-Dimethyloctyl bromide

To a solution of 3,7-dimethyl-1-octanol (50.0 ml, 0.264 mol) and triphenylphosphine (86.9 g, 0.331 mol) in 300 ml of CH$_2$Cl$_2$ were added N-bromosuccinimide (56.6 g, 0.318 mol) in portions at 0° C. After stirring at 0° C. for 2 h, the solvent was evaporated. The residue was treated with hexane and filtered. The solids were washed thoroughly with hexane and the combined hexane extracts evaporated. The residue was chromatographed on silica gel with hexane. Yield=54.13 g (93% based on 50.0 ml of 3,7-dimethyl-1-octanol). $^1$H NMR (360 MHz, CDCl$_3$): δ 3.37-3.50 (m, 2H, —CH$_2$Br), 1.07-1.94 (m, 10H, (CH$_3$)$_2$CHCH$_2$CH$_2$CH$_2$CH(CH$_3$)CH$_2$CH$_2$Br), 0.89 (d, 3H, J=6.5 Hz, —CH$_3$), 0.87 (d, 6H, J=6.8 Hz, —CH$_3$). CI MS m/z: 220.048 (M$^+$) (calcd 220.083).

Example 11

2,6,13,17-Tetramethyloctadecane-9,10-dione

To a suspension of 1,4-dimethylpiperazine-2,3-dione (2.08 g, 1.46×10$^{-2}$ mol) in 50 ml of dry Et$_2$O was added 3,7-dimethyloctyl lithium (0.45M solution in Et$_2$O, 65 ml, 2.9×10$^{-2}$ mol, freshly prepared from 3,7-dimethyloctyl bromide and lithium) by a syringe. After 40 min of stirring at room temperature under N$_2$, the solution was hydrolyzed with 100 ml of 10% HCl and extracted with CHCl$_3$. The combined organic layers were washed with saturated aqueous NaHCO$_3$ and dried over Na$_2$SO$_4$. The product was chromatographed on silica gel with 3:1 hexane:CHCl$_3$ as the eluent. Yield=4.446 g (91% based on 65 ml of 0.45M 3,7-dimethyloctyl lithium in Et$_2$O). $^1$H NMR (250 MHz, CDCl$_3$): δ 2.69-2.78 (m, 4H, —CH$_2$CO), 1.06-1.65 (m, 20H, (CH$_3$)$_2$CHCH$_2$CH$_2$CH$_2$CH(CH$_3$)CH$_2$CH$_2$CO), 0.87 (d, 6H, J=9.0 Hz, —CH$_3$), 0.86 (d, 12H, J=9.5 Hz, —CH$_3$). CI MS m/z: 338.3175 (M$^+$) (calcd 338.318).

Example 12

4,9-Dibromo-6,7-bis(3',7'-dimethyloctyl)[1,2,5]thiadiazolo[3,4-g]quinoxaline 5,6-Diamino-4,7-dibromobenzo[c][1,2,5]thiadiazole (0.224 g, 6.91×10$^{-4}$ mol) was dissolved in acetic acid (40 ml). 2,6,13,17-Tetramethyloctadecane-9,10-dione (0.261 g, 7.71×10$^{-4}$ mol) was added, and the reaction mixture was stirred for 71 h at room temperature under $N_2$. After the solvent was evaporated, water was added, and the mixture was extracted with $CHCl_3$. The combined organic layers were washed with water, aq. $NaHCO_3$ and dried over $Na_2SO_4$. After the solvent was evaporated, the residue was chromatographed on silica gel with $CHCl_3$ and further purified by size exclusion column chromatography (BioRad Bio-Beads SX-1 packed in THF, gravity flow). Yield=0.360 g (83% based on 0.224 g of 5,6-diamino-4,7-dibromobenzo[c][1,2,5]thiadiazole). $^1H$ NMR (250 MHz, $CDCl_3$): δ 3.01-3.22 (m, 4H, Ar—$CH_2$), 1.11-2.09 (m, 20H, $(CH_3)_2CHCH_2$ $CH_2CH_2CH$ $(CH_3)CH_2CH_2Ar$), 1.03 (d, 6H, J=6.5 Hz, —$CH_3$), 0.88 (d, 12H, J=6.6 Hz, —$CH_3$). CI MS m/z: 625.157 ((M+H)$^+$) (calcd 625.158).

Example 13

4-(1-Dodecyloxy)Iodobenzene

4-Iodophenol (3.03 g, $1.38 \times 10^{-2}$ mol), 1-bromododecane (6.65 ml, $2.77 \times 10^{-2}$ mol) and $K_2CO_3$ (3.81 g, $2.76 \times 10^{-2}$ mol) were dissolved in 50 ml of dry DMF and refluxed for 3.5 h under $N_2$. After cooling, the solution was diluted with water, 2M HCl, and extracted with $CH_2Cl_2$. The combined organic layers were washed with saturated aq. $NaHCO_3$, water, and dried over $Na_2SO_4$. The product was chromatographed on silica gel with 3:1 hexane:$CHCl_3$ as the eluent. Yield=5.274 g (98% based on 3.03 g of 4-iodophenol). $^1H$ NMR (250 MHz, $CDCl_3$): δ 7.53 (d, 2H, J=8.8 Hz, Ph), 6.67 (d, 2H, J=9.0 Hz, Ph), 3.90 (t, 2H, J=6.5 Hz, —$OCH_2$—), 1.76 (quint, 2H, J=6.6 Hz, —$OCH_2CH_2$—), 1.13-1.48 (m, 18H, —$CH_2$—), 0.88 (t, 3H, J=6.4 Hz, —$CH_3$). CI MS m/z: 388.125 (M$^+$) (calcd 388.126).

Example 14

4-Dodecyloxy[(trimethylsilyl)ethynyl]benzene 4-(Dodecyloxy)iodobenzene (4.04 g, $1.04 \times 10^{-2}$ mol), triphenylphosphine (0.165 g, $6.29 \times 10^{-4}$ mol), CuI (0.108 g, $5.67 \times 10^{-4}$ mol) and $Pd(PPh_3)_2Cl_2$ (0.153 g, $2.18 \times 10^{-4}$ mol) were dissolved in 40 ml of dry piperidine under $N_2$. (Trimethylsilyl)acetylene (3.00 ml, $2.12 \times 10^{-2}$ mol) was added and the mixture was stirred at 50° C. for 6 h under $N_2$. After cooling, the reaction mixture was poured into aq. $NH_4Cl$ and extracted with $CH_2Cl_2$ (three times). The combined organic layers were washed with aq. $NH_4Cl$, water, and dried over $Na_2SO_4$. The crude product was chromatographed on silica gel with 4:1 hexane:$CH_2Cl_2$ as the eluent. Yield=3.633 g (97% based on 4.04 g of 4-(dodecyloxy)iodobenzene). $^1H$ NMR (250 MHz, $CDCl_3$): δ 7.39 (d, 2H, J=8.9 Hz, Ph), 6.80 (d, 2H, J=9.0 Hz, Ph), 3.94 (t, 2H, J=6.6 Hz, —$OCH_2$—), 1.77 (quint, 2H, J=6.6 Hz, —$OCH_2CH_2$—), 1.17-1.50 (m, 18H, —$CH_2$—), 0.88 (t, 3H, J=6.6 Hz, —$CH_3$), 0.24 (s, 9H, Si—$CH_3$). CI MS m/z: 358.268 (M$^+$) (calcd 358.269).

Example 15

4-Dodecyloxyethynylbenzene

4-Dodecyloxy[(trimethylsilyl)ethynyl]benzene (3.09 g, $8.62 \times 10^{-3}$ mol) was dissolved in a mixture of 20 ml of MeOH and 20 ml of THF. 5N NaOH (2.1 ml, $1.05 \times 10^{-2}$ mol) was added and the solution was stirred for 3.5 h at room temperature under $N_2$. Water was added to the reaction mixture. The aqueous layer was extracted three times with $CH_2Cl_2$. The combined organic layers were dried over $MgSO_4$. The product was chromatographed on silica gel with 4:1 hexane:$CH_2Cl_2$ as the eluent. Yield=2.430 g (98% based on 3.09 g of 4-dodecyloxy[(trimethylsilyl)ethynyl]benzene). $^1H$ NMR (250 MHz, $CDCl_3$): δ 7.41 (d, 2H, J=8.8 Hz, Ph), 6.83 (d, 2H, J=8.7 Hz, Ph), 3.95 (t, 2H, J=6.6 Hz, —$OCH_2$—), 2.99 (s, 1H, ethynyl-H), 1.78 (quint, 2H, J=6.9 Hz, —$OCH_2CH_2$—), 1.10-1.51 (m, 18H, —$CH_2$—), 0.88 (t, 3H, J=6.6 Hz, —$CH_3$). CI MS m/z: 287.236 ((M+H)$^+$) (calcd 287.237).

Example 16

4,9-bis[(4'-dodecyloxy)phenylethynyl]-6,7-bis(3',7'-dimethyloctyl)[1,2,5]thiadiazolo[3,4-g]quinoxaline 4,9-Dibromo-6,7-bis(3',7'-dimethyloctyl)[1,2,5]thiadiazolo[3,4-g]quinoxaline (82.3 mg, $1.31 \times 10^{-4}$ mol), 4-dodecyloxyethynylbenzene (50.0 mg, $1.7 \times 10^{-4}$ mol), $Pd_2dba_3$ (25.4 mg, $2.77 \times 10^{-5}$ mol), $AsPh_3$ (60.4 mg, $1.97 \times 10^{-4}$ mol) and dry THF (10 ml) were added to a 100-ml round-bottom flask. Ar was bubbled into the reaction mixture for 5 min before i-$Pr_2NH$ (0.50 ml) was added. The reaction mixture was stirred at 40° C. for 37 h under Ar. After the solvent was evaporated, the residue was chromatographed on silica gel with 2:3 hexane:$CHCl_3$ as the eluent. Yield=0.037 g (42% based on 50 mg of 4-dodecyloxyethynylbenzene). $^1H$ NMR (250 MHz, $CDCl_3$): δ 7.74 (d, 4H, J=8.8 Hz, Ph), 6.94 (d, 4H, J=8.9 Hz, Ph), 4.01 (t, 4H, J=6.6 Hz, —$OCH_2$—), 3.00-3.23 (m, 4H, Ar—$CH_2$), 1.1-2.2 (m, 60H, —$CH_2$—), 1.06 (d, 6H, J=6.6 Hz, —$CH_2$—), 0.89 (t, 6H, J=6.6 Hz, —$CH_3$), 0.86 (d, 12H, J=6.6 Hz, —$CH_3$). MALDI-TOF MS m/z: 1037.7 (M$^+$) (calcd 1036.757).

Example 17

4-Iodo-N,N-dihexylaniline

4-Iodoaniline (15.05 g, $6.87 \times 10^{-2}$ mol), $K_2CO_3$ (19.00 g, 0.137 mol), 1-iodohexane (32.0 ml, 0.217 mol) and dry DMF (170 ml) were added to a 500-ml two-neck round-bottom flask. Ar was bubbled into the reaction mixture for 10 min. The reaction mixture was stirred at 90° C. for 16 h and at 100° C. for 2.5 h under Ar. After cooling, the reaction mixture was filtered to remove inorganic solids. Solvents were removed in vacuo, and water was added to the reaction mixture. The organic layers were extracted with $CHCl_3$, washed with aq. $NaHCO_3$ and water, and dried over $Na_2SO_4$. The residue was chromatographed on silica gel 4:1 hexane:$CHCl_3$ as the eluent. Yield=20.47 g (77% based on 15.05 g of 4-iodoaniline). $^1H$ NMR (250 MHz, $CDCl_3$): δ 7.41 (d, 2H, J=8.8 Hz, Ph), 6.40 (d, 2H, J=9.1 Hz, Ph), 3.20 (t, 4H, J=7.6 Hz, —$NCH_2$—), 1.43-1.61 (m, 4H, —$NCH_2CH_2$—), 1.18-1.37 (m, 12H, —$CH_2$—), 0.89 (t, 6H, J=6.5 Hz, —$CH_3$). CI MS m/z: 388.149 ((M+H)$^+$) (calcd 388.150).

Example 18

4-[(Trimethylsilyl)ethynyl]-N,N-dihexylaniline

4-Iodo-N,N-dihexylaniline (3.150 g, $8.13 \times 10^{-3}$ mol), $Pd(PPh_3)_2Cl_2$ (0.332 g, $4.73 \times 10^{-4}$ mol), CuI (0.130 g, $6.83 \times 10^{-4}$ mol) and $Et_3N$ (20 ml) were added to a 100-ml round-bottom flask. Ar was bubbled into the reaction mixture for 5 min before (trimethylsilyl)acetylene (2.40 ml, $1.70 \times 10^{-2}$ mol) was added. The reaction mixture was stirred at 45° C. for 18 h under Ar. After the solvent was removed in vacuo, the residue was chromatographed on silica gel 4:1 hexane:$CHCl_3$ as the eluent. Yield=2.861 g (98% based on 3.150 g of 4-iodo- N,N-dihexylaniline). $^1$H NMR (250 MHz, CDCl$_3$): δ 7.29 (d, 2H, J=9.0 Hz, Ph), 6.50 (d, 2H, J=9.0 Hz, Ph), 3.24 (t, 4H, J=7.7 Hz, —NCH$_2$—), 1.43-1.65 (m, 4H, —NCH$_2$CH$_2$—), 1.19-1.41 (m, 12H, —CH$_2$—), 0.89 (t, 6H, J=6.5 Hz, —CH$_3$), 0.22 (s, 9H, Si—CH$_3$). CI MS m/z: 358.292 ((M+H)$^+$) (calcd 358.293).

Example 19

4-Ethynyl-N,N-dihexylaniline

4-[(Trimethylsilyl)ethynyl]-N,N-dihexylaniline (1.206 g, 3.37×10$^{-3}$ mol), K$_2$CO$_3$ (0.558 g, 4.04×10$^{-3}$ mol), THF (20 ml) and MeOH (20 ml) were added to a 100-ml round-bottom flask. The reaction mixture was stirred at room temperature for 4.5 h under Ar. After the solvent was evaporated, the residue was chromatographed on silica gel with 4:1 hexane:CHCl$_3$ as the eluent. Yield=0.858 g (89% based on 1.206 g of 4-[(trimethylsilyl)ethynyl]-N,N-dihexylaniline). $^1$H NMR (250 MHz, CDCl$_3$): δ 7.32 (d, 2H, J=8.9 Hz, Ph), 6.52 (d, 2H, J=8.9 Hz, Ph), 3.25 (t, 4H, J=7.7 Hz, —NCH$_2$—), 2.96 (s, 1H, ethynyl-H), 1.46-1.64 (m, 4H, —NCH$_2$CH$_2$—), 1.20-1.42 (m, 12H, —CH$_2$—), 0.90 (t, 6H, J=6.6 Hz, —CH$_3$). CI MS m/z: 286.253 ((M+H)$^+$) (calcd 286.253).

Example 20

4,9-bis[4-(N,N-dihexyl)aminophenylethynyl]-6,7-bis(3',7'-dimethyloctyl)[1,2,5]thiadiazolo[3,4-g]quinoxaline 4,9-dibromo-6,7-bis(3',7'-dimethyloctyl)[1,2,5]thiadiazolo[3,4-g]quinoxaline (53.3 mg, 8.51×10$^{-5}$ mol), 4-ethynyl-N,N-dihexylaniline (55.8 mg, 1.95×10$^{-4}$ mol), Pd$_2$dba$_3$ (9.3 mg, 1.0×10$^{-5}$ mol), AsPh$_3$ (26.8 mg, 8.75×10$^{-5}$ mol) and dry THF (15 ml) were added to a 100-ml round-bottom flask. Ar was bubbled into the reaction mixture for 5 min before i-Pr$_2$NH (1.0 ml) was added. The reaction mixture was stirred at 40° C. for 22.5 h under Ar. After the solvent was evaporated, the residue was chromatographed on silica gel with 10:1 hexane:THF as the eluent and further purified by size exclusion column chromatography (BioRad Bio-Beads SX-1 packed in THF, gravity flow). Yield=0.028 g (32% based on 53.3 mg of 4,9-dibromo-6,7-bis(3',7'-dimethyloctyl)[1,2,5]thiadiazolo[3,4-g]quinoxaline).

$^1$H NMR (250 MHz, CDCl$_3$): δ 7.64 (d, 4H, J=8.8 Hz, Ph), 6.62 (d, 4H, J=9.0 Hz, Ph), 3.32 (t, 8H, J=7.6 Hz, —NCH$_2$—), 2.99-3.21 (m, 4H, Ar—CH$_2$), 1.12-2.19 (m, 52H, —CH$_2$—), 1.07 (d, 6H, J=6.5 Hz, —CH$_3$), 0.91 (t, 12H, J=6.6 Hz, —CH$_3$), 0.86 (d, 12H, J=6.6 Hz, —CH$_3$). MALDI-TOF MS m/z: 1029.4 (M$^+$) (calcd 1026.726).

Example 21

N,N-Dihexylaniline

A mixture of aniline (5.90 ml, 6.47×10$^{-2}$ mol), 1-iodohexane (20.0 ml, 0.136 mol) and K$_2$CO$_3$ (18.80 g, 0.136 mol) in 80 ml of EtOH was refluxed for 27 h under Ar. The precipitate was filtered off and washed with CH$_2$Cl$_2$. The filtrate was washed with water and dried over Na$_2$SO$_4$. The residue was chromatographed on silica gel with 4:1 hexane:CHCl$_3$ as the eluent. Yield=14.735 g (87% based on 5.90 ml of aniline). $^1$H NMR (250 MHz, CDCl$_3$): δ 7.20 (dd, 2H, J=7.1, 8.8 Hz, Ph), 6.57-6.66 (m, 3H, Ph), 3.24 (t, 4H, J=7.7 Hz, —NCH$_2$—), 1.48-1.65 (m, 4H, —NCH$_2$CH$_2$—), 1.22-1.40 (m, 12H, —CH$_2$—), 0.90 (t, 6H, J=6.6 Hz, —CH$_3$). CI MS m/z: 262.253 ((M+H)$^+$) (calcd 262.253).

Example 21

N,N-Dihexylaminobenzaldehyde

To a solution of N,N-dihexylaniline (12.02 g, 4.60×10$^{-2}$ mol) in anhydrous 1,2-dichloroethane (200 ml) at room temperature were successively added anhydrous DMF (3.60 ml, 4.65×10$^{-2}$ mol) and POCl$_3$ (5.20 ml, 5.58×10$^{-2}$ mol), and the mixture was refluxed for 5.5 h. After cooling, 2M aqueous NaOAc solution (200 ml) was added and the reaction mixture was stirred overnight. The product was extracted three times with CHCl$_3$ and the combined organic layers were dried over Na$_2$SO$_4$. The residue was chromatographed on silica gel with 1:1 hexane:CHCl$_3$ as the eluent. Yield=10.793 g (81% based on 12.02 g of N,N-dihexylaniline). $^1$H NMR (250 MHz, CDCl$_3$): δ 9.69 (s, 1H, —CHO), 7.70 (dd, 2H, J=8.9 Hz, Ph), 6.63 (d, 2H, J=9.0 Hz, Ph), 3.34 (t, 4H, J=7.8 Hz, —NCH$_2$—), 1.48-1.70 (m, 4H, —NCH$_2$CH$_2$—), 1.19-1.41 (m, 12H, —CH$_2$—), 0.91 (t, 6H, J=6.6 Hz, —CH$_3$). CI MS m/z: 290.247 ((M+H)$^+$) (calcd 290.248).

Example 22

N,N-Dihexyl-4-vinylaniline

To Methyltriphenylphosphonium bromide (3.07 g, 8.59×10$^{-3}$ mol) in 50 ml of dry THF was added w-BuLi (2.2 M solution in hexane, 4.00 ml, 8.80×10$^{-3}$ mol) dropwise at −78° C. After 2.5 h, the reaction mixture was gradually warmed up to 0° C., and again cooled to −78° C. N,N-dihexyl-4-formylaniline (2.26 g, 7.81×10$^{-3}$ mol) in 15 ml of dry THF was slowly added to the reaction mixture. The reaction mixture was stirred overnight and meanwhile gradually warmed up to 10° C. Aqueous NaCl was added to the reaction mixture and the organic layer was extracted with petroleum ether. The organic layer was dried over Na$_2$SO$_4$. After the solvent was evaporated, the residue was chromatographed on silica gel with 1:1 hexane:CHCl$_3$. Yield=0.775 g (35% based on 2.26 g of N,N-dihexyl-4-formylaniline). $^1$H NMR (250 MHz, CDCl$_3$): δ 7.27 (d, 2H, J=8.8 Hz, Ph-H), 6.61 (dd, 1H, J=10.9, 17.8 Hz, vinyl-H), 6.58 (d, 2H, J=8.9 Hz, Ph-H), 5.49 (dd, 1H, J=1.1, 17.6 Hz, vinyl-H), 4.97 (dd, 1H, J=0.9, 10.8 Hz, vinyl-H), 3.25 (t, 4H, J=1.7 Hz, NCH$_2$), 1.48-1.66 (m, 4H, NCH$_2$CH$_2$—), 1.20-1.42 (m, 12H, —CH$_2$—), 0.89 (t, 6H, J=6.6 Hz, —CH$_3$). CI MS m/z: 288.269 ((M+H)$^+$) (calcd 288.269).

Example 23

4,7-Bis(4'-(N,N-dihexylamino)phenylethynyl)benzo[c][1,2,5]thiadiazole 4,7-Dibromobenzo[c][1,2,5]thiadiazole (0.1009 g, 3.43×10$^{-4}$ mol), N,N-dihexylamino-4-ethynylbenzene (0.2089 g, 7.32×10$^{-4}$ mol), Pd$_2$dba$_3$ (66.9 mg, 7.31×10$^{-5}$ mol), AsPh$_3$ (0.1071 g, 3.50×10$^{-4}$ mol) and dry THF (20 ml) were added to a 100-ml round-bottom flask. Ar was bubbled into the reaction mixture for 10 min before i-Pr$_2$EtN (0.30 ml) was added. The reaction mixture was stirred at 43° C. for 20.5 h under Ar. After the solvent was evaporated, the reaction mixture was chromatographed on silica gel with 80:10:1 hexane:THF:Et3N. The product was further purified by size exclusion column chromatography (BioRad Bio-Beads SX-1 packed in THF, gravity flow). Yield=0.1488 g (62% based on 0.1009 g of 4,7-Dibromobenzo[c][1,2,5]thiadiazole). $^1$H NMR (250 MHz, CDCl$_3$): δ 7.68 (s, 2H, Ph), 7.49 (d, 4H, J=8.8 Hz, Ph), 6.59 (d, 4H, J=9.0 Hz, Ph), 3.29 (t, 8H, J=7.6 Hz, —NCH$_2$—), 1.50-1.70 (m, 8H, —NCH$_2$CH$_2$—), 1.19-1.45 (m, 24H, —CH$_2$—), 0.91 (t, 12H, J=6.6 Hz, —CH$_3$). MALDI-TOF MS m/z: 704.13 (M$^+$) (calcd 702.470).

Example 24

4,7-Bis(4'-(N,N-dihexylamino)phenylethenyl)benzo[c][1,2,5]thiadiazole 4,7-Dibromobenzo[c][1,2,5]thiadiazole (50.3 mg, 1.71×10$^{-4}$ mol), N,N-dihexylamino-4-vinylbenzene (120.0 mg, 4.17×10$^{-4}$ mol), Pd$_2$dba$_3$ (41.7 mg, 4.55×10$^{-5}$ mol) and dry THF (10 ml) were added to a 100-ml round-bottom flask. Ar was bubbled into the reaction mixture for 5 min before i-Pr$_2$EtN (0.30 ml) and P(t-Bu)$_3$ (10 wt % in hexane, 0.50 ml, 1.6×10$^{-4}$ mol) were added. The reaction mixture was stirred at 39° C. for 21 h under Ar. After the solvent was evaporated, the reaction mixture was chromatographed on silica gel with 30:15:1 hexane:CHCl$_3$:Et$_3$N. Yield=0.035 g (29% based on 50.3 mg of 4,7-dibromobenzo[c][1,2,5]thiadiazole). $^1$H NMR (250 MHz, CDCl$_3$): δ 7.83 (d, 2H, J=16.2 Hz, vinyl-H), 7.61 (s, 2H, Ph), 7.51 (d, 4H, J=8.8 Hz, Ph), 7.45 (d, 2H, J=16.3 Hz, vinyl-H), 6.64 (d, 4H, J=8.8 Hz, Ph), 3.30 (t, 8H, J=1.6 Hz, —NCH$_2$—), 1.46-1.69 (m, 8H, —NCH$_2$CH$_2$—), 1.16-1.40 (m, 24H, —CH$_2$—), 0.88 (t, 12H, J=6.8 Hz, —CH$_3$). MALDI-TOF MS m/z: 707.55 (M$^+$) (calcd 706.501).

Example 25

4-Dodecyloxybenzaldehyde

4-Hydroxybenzaldehyde (8.00 g, 6.55×10$^{-2}$ mol), 1-bromododecane (16.50 ml, 6.87×10$^{-2}$ mol), K$_2$CO$_3$ (9.05 g, 6.55×10$^{-2}$ mol) and dry DMF (100 ml) were added to a two-neck round-bottom flask. The reaction mixture was stirred at 105° C. for 21.5 h under Ar. After cooling, the solution was diluted with H$_2$O, 2M HCl and extracted three times with CH$_2$Cl$_2$. The combined organic layers were washed with aqueous NaHCO$_3$, H$_2$O and dried over Na$_2$SO$_4$. The product was chromatographed on silica gel with 1:1 hexane:CH$_2$Cl$_2$ as the eluent. Yield=19.02 g (100% based on 8.00 g of 4-hydroxybenzaldehyde). $^1$H NMR (250 MHz, CDCl$_3$): δ 9.88 (s, 1H, —CHO), 7.83 (d, 2H, J=8.8 Hz, Ph), 6.99 (d, 2H, J=8.7 Hz, Ph), 4.04 (t, 2H, J=6.5 Hz, OCH$_2$), 1.82 (quint, 2H, J=6.9 Hz, OCH$_2$CH$_2$), 1.40-1.54 (m, 2H, —CH$_2$—), 1.16-1.40 (m, 16H, —CH$_2$—), 0.88 (t, 3H, J=6.5 Hz, —CH$_3$). CI MS m/z: 291.232 ((M+H)$^+$) (calcd 291.232).

Example 26

4-Dodecyloxystyrene

To Methyltriphenylphosphonium bromide (8.13 g, 2.28×10$^{-2}$ mol) in 60 ml of dry THF was added n-BuLi (1.6 M solution in hexane, 15.8 ml, 2.53×10$^{-2}$ mol) dropwise at −78° C. After 2.5 h, the reaction mixture was gradually warmed up to 0° C., and again cooled to −78° C. 4-Dodecyloxybenzaldehyde (6.00 g, 2.07×10$^{-2}$ mol) in 20 ml of dry THF was slowly added to the reaction mixture. The reaction mixture was stirred overnight and meanwhile gradually warmed up to 10° C. Aqueous NaCl was added to the reaction mixture and the organic layer was extracted with petroleum ether. The organic layer was dried over Na$_2$SO$_4$. After the solvent was evaporated, the residue was chromatographed on silica gel with 1:1 hexane:CH$_2$Cl$_2$. Yield=5.358 g (90% based on 6.00 g of 4-dodecyloxybenzaldehyde). $^1$H NMR (250 MHz, CDCl$_3$): δ 7.33 (d, 2H, J=8.7 Hz, Ph), 6.85 (d, 2H, J=8.7 Hz, Ph), 6.66 (dd, 1H, J=10.8, 17.6 Hz, vinyl-H), 5.60 (d, 1H, J=17.5 Hz, vinyl-H), 5.11 (d, 1H, J=10.6 Hz, vinyl-H), 3.95 (t, 2H, J=6.6 Hz, OCH$_2$), 1.78 (quint, 2H, J=7.0 Hz, OCH$_2$CH$_2$), 1.38-1.52 (m, 2H, —CH$_2$—), 1.16-1.38 (m, 16H, —CH$_2$—), 0.88 (t, 3H, J=6.6 Hz, —CH$_3$). CI MS m/z: 288.245 (M$^+$) (calcd 288.245).

Example 27

4,9-bis[(4'-dodecyloxy)phenylethenyl]-6,7-bis(3',7'-dimethyloctyl)[1,2,5]thiadiazolo[3,4-g]quinoxaline 4,9-Dibromo-6,7-bis(3',7'-dimethyloctyl)[1,2,5]thiadiazolo[3,4-g]quinoxaline (75.9 mg, 1.21×10$^{-4}$ mol), 4-dodecyloxystyrene (77.0 mg, 2.67×10$^{-4}$ mol), Pd$_2$dba$_3$ (29.5 mg, 3.2×10$^{-5}$ mol) and dry THF (15 ml) were added to a 100-ml round-bottom flask. Ar was bubbled into the reaction mixture for 10 min before i-Pr$_2$EtN (0.30 ml) and P(f-Bu)$_3$ (10 wt % solution in hexane, 0.37 ml, 1.2×10$^{-4}$ mol) were added. The reaction mixture was stirred at 40° C. for 15 h under Ar. After the solvent was evaporated, the residue was chromatographed on silica gel with 80:10:1 hexane:THF:Et$_3$N as the eluent. The product was further purified by size exclusion column chromatography (BioRad Bio-Beads SX-1 packed in THF, gravity flow). Yield=0.065 g (52% based on 75.9 mg of 4,9-dibromo-6,7-bis(3',7'-dimethyloctyl)[1,2,5]thiadiazolo[3,4-g]quinoxaline). $^1$H NMR (250 MHz, CDCl$_3$): δ 8.78 (s, 4H, vinyl-H), 7.72 (d, 4H, J=8.7 Hz, Ph), 6.96 (d, 4H, J=8.7 Hz, Ph), 4.02 (t, 4H, J=6.6 Hz, —OCH$_2$—), 2.98-3.20 (m, 4H, Ar—CH$_2$—), 1.1-2.2 (m, 60H, —CH$_2$—), 1.07 (d, 6H, J=6.5 Hz, —CH$_2$—), 0.88 (t, 6H, J=6.7 Hz, —CH$_3$), 0.87 (d, 12H, J=6.7 Hz, —CH$_3$). MALDI-TOF MS m/z: 1040.2 (M$^+$) (calcd 1040.788).

Example 28

4-Bromo-7-(N,N-dihexylamino)benzo[c][1,2,5]thiadiazole 4,7-Dibromobenzo[c][1,2,5]thiadiazole (0.500 g, 1.70×10$^{-3}$ mol), N,N-dihexylamine (0.50 ml, 2.1×10$^{-3}$ mol), Pd$_2$dba$_3$ (45 mg, 4.9×10$^{-5}$ mol), 2-(di-t-butylphosphino)biphenyl (30 mg, 1.0×10$^{-4}$ mol), NaOt-Bu (0.242 g, 2.5×10$^{-3}$ mol), toluene (4.0 ml) and DMF (0.40 ml) were added to a reaction vial. The reaction mixture was stirred at 160° C. for 15 min under microwave irradiation. After the reaction mixture was filtered and the solvent was evaporated, the residue was chromatographed on silica gel with 1:1 hexane:CH$_2$Cl$_2$. Yield=0.271 g (40% based on 0.500 g of 4,7-dibromobenzo[c][1,2,5]thiadiazole). $^1$H NMR (250 MHz, CDCl$_3$): δ 7.59 (d, 1H, J=8.4 Hz, Ph-H), 6.31 (d, 1H, J=8.5 Hz, Ph-H), 3.68 (t, 4H, J=7.7 Hz, —NCH$_2$), 1.51-1.75 (m, 4H, —NCH$_2$CH$_2$—), 1.20-1.44 (m, 12H, —CH$_2$—), 0.89 (t, 6H, J=6.7 Hz, —CH$_3$). CI MS m/z: 398.125 ((M+H)$^+$) (calcd 398.127).

Example 29

4,7-Bis(4'-(N,N-dihexylamino)benzo[c][1,2,5]thiadiazol-7'-ylethynyl)benzo[c][1,2,5]thiadiazole 4-Bromo-7-(N,N-dihexylamino)benzo[c][1,2,5]thiadiazole (0.493 g, 1.24×10$^{-3}$ mol), 4,7-bis[(trimethylsilyl)ethynyl]benzo[c][1,2,5]thiadiazole (0.169 g, 5.14×10$^{-4}$ mol), Pd(PPh$_3$)$_4$ (73.6 mg, 6.4×10$^{-5}$ mol), CuI (1.3 mg, 6.8×10$^{-6}$ mol), K$_2$CO$_3$ (0.334 g, 2.4×10$^{-3}$ mol) and dry THF (20 ml) were added to a 100-ml round-bottom flask. Ar was bubbled into the reaction mixture for 10 min before piperidine (1.0 ml) and MeOH (2.0 ml) were added. The reaction mixture was stirred at 50° C. for 24 h under Ar. After the solvent was evaporated, the residue was chromatographed on silica gel with 1:2 hexane:CHCl$_3$ as the eluent. Yield=quantitative. $^1$H NMR (250 MHz, CDCl$_3$): δ 7.85 (s, 2H, Ph-H), 7.80 (d, 2H, J=8.3 Hz, Ph-H), 6.41 (d, 2H, J=8.4 Hz, Ph-H), 3.81 (t, 8H, J=7.8 Hz, —NCH$_2$), 1.62-1.80 (m, 8H, —NCH$_2$CH$_2$—), 1.20-1.49 (m, 24H, —CH$_2$—), 0.91 (t, 12H, J=7.0 Hz, —CH$_3$). MALDI-TOF MS m/z: 820.78 (M$^+$) (calcd 818.395).

Example 30

1,4-Di-n-octyloxybenzene

Hydroquinone (10.00 g, 9.08×10$^{-2}$ mol) was dissolved in 100 ml of ethanol. After addition of KOH (10.79 g, 0.192 mol), the solution was stirred under reflux for 20 min. 1-Bromooctane (33.0 ml, 0.191 mol) was added dropwise to the light brown solution over 1 h, followed by stirring under reflux for 3 h. After cooling, CHCl$_3$ and H$_2$O were added to the reaction mixture and the organic layer was collected. The aqueous layer was further washed with CHCl$_3$. The combined organic layers were washed with aqueous NaHCO$_3$ and dried over Na$_2$SO$_4$. After the solvent was evaporated, the residue was chromatographed on silica gel with 1:1 hexane:CHCl$_3$ as the eluent. Yield=27.33 g (90% based on 10.00 g of hydroquinone). $^1$H NMR (300 MHz, CDCl$_3$): δ 6.82 (s, 4H, Ph-H), 3.90 (t, 4H, J=6.6 Hz, —OCH$_2$—), 1.75 (quint, 4H, J=7.0 Hz, —OCCH$_2$—), 1.37-1.51 (m, 4H, —OCCCH$_2$), 1.17-1.37 (m, 16H, —CH$_2$—), 1.20-1.49 (m, 24H, —CH$_2$—), 0.88 (t, 6H, J=6.6 Hz, —CH$_3$). CI MS m/z: 334.287 (M$^+$) (calcd 334.287).

Example 31

1,4-Diiodo-2,5-di-n-octyloxybenzene 1,4-Dioctyloxybenzene (19.282 g, 5.76×10$^{-2}$ mol) was dissolved in acetic acid (60 ml) and CCl$_4$ (20 ml). To this solution were added iodine (32.2 g, 0.127 mol), conc. H$_2$SO$_4$ (7.0 ml), distilled water (4.0 ml), and finally potassium iodate (12.4 g, 5.79×10$^{-2}$ mol). The reaction mixture was stirred for 28 h under reflux. After cooling, aqueous Na$_2$SO$_4$ was added until the brown color of iodine had disappeared, and the reaction mixture was poured into ice water. The organic layer was extracted with CH$_2$Cl$_2$, and the combined organic layers were washed with aqueous NaHCO$_3$ and dried over Na$_2$SO$_4$. After the solvent was evaporated, the residue was chromatographed on silica gel with 4:1 hexane:CHCl$_3$ as the eluent. Yield=12.399 g (37% based on 19.286 g of 1,4-dioctyloxybenzene). $^1$H NMR (300 MHz, CDCl$_3$): δ 7.17 (s, 2H, Ph-H), 3.92 (t, 4H, J=6.4 Hz, —OCH$_2$—), 1.80 (quint, 4H, J=6.9 Hz, —OCH$_2$CH$_2$—), 1.42-1.57 (m, 4H, —OCH$_2$CH$_2$CH$_2$—), 1.18-1.42 (m, 16H, —CH$_2$—), 0.89 (t, 6H, J=6.8 Hz, —CH$_3$). CI MS m/z: 586.078 (M$^+$) (calcd 586.080).

Example 32

1,4-Bis(trimethylsilylethynyl)-2,5-di-n-octyloxybenzene 1,4-Diiodo-2,5-di-n-octyloxybenzene (4.01 g, 6.84×10$^{-3}$ mol), Pd(PPh$_3$)$_2$Cl$_2$ (0.248 g, 3.53×10$^{-4}$ mol), PPh$_3$ (0.179 g, 6.82×10$^{-4}$ mol), CuI (0.072 g, 3.8×10$^{-4}$ mol) and piperidine (40 ml) were added to a 100-ml round-bottom flask. Ar was bubbled into the reaction mixture for 5 min before trimethylsilylacetylene (3.0 ml, 2.1×10$^{-2}$ mol) was added. The reaction mixture was stirred at 60° C. for 2 h under Ar. After cooling, the solvent was evaporated. CHCl$_3$ was added to the residue, and the organic solution was washed with aqueous NH$_4$Cl (3 times), water, and dried over Na$_2$SO$_4$. After the solvent was evaporated, the residue was chromatographed on silica gel with 2:1 hexane:CHCl$_3$ as the eluent. Yield=3.455 g (96% based on 4.01 g of 1,4-diiodo-2,5-di-n-octyloxybenzene). $^1$H NMR (300 MHz, CDCl$_3$): δ 6.88 (s, 2H, Ph-H), 3.94 (t, 4H, J=6.4 Hz, —OCH$_2$), 1.78 (quint, 4H, J=6.9 Hz, —OCH$_2$CH$_2$—), 1.42-1.60 (m, 4H, —OCH$_2$CH$_2$CH$_2$—), 1.16-1.42 (m, 16H, —CH$_2$—), 0.88 (t, 6H, J=6.7 Hz, —CH$_3$), 0.25 (s, 18H, —Si—CH$_3$). CI MS m/z: 526.366 (M$^+$) (calcd 526.366).

Example 33

1,4-Diethynyl-2,5-di-n-octyloxybenzene 1,4-Bis(trimethylsilylethynyl)-2,5-di-n-octyloxybenzene (2.331 g, 4.42×10$^{-3}$ mol) was dissolved in a mixture of THF (25 ml) and MeOH (25 ml). 5N NaOH (2.0 ml, 1.0×10$^{-2}$ mol) was added and the solution was stirred for 3 h under Ar. Water was added to the reaction mixture. The organic layer was extracted three times with CHCl$_3$. The combined organic layers were dried over Na$_2$SO$_4$. The residue was chromatographed on silica gel with 1:1 hexane:CHCl$_3$ as the eluent. Yield=1.419 g (84% based on 2.331 g of 1,4-bis(trimethylsilylethynyi)-2,5-di-n-octyloxybenzene). $^1$H NMR (300 MHz, CDCl$_3$): δ 6.95 (s, 2H, Ph-H), 3.97 (t, 8H, J=6.6 Hz, —OCH$_2$—), 3.33 (s, 2H, —CC—H), 1.80 (quint, 4H, J=7.0 Hz, —OCH$_2$CH$_2$—), 1.39-1.52 (m, 4H, —OCH$_2$CH$_2$CH$_2$—), 1.15-1.39 (m, 16H, —CH$_2$—), 0.88 (t, 6H, J=6.7 Hz, —CH$_3$). CI MS m/z: 382.285 (M$^+$) (calcd 382.287).

Example 34

1,4-Bis[(4'-benzo[c][1,2,5]thiadiazolyl)ethynyl]-2,5-di-n-octyloxybenzene

4-Bromobenzo[c][1,2,5]thiadiazole (0.151 g, 7.02×10$^{-4}$ mol), 1,4-diethynyl-2,5-di-n-octyloxybenzene (0.121 g, 3.16×10$^{-4}$ mol), Pd(PPh$_3$)$_4$ (80.0 mg, 6.92×10$^{-5}$ mol), CuI (5.6 mg, 2.9×10$^{-5}$ mol) and dry THF (10 ml) were added to a 100-ml round-bottom flask. Ar was bubbled into the reaction mixture for 5 min before piperidine (0.50 ml) was added. The reaction mixture was stirred at 53° C. for 12 h under Ar. After cooling, the solvent was evaporated. The residue was chromatographed on silica gel with 4:1 CHCl$_3$:hexane as the eluent. Yield=0.145 g (70% based on 0.121 g of 1,4-diethynyl-2,5-di-n-octyloxybenzene). $^1$H NMR (300 MHz, CDCl$_3$): δ 8.01 (dd, 2H, J=1.0, 8.8 Hz, Ph-H), 7.81 (dd, 2H, J=1.0, 7.0 Hz, Ph-H), 7.60 (dd, 2H, J=7.0, 8.8 Hz, Ph-H), 7.17 (s, 2H, Ph-H), 4.11 (t, 4H, J=6.4 Hz, —OCH$_2$—), 1.91 (quint, 4H, J=7.0 Hz, —OCH$_2$CH$_2$—), 1.50-1.65 (m, 4H, —OCH$_2$CH$_2$CH$_2$—), 1.12-1.47 (m, 16H, —CH$_2$—), 0.84 (t, 12H, J=6.8 Hz, —CH$_3$). MALDI-TOF MS m/z: 820.78 (M$^+$) (calcd 818.395).

Example 35

1-(4'-N,N-dihexylaminophenylethynyl)-4-iodobenzene (4-N,N-dihexylaminophenyl)ethyne (0.694 g, 2.43×10$^{-3}$ mol), 1,4-diiodobenzene (3.04 g, 9.21×10$^{-3}$ mol), Pd(PPh$_3$)$_2$Cl$_2$ (0.176 g, 2.51×10$^{-4}$ mol), CuI (27.7 mg, 1.45×10$^{-4}$ mol) and Et$_3$N (25 ml) were added to a 100-ml round-bottom flask. Ar was bubbled into the reaction mixture for 5 min. The reaction mixture was stirred at 45° C. for 14.5 h under Ar. After cooling, the solvent was evaporated. The residue was chromatographed on silica gel with 3:1 hexane:CHCl$_3$ as the eluent. Yield=0.644 g (54% based on 0.694 g of (4-N,N-dihexylaminophenyl)ethyne). $^1$H NMR (300 MHz, CDCl$_3$): δ 7.63 (d, 2H, J=8.3 Hz, Ph-H), 7.34 (d, 2H, J=8.8 Hz, Ph-H), 7.20 (d, 2H, J=8.3 Hz, Ph-H), 6.56 (d, 2H, J=8.9 Hz, Ph-H), 3.26 (t, 4H, J=7.7 Hz, —NCH$_2$—), 1.45-1.68 (m, 4H, —NCH$_2$CH$_2$—), 1.18-1.42 (m, 12H, —CH$_2$—), 0.90 (t, 12H, J=6.5 Hz, —CH$_3$). CI MS m/z: 487.172 (M$^+$) (calcd 487.174).

Example 36

1-(4-N,N-dihexylaminophenylethynyl-4-(trimethylsilylethynyl)benzene 1-(4-N,N-dihexylaminophenylethynyl-4-iodobenzene (0.530 g, 1.09×10$^{-3}$ mol), Pd(PPh$_3$)$_2$Cl$_2$ (81 mg, 1.2×10$^{-4}$ mol), CuI (11 mg, 5.8×10$^{-5}$ mol) and Et$_3$N (20 ml) were added to a 100-ml round-bottom flask. Ar was bubbled into the reaction mixture for 5 min before (trimethylsilyl)acetylene (0.62 ml, 4.4×10$^{-3}$ mol) was added. The reaction mixture was stirred at 45° C. for 3 h under Ar. After cooling, the solvent was evaporated. The residue was chromatographed on silica gel with 3:1 hexane:CH$_2$Cl$_2$ as the eluent. Yield= 0.484 g (97% based on 0.530 g of 1-(4-N,N-dihexylaminophenylethynyl-4-iodobenzene).

$^1$H NMR (300 MHz, CDCl$_3$): δ 7.40 (s, 4H, Ph-H), 7.34 (d, 2H, J=8.9 Hz, Ph-H), 6.56 (d, 2H, J=9.0 Hz, Ph-H), 3.27 (t, 4H, J=7.7 Hz, —NCH$_2$), 1.47-1.65 (m, 4H, —NCH$_2$CH$_2$—), 1.19-1.38 (m, 12H, —CH$_2$—), 0.90 (t, 6H, J=6.6 Hz, —CH$_3$), 0.25 (s, 9H, —Si—CH$_3$). CI MS m/z: 458.323 ((M+H)$^+$) (calcd 458.324).

Example 37

1-(4-N,N-dihexylaminophenylethynyl-4-ethynylbenzene 1-(4-N,N-dihexylaminophenylethynyl-4-(trimethylsilylethynyl)benzene (0.262 g, 5.72×10$^{-4}$ mol), K$_2$CO$_3$ (0.109 g, 7.89×10$^{-4}$ mol), THF (5.0 ml) and MeOH (3.0 ml) were added to a 100-ml round bottom flask. The reaction mixture was stirred at room temperature for 2 h under Ar. Subsequently, the reaction mixture was filtered and the filtrate was evaporated. Yield=0.220 g (~100% based on 0.262 g of 1-(4-N,N-dihexylaminophenylethynyl-4-(trimethylsilylethynyl)benzene). $^1$H NMR (300 MHz, CDCl$_3$): δ 7.43 (s, 4H, Ph-H), 7.35 (d, 2H, J=9.0 Hz, Ph-H), 6.57 (d, 2H, J=9.1 Hz, Ph-H), 3.27 (t, 4H, J=7.7 Hz, —NCH$_2$—), 3.14 (s, 1H, —CC—H), 1.45-1.65 (m, 4H, —NCH$_2$CH$_2$—), 1.18-1.40 (m, 12H, —CH$_2$—), 0.90 (t, 6H, J=6.6 Hz, —CH$_3$). CI MS m/z: 386.284 ((M+H)$^+$) (calcd 386.285)

Example 38

1,4-Bis[4-(4-N,N-dihexylaminophenylethynyl)phenylethynyl]-2,5-di-n-octyloxybenzene 1-(4-N,N-dihexylaminophenylethynyl)-4-ethynylbenzene (63.6 mg, 1.65×10$^{-4}$ mol), 1,4-diiodo-2,5-di-n-octyloxybenzene (46.4 mg, 7.91×10$^{-5}$ mol), Pd(PPh$_3$)$_4$ (20.0 mg, 1.73×10$^{-5}$ mol), CuI (1.6 mg, 8.4×10$^{-6}$ mol) and dry THF (6.0 ml) were added to a 100-ml round-bottom flask. Ar was bubbled into the reaction mixture for 5 min before piperidine (0.50 ml) was added. The reaction mixture was stirred at 50° C. for 17 h under Ar. After cooling, the solvent was evaporated. The residue was chromatographed on silica gel with 1:1 hexane:CHCl$_3$ as the eluent. The crude product was further purified by size exclusion column chromatography (BioRad Bio-Beads SX-1 packed in THF, gravity flow). Yield=51.5 mg (59% based on 46.4 mg of 1,4-diiodo-2,5-di-n-octyloxybenzene). $^1$H NMR (300 MHz, CDCl$_3$): δ 7.46 (dd, 8H, J=8.4, 9.6 Hz, Ph-H), 7.36 (d, 4H, J=8.8 Hz, Ph-H), 7.01 (s, 2H, Ph-H), 6.57 (d, 4H, J=8.7 Hz, Ph-H), 4.03 (t, 4H, J=6.5 Hz, —OCH$_2$—), 3.28 (t, 8H, J=7.6 Hz, —OCH$_2$—), 1.86 (quint, 4H, J=6.8 Hz, —OCH$_2$CH$_2$—), 1.47-1.65 (m, 12H, —CH$_2$—), 1.16-1.43 (m, 40H, —CH$_2$—), 0.77-0.98 (m, 18H, —CH$_3$). MALDI-TOF MS m/z: 1100.78 (M$^+$) (calcd 1100.810).

Example 39

4-(4-N,N-Dihexylaminophenylethynyl)-7-iodobenzo[c][1,2,5]thiadiazole (4-N,N-dihexylaminophenyl)ethyne (0.251 g, 8.79×10$^{-4}$ mol), 4,7-diiodobenzo[c][1,2,5]thiadiazole (0.584 g, 1.51×10$^{-3}$ mol), Pd$_2$dba$_3$ (99.4 mg, 1.1×10$^{-4}$ mol), AsPh$_3$ (0.283 g, 9.2×10$^{-4}$ mol) and dry THF (15 ml) were added to a 100-ml round-bottom flask. Ar was bubbled into the reaction mixture for 5 min before i-Pr$_2$EtN (1.0 ml) was added. The reaction mixture was stirred at 46° C. for 19 h under Ar. After cooling, the solvent was evaporated. The residue was chromatographed on silica gel with 1:1 hexane:CHCl$_3$ as the eluent. Yield=0.241 g (50% based on 0.251 g of (4-N,N-dihexylaminophenyl)ethyne). $^1$H NMR (300 MHz, CDCl$_3$): δ 8.04 (d, 1H, J=7.5 Hz, Ph-H), 7.49 (d, 2H, J=8.9 Hz, Ph-H), 7.45 (d, 1H, J=7.5 Hz, Ph-H), 6.59 (d, 2H, J=8.9 Hz, Ph-H), 3.29 (t, 4H, J=7.7 Hz, —NCH$_2$—), 1.51-1.66 (m, 4H, —NCH$_2$CH$_2$—), 1.19-140 (m, 12H, —CH$_2$—), 0.91 (t, 6H, J=6.7 Hz, —CH$_3$). MALDI-TOF MS m/z: 546.147 ((M+H)$^+$) (calcd 546.144).

Example 40

1,4-Bis([7-(4-N,N-dihexylaminophenylethynyl)benzo[c][1,2,5]thiadlazol-4-yl]ethynyl)-2,5-di-n-octyloxybenzene 4-(4-N,N-dihexylaminophenylethynyl)-7-iodobenzo[c][1,2,5]thiadiazole (0.102 g, 1.87×10$^{-4}$ mol), 1,4-diethynyl-2,5-di-n-octyloxybenzene (33.1 mg, 8.65×10$^{-5}$ mol), Pd(PPh$_3$)$_4$ (23.2 mg, 2.01×10$^{-5}$ mol), CuI (1.6 mg, 8.4×10$^{-6}$ mol) and dry THF (6.0 ml) were added to a 100-ml round-bottom flask. Ar was bubbled into the reaction mixture for 5 min before piperidine (0.50 ml) was added. The reaction mixture was stirred at 40° C. for 12 h under Ar. After cooling, the solvent was evaporated. The residue was chromatographed on silica gel with 5:1 hexane:THF as the eluent. Yield=0.101 g (96% based on 33.1 mg of 1,4-diethynyl-2,5-di-n-octyloxybenzene). $^1$H NMR (300 MHz, CDCl$_3$): δ 7.76 (d, 2H, J=7.5 Hz, Ph-H), 7.71 (d, 2H, J=7.4 Hz, Ph-H), 7.51 (d, 4H, J=8.3 Hz, Ph-H), 7.16 (s, 2H, Ph-H), 6.60 (d, 4H, Ph-H), 4.11 (t, 4H, J=6.5 Hz, —OCH$_2$—), 3.30 (t, 8H, J=7.5 Hz, —NCH$_2$—), 1.92 (quint, 4H, J=7.5 Hz, —CH$_2$—), 1.46-1.72 (m, 12H, —CH$_2$—), 1.14-1.46 (m, 40H, —CH$_2$—), 0.74-1.00 (m, 18H, —CH$_3$). MALDI-TOF MS m/z: 1217.02 (M$^+$) (calcd 1216.735).

Example 41

1-(4'-N,N-dihexylaminophenylethynyl)-4-iodo-2,5-di-n-octyloxybenzene 1-(4-N,N-dihexylaminophenylethynyl-4-ethynylbenzene (0.3317 g, 1.16×10$^{-3}$ mol), 1,4-diiodo-2,5-di-n-octyloxybenzene (2.046 g, 3.49×10$^{-3}$ mol), Pd(PPh$_3$)$_2$Cl$_2$ (90.4 mg, 1.29×10$^{-4}$ mol), CuI (9.2 mg, 4.8×10$^{-5}$ mol) and triethylamine (16.0 ml) were added to a 100-ml round-bottom flask. Ar was bubbled into the reaction mixture for 5 min and the reaction mixture was stirred at 48° C. for 16.5 h under Ar. After cooling, the solvent was evaporated. The residue was chromatographed on silica gel with 3:1 hexane:CH$_2$Cl$_2$ as the eluent. Yield=0.502 g (58% based on 0.3317 g of 1-(4-N,N-dihexylaminophenylethynyl-4-ethynylbenzene). $^1$H NMR (300 MHz, CDCl$_3$): δ 7.35 (d, 2H, J=8.7 Hz, Ph-H), 7.26 (s, 1H, Ph-H), 6.89 (s, 1H, Ph-H), 6.55 (d, 2H, J=8.7 Hz, Ph-H), 3.90-4.01 (m, 4H, —OCH$_2$—), 3.26 (t, 4H, J=7.5 Hz, —NCH$_2$—), 1.73-1.88 (m, 4H, —CH$_2$—), 1.43-1.61 (m, 4H, —CH$_2$—), 1.16-1.43 (m, 32H, —CH$_2$—), 0.76-1.00 (m, 12H, —CH$_3$). ESI MS m/z: 744.41 ((M+H)$^+$) (calcd 743.410).

Example 42

4,7-diethynylbenzo[c][1,2,5]thiadiazole 4,7-Bis(trimethylsilylethynyl)benzo[c][1,2,5]thiadiazole (0.126 g, 3.83×10$^{-4}$ mol), K$_2$CO$_3$ (0.214 g, 1.55×10$^{-3}$ mol), CH$_2$Cl$_2$ (5.0 ml) and MeOH (5.0 ml) were added to a 100-ml round-bottom flask. The reaction mixture was stirred at room temperature for 2.5 h under Ar. The reaction mixture was fdtered and the solvent was evaporated. The residue was chromatographed on short silica gel column with CH$_2$Cl$_2$ as the eluent. Yield=0.0663 g (94% based on 0.126 g of 4,7-bis(trimethylsilylethynyl)benzo[c][1,2,5]thiadiazole). $^1$H NMR (300 MHz, CDCl$_3$): δ 7.78 (s, 2H, Ph-H), 3.70 (s, 2H, ethynyl-H). CI MS m/z: 184.010 (M$^+$) (calcd 184.010).

Example 43

4,7-Bis([4'-(4"-N,N-dihexylaminophenylethynyl)-2',5'-di-n-octyloxyphen-1'-yl]ethynyl)benzo[c][1,2,5]thiadiazole 1-(4'-N,N-dihexylaminophenylethynyl)-4-iodo-2,5-di-n-octyloxybenzene (0.2952 g, 3.97×10$^{-4}$ mol), 4,7-diethynyl-benzo[c][1,2,5]thiadiazole (35.7 mg, 1.94×10$^{-4}$ mol), Pd(PPh$_3$)$_4$ (49.2 mg, 4.26×10$^{-5}$ mol), CuI (4.1 mg, 2.2×10$^{-5}$ mol) and dry THF (6.0 ml) were added to a 100-ml round-bottom flask. Ar was bubbled into the reaction mixture for 5 min before piperidine (0.50 ml) was added. The reaction mixture was stirred at 48° C. for 3 h under Ar. After cooling, the solvent was evaporated. The residue was chromatographed on silica gel with 8:1 hexane:THF as the eluent. Yield=0.2187 g (80% based on 35.7 mg of 4,7-diethynyl-benzo[c][1,2,5]thiadiazole). $^1$H NMR (300 MHz, CDCl$_3$): δ 7.76 (s, 2H, Ph-H), 7.38 (d, 4H, J=8.9 Hz, Ph-H), 7.11 (s, 2H, Ph-H), 7.02 (s, 2H,Ph-H), 6.57 (d, 4H, J=9.1 Hz, Ph-H), 4.08 (t, 4H, J=6.5 Hz, —OCH$_2$—), 4.05 (t, 4H, J=6.4 Hz, —OCH$_2$—), 3.28 (t, 8H, J=7.5 Hz, —NCH$_2$—), 1.89 (quint, 8H, J=7.4 Hz, —CH$_2$—), 1.48-1.69 (m, 8H, —CH$_2$—), 1.16-1.47 (m, 64H, —CH$_2$—), 0.78-1.01 (m, 24H, —CH$_3$). MALDI-TOF MS m/z: 1415.0 (M$^+$) (calcd 1415.013).

Figure 11:
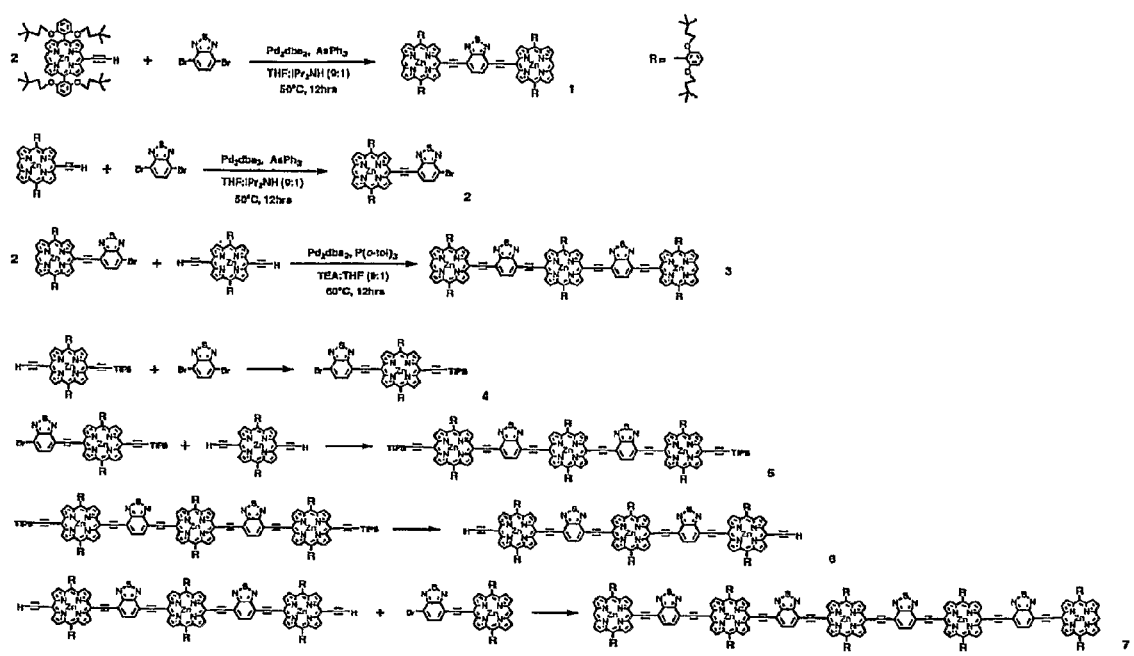
FIG. 11 presents synthetic schemes for compounds 1-7.
Figure 12:
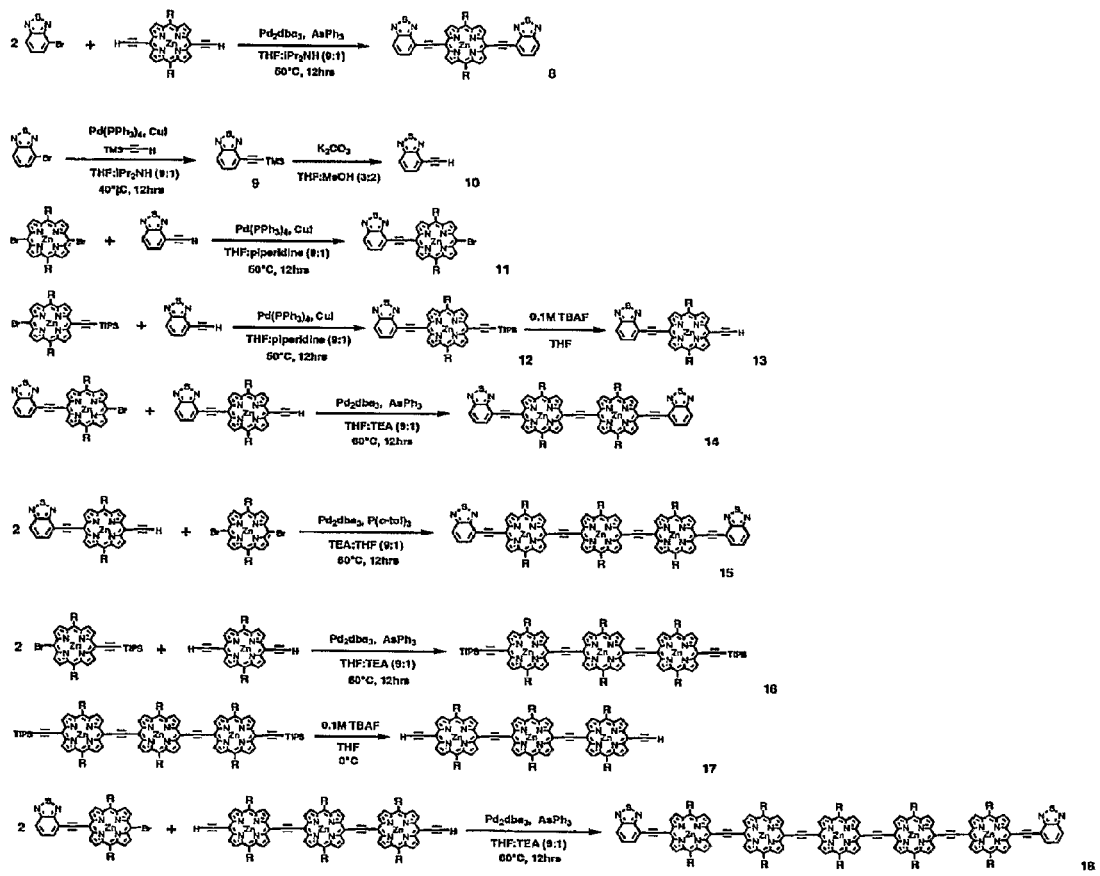
FIG. 12 presents synthetic schemes for certain compounds 8-18.
Figure 13:
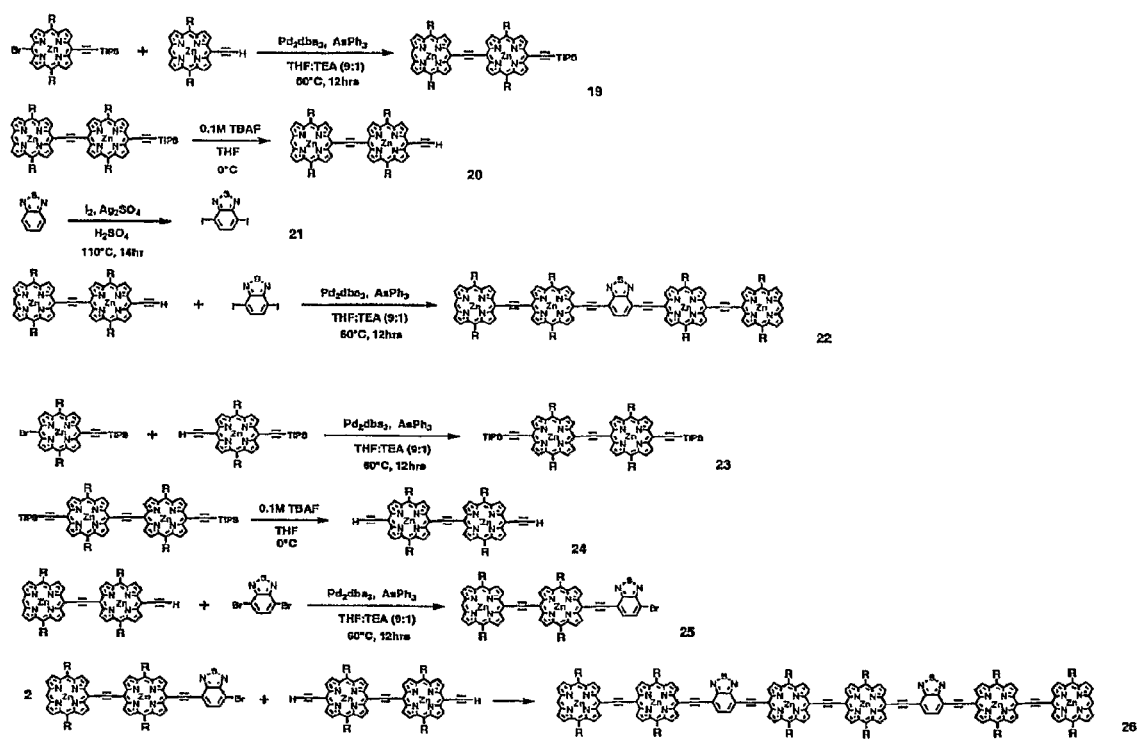
FIG. 13 presents synthetic schemes for compounds 19-26.
Figure 14:
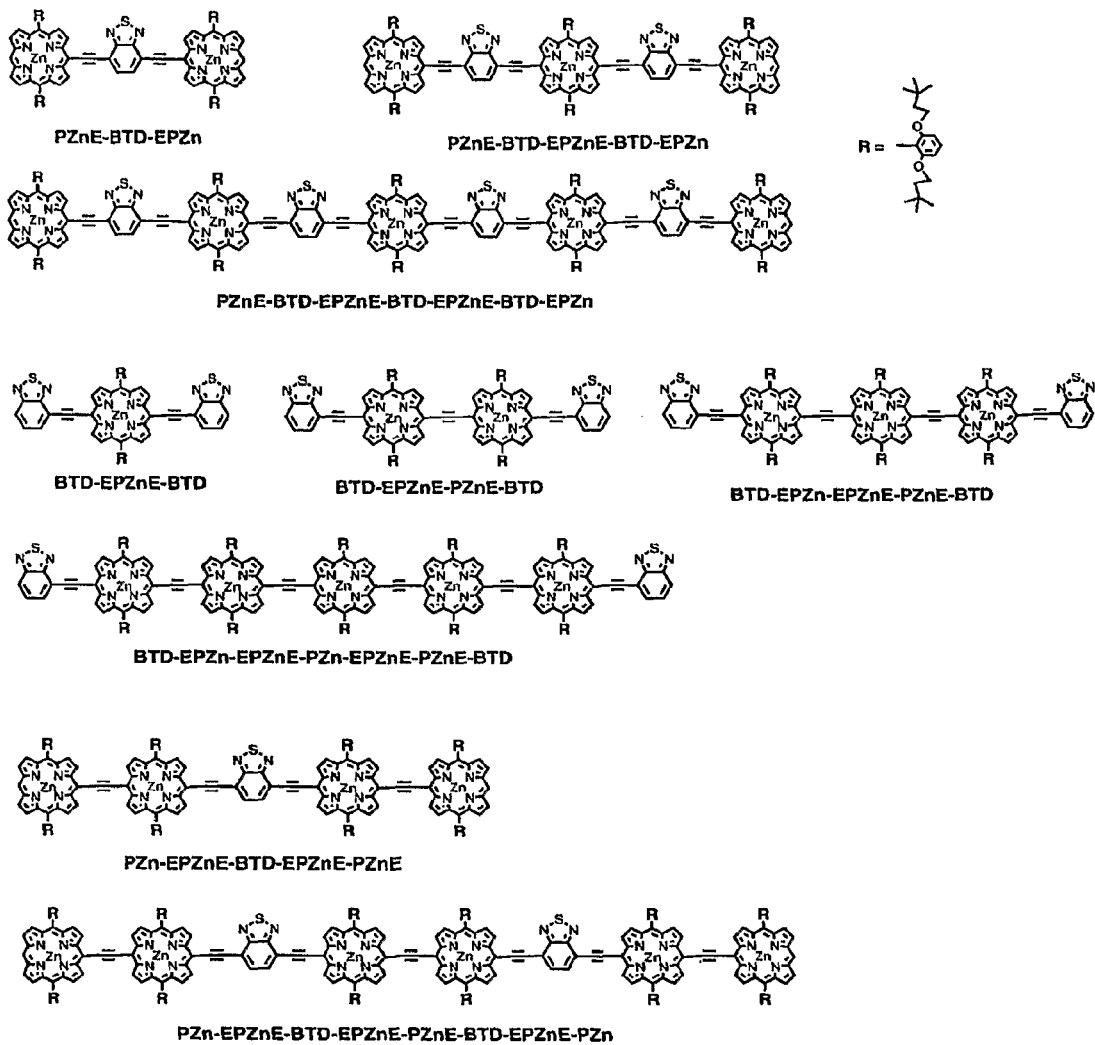
FIG. 14 shows several representative compounds.

The numbers in the following examples refer to the compounds in synthetic schemes depicted in FIGS. 11-13.

Example 44

4,7-Bis[(10,20-bis[2',6'-bis(3",3"-dimethyl-1"-butyloxy)phenyl]porphinato)zinc(II)-5-ylethynyl]benzo[c][1,2,5]thiadiazole (PZnE-BTD-EPZn) (1)

(5-Ethynyl-10,20-bis[2',6'-bis(3,3-dimethyl-1-butyloxy)phenyl]porphinato)zinc(II) (0.100 g, 1.05×10$^{-4}$ mol), and 4,7-dibromobenzo[c][1,2,5]thiadiazole (12.9 mg, 4.4×10$^{-5}$ mol) were charged into a Schlenk flask with Pd$_2$dba$_3$ (12.1 mg, 1.32×10$^{-5}$ mol) and AsPh$_3$ (32.3 g, 1.05×10$^{-4}$ mol). A 9:1 THF:i-Pr$_2$NH (10 ml) solvent mixture was degassed with an Ar purge for 30 min, and transferred to the Schlenk flask. The reaction mixture was stirred at 50° C. overnight, following which the solvent was evaporated, and the residue chromatographed on silica gel using 5:1 hexanes:THF as the eluent. Yield=82 mg (91.6% based on 12.9 mg of the dibromobenzo[c][1,2,5]thiadiazole starting material). $^1$H NMR (500 MHz, CDCl$_3$): δ 10.12 (d, 4H, J=4.4 Hz, β-H), 10.04 (s, 2H, meso-H), 9.21 (d, 4H, J=4.4 Hz, β-H), 9.06 (d, 4H, J=4.5 Hz, β-H), 8.92 (d, 4H, J=4.3 Hz, β-H), 8.37 (s, 2H, Ph-H), 7.74 (t, 4H, J=8.6 Hz, Ph-H), 7.04 (d, 8H, J=8.6 Hz, Ph-H), 3.94 (t, 16H, J=7.2 Hz, —O—CH$_2$—C), 0.87 (t, 16H, J=7.6 Hz, —O—C—CH$_2$—C), 0.24 (s, 72H, —C—CH$_3$).

Example 45

(5-[7'-Bromobenzo[c][1,2,5]thiadiazole-ethyn-4'-yl]-10,20-bis[2',6'-bis(3",3"-dimethyl-1"butyloxy)phenyl]porphinato)zinc(II) (2)

(5-Ethynyl-10,20-bis[2',6'-bis(3,3-dimethyl-1-butyloxy)phenyl]porphinato)zinc(II) (0.100 g, 1.05×10$^{-4}$ mol), and 4,7-dibromobenzo[c][1,2,5]thiadiazole (123.7 mg, 4.21×10$^{-4}$ mol) were charged into a Schlenk Flask with Pd$_2$dba$_3$ (14.4 mg, 1.57×10$^{-5}$ mol) and AsPh$_3$ (38.5 mg, 1.26×10$^{-4}$ mol) A 9:1 THF:i-Pr$_2$NH (10 ml) solvent mixture was degassed with an Ar purge for 30 min and transferred to the Schlenk flask. The reaction mixture was stirred at 50° C. overnight; the solvent was evaporated, and the residue was chromatographed on silica gel using 5:1 hexanes:THF as the eluent. Yield=0.118 g (96.6% based on 12.9 mg of the porphyrin starting material). $^1$H NMR (500 MHz, CDCl$_3$): δ 10.06 (s, 1H, meso-H), 10.01 (d, 2H, J=4.4 Hz, β-H), 9.22 (d, 2H, J=4.4 Hz, β-H), 9.02 (d, 2H, J=4.5 Hz, β-H), 8.91 (d, 2H, J=4.5 Hz, β-H), 8.07 (d, 1H, J=7.4 Hz, Ph-H), 8.01 (d, 1H, J=7.5 Hz, Ph-H), 7.71 (t, 2H, J=8.6 Hz, Ph-H), 7.01 (d, 4H, J=8.6 Hz, Ph-H), 3.90 (t, 8H, J=7.3 Hz, —O—CH$_2$—C), 0.87 (t, 8H, J=7.0 Hz, —O—C—CH$_2$—C), 0.22 (s, 36H, —C—CH$_3$).

Example 46

(5,15-Bis[7'-([10''',20'''-bis[2'''',6''''-bis(3''''',3'''''-dimethyl-1'''''-butyloxy)phenyl]porphinato)zinc(II)-5''-ylethynyl]benzo[c][1,2,5]thiadiazole-ethyn-4'-yl]-10, 20-bis[2',6'-bis(3'',3''-dimethyl-1''butyloxy)phenyl] porphinato)zinc(II) (PZnE-BTD-EPZnE-BTD-EPZn) (3)

Compound 2 (0.100 g, 8.59×10$^{-5}$ mol) and (5,15-diethynyl-10,20-bis[2',6'-bis(3,3-dimethyl-1-butyloxy)phenyl]porphinato)zinc(II) (34.9 mg, 3.58×10$^{-5}$ mol) were charged into a Schlenk flask with Pd$_2$dba$_3$ (9.83 mg, 1.07×10$^{-5}$ mol) and P(o-tol)$_3$ (26.1 mg, 8.59×10$^{-5}$ mol). A 9:1 THF:TEA (10 ml) solvent mixture was degassed with an Ar purge for 30 min and transferred to the Schlenk flask. The reaction mixture was stirred at 60° C. overnight, then poured down a short silica gel column using 49:1 CHCl$_3$:MeOH as the eluent. The product band was isolated, and the residue was subject to gravimetric size exclusion chromatography (BioRad Biobeads, SX-1). The first band was collected, evaporated, and further purified by silica gel chromatography using 49:1 CHCl$_3$:MeOH as the eluent. Yield=114 mg (58% based on (diethynylporphinato) zinc(II) starting material). $^1$H NMR (500 MHz, CDCl$_3$): δ 10.02 (d, 4H, J=4.4 Hz, β-H), 9.94 (d, 4H, J=4.5 Hz, β-H), 9.86 (s, 2H, meso-H), 9.08 (d, 4H, J=4.2 Hz, β-H), 8.96 (d, 4H, J=4.3 Hz, β-H), 8.86 (d, 4H, J=4.5 Hz, β-H), 8.81 (d, 4H, J=4.2 Hz, β-H), 8.26 (s, 4H, Ph-H), 7.70 (t, 6H, J=8.6 Hz, Ph-H), 7.02 (d, 6H, J=4.6 Hz, Ph-H); 7.00 (d, 6H, J=4.7 Hz, Ph-H), 3.89 (m, 24H, —O—CH$_2$—C), 0.87 (m, 24H, —O—C—CH$_2$—C), 0.34 (s, 36H, —C—CH$_3$), 0.30 (s, 72H, —C—CH$_3$).

Example 47

(5,15-Bis[benzo[c][1,2,5]thiadiazole-ethyn-4'-yl]-10, 20-bis[2',6'-bis(3,3-dimethyl-1-butyloxy)phenyl] porphinato)zinc(II) (BTD-EPZnE-BTD) (8)

(5,15-Diethynyl-10,20-bis[2',6'-bis(3,3-dimethyl-1-butyloxy)phenyl]porphinato)zinc(II) (50.0 mg, 5.13×10$^{-5}$ mol) and 4-bromobenzo[c][1,2,5]thiadiazole (26.5 mg, 1.23×10$^{-4}$ mol) were charged into a Schlenk flask with Pd$_2$dba$_3$ (14.1 mg, 1.54×10$^{-5}$ mol) and AsPh$_3$ (37.7 mg, 1.23×10$^{-4}$ mol). 9:1 THF:i-Pr$_2$NH (10 ml) solvent mixture was degassed with an Ar purge for 30 min, and transferred to the Schlenk flask. The reaction mixture was stirred at 50° C. overnight; the solvent was evaporated, and the residue was chromatographed on silica gel using 5:1 hexanes:THF as the eluent. Yield=57.2 mg (90.2% based on 50 mg of the (pophinato)zinc(II) starting material). $^1$H NMR (500 MHz, CDCl$_3$): δ 9.82 (d, 4H, J=4.5 Hz, β-H), 8.85 (d, 4H, J=4.5 Hz, β-H), 7.97 (d, 2H, J=6.4 Hz, Ph-H), 7.68 (t, 2H, J=8.5 Hz, Ph-H), 7.47 (m, 2H, Ph-H), 7.71 (t, 2H, J=8.6 Hz, Ph-H), 6.98 (m, 6H, Ph-H), 3.86 (t, 8H, J=7.3 Hz, —O—CH$_2$—C), 0.77 (t, 8H, J=7.3 Hz, —O—C—CH$_2$—C), 0.19 (s, 36H, —C—CH$_3$).

Example 48

4-(Trimethylsilyl)ethynylbenzo[c][1,2,5]thiadiazole (9)

4-Bromobenzo[c][1,2,5]thiadiazole (0.378 g, 1.76×10$^{-3}$ mol), Pd(PPh$_3$)$_4$ (0.125 g, 1.68×10$^{-4}$ mol), CuI (0.014 g, 7.4×10$^{-5}$ mol), THF (20 ml), diisopropylamine (1.00 ml), and (trimethylsilyl)acetylene (1.00 ml, 7.1×10$^{-3}$ mol) were added to a 50-ml Schlenk tube. N$_2$ was bubbled through the mixture for 5 min, following which the reaction was stirred at 45° C. for 20 h. After cooling, the solvent was evaporated and the residue was chromatographed on silica gel using 1:1 hexanes: CHCl$_3$ as the eluent. Yield=0.398 g (97.3% based on 0.378 g of 4-bromobenzothiadiazole). $^1$H NMR (500 MHz, CDCl$_3$): δ 7.88 (m, 1H, Ph-H), 7.67 (m, 1H, Ph-H), 7.45 (m, 1H, Ph-H), 0.33 (s, 9H, —Si—CH$_3$).

Example 49

4-Ethynylbenzo[c][1,2,5]thiadiazole (10)

4-(Trimethylsilyl)ethynylbenzo[c][1,2,5]-thiadiazole (0.100 g, 4.30×10$^{-4}$ mol), K$_2$CO$_3$ (78.6 mg, 5.71×10$^{-4}$ mol), THF (3 ml), and MeOH (2 ml) were added to a 25-ml Schlenk tube. The mixture was purged with N$_2$ for 5 min, following which the reaction was stirred at room temperature for 1.5 h. The reaction mixture was then filtered, evaporated, and chromatographed on silica gel using 5:1 hexanes:THF as the eluent. Yield=63 g (91.4% based on 0.100 g of 4-(trimethylsilyl)ethynylbenzothiadiazole). $^1$H NMR (500 MHz, CDCl$_3$): δ 8.01 (m, 1H, Ph-H), 7.78 (m, 1H, Ph-H), 7.56 (m, 1H, Ph-H), 3.56 (s, 1H, —CC—H).

Example 50

(5-Bromo-15-[benzo[c][1,2,5]thiadiazole-ethyn-4'-yl]-10,20-bis[2',6'-bis(3'',3''-dimethyl-1''butyloxy) phenyl]porphinato)zinc(II) (11)

(5,15-Dibromo-10,20-bis[2',6'-bis(3,3-dimethyl-1-butyloxy)phenyl]porphinato)zinc(II) (0.100 g, 9.22×10$^{-5}$ mol) and 4-ethynylbenzo[c][1,2,5]thiadiazole (12.3 mg, 7.68×10$^{-5}$ mol) were charged into a Schlenk flask with Pd(PPh$_3$)$_4$ (13.3 mg, 1.15×10$^{-5}$ mol) and CuI (4.4 mg, 2.31×10$^{-4}$ mol). A 9:1 THF:piperidine (10 ml) solvent mixture was degassed with an Ar purge for 30 min, and transferred to the Schlenk flask. The reaction mixture was stirred at 50° C. overnight, evaporated, and chromatographed on silica gel using 5:1 hexanes:THF as the eluent. Yield=0.058 g (64.9% based on the 4-ethynylbenzothiadiazole starting material). $^1$H NMR (500 MHz, CDCl$_3$): δ 9.75 (d, 2H, β-H), 9.57 (d, 2H, J=4.6 Hz, β-H), 8.88 (d, 2H, J=4.5 Hz, β-H), 8.81 (d, 2H, J=4.7 Hz, β-H), 8.00 (m, 1H, Ph-H), 7.69 (t, 2H, J=8.5 Hz, Ph-H), 7.56 (m, 1H, Ph-H), 7.29 (m, 1H, Ph-H), 6.98 (d, 4H, J=8.6 Hz, Ph-H), 3.88 (t, 8H, J=7.4 Hz, —O—CH$_2$—C), 0.87 (t, 8H, J=7.3 Hz, —O—C—CH$_2$—C), 0.24 (s, 36H, —C—CH$_3$).

Example 51

(5-Triisopropylsilylethynyl-15-[benzo[c][1,2,5]thiadiazole-ethyn-4'-yl]-10,20-bis[2',6'-bis(3'',3''-dimethyl-1''butyloxy)phenyl]porphinato)zinc(II) (12)

(5-Bromo-15-triisopropylsilylethynyl-10,20-bis[2',6'-bis (3,3-dimethyl-1-butyloxy)phenyl]porphinato)zinc(II) (0.200 g, 1.69×10$^{-4}$ mol) and 4-ethynylbenzo[c][1,2,5]thiadiazole (32.5 mg, 2.03×10$^{-4}$ mol) were charged into a Schlenk flask with Pd(PPh$_3$)$_4$ (29.3 mg, 2.53×10$^{-5}$ mol) and CuI (9.6 mg, 5.06×10$^{-5}$ mol). A 9:1 THF:piperidine (10 ml) solvent mixture was degassed with an Ar purge for 30 min, and transferred to the Schlenk falsk. The reaction mixture was stirred at 50° C. overnight, evaporated, and chromatographed on silica gel using 5:1 hexanes:THF as the eluent. Yield=164.4 mg (76.8% based on the porphyrin starting material). $^1$H NMR (500 MHz, CDCl$_3$): δ 9.87 (d, 2H, β-H), 9.61 (d, 2H, J=4.5 Hz, β-H), 8.86 (d, 2H, J=4.5 Hz, β-H), 8.80 (d, 2H, J=4.5 Hz, β-H), 8.07 (m, 1H, Ph-H), 7.67 (t, 2H, J=8.5 Hz, Ph-H), 7.60 (m, 1H, Ph-H), 7.49 (m, 1H, Ph-H), 6.98 (d, 4H, J=8.5 Hz, Ph-H), 3.88 (t, 8H, J=7.4 Hz, —O—CH$_2$—C), 1.41 (m, 21H, —Si—(CH(CH$_3$)$_2$)$_3$), 0.88 (t, 8H, J=7.3 Hz, —O—C—CH$_2$—C), 0.27 (s, 36H, —C—CH$_3$).

Example 52

(5-Ethynyl-15-[benzo[c][1,2,5]thiadiazole-ethyn-4'-yl]-10,20-bis[2',6'-bis(3",3"-dimethyl-1"butyloxy)phenyl]porphinato)zinc(II) (13)

Compound 12 (160 mg, 1.26×10$^{-4}$ mol) was dissolved in THF under Ar. TBAF (2.5 mL, 0.1 M in THF, 2.5×10$^{-4}$ mol) was then added dropwise and the reaction mixture was stirred for 5 min at room temperature. TLC analysis (5:1 hexanes: THF) showed complete formation of the product and consumption of the starting material. The reaction mixture was then quenched with 10 ml of water, extracted with CHCl$_3$, and evaporated. The residue was chromatographed on silica gel using 5:1 hexanes:THF as the eluent. Yield=125.5 mg (89.5% based on compound 12). $^1$H NMR (500 MHz, CDCl$_3$): δ 9.86 (d, 2H, β-H), 9.57 (d, 2H, J=4.1 Hz, β-H), 8.85 (d, 2H, J=4.8 Hz, β-H), 8.81 (d, 2H, J=4.5 Hz, β-H), 8.03 (m, 1H, Ph-H), 7.69 (t, 2H, J=8.5 Hz, Ph-H), 7.56 (m, 1H, Ph-H), 7.49 (m, 1H, Ph-H), 6.98 (m, 5H, Ph-H), 4.07 (S, 1H, —CC—H), 3.88 (t, 8H, J=7.4 Hz, —O—CH$_2$—C), 0.87 (t, 8H, J=6.8 Hz, —O—C—CH$_2$—C), 0.29 (s, 36H, —C—CH$_3$).

Example 53

1,2-Bis[(15-(benzo[c][1,2,5]thiadiazole-ethyn-4'-yl)-10,20-bis[3',5'-bis(3",3"-dimethyl-1"butyloxy)phenyl]porphinato)zinc(II)-5-yl]ethyne (BTD-EPZnE-PZnE-BTD) (14)

Compound 11 (50.0 mg, 4.30×10$^{-5}$ mol) and compound 13 (57.0 mg, 5.16×10$^{-5}$ mol) were charged into a Schlenk flask with Pd$_2$dba$_3$ (5.9 mg, 6.45×10$^{-6}$ mol) and AsPh$_3$ (15.8 mg, 5.16×10$^{-5}$ mol). A 9:1 THF:TEA (10 ml) solvent mixture was degassed with an Ar purge for 30 min, and transferred to the Schlenk flask. The reaction mixture was stirred at 60° C. overnight, poured down a short silica gel column using 49:1 CHCl$_3$:MeOH as the eluent. The product band was collected, evaporated, taken up in THF, and purified via size exclusion chromatography (BioRad Biobeads, SX-1). The first band was collected, evaporated, and further purified by silica gel chromatography using 49:1 CHCl$_3$:MeOH as the eluent. Yield=45 mg (47.8% based on 50 mg of compound 11), $^1$H NMR (500 MHz, CDCl$_3$): δ 10.19 (d, 4H, J=4.4 Hz, β-H), 9.85 (d, 4H, J=4.3 Hz, β-H), 8.88 (d, 4H, J=4.4 Hz, β-H), 8.84 (d, 4H, J=4.5 Hz, β-H), 8.10 (d, 2H, J=6.1 Hz, Ph-H), 8.37 (m, 4H, Ph-H), 7.66 (t, 8H, J=8.6 Hz, Ph-H), 7.00 (d, 8H, J=8.6 Hz, Ph-H), 3.89 (t, 16H, J=7.5 Hz, —O—CH$_2$—C), 0.82 (t, 16H, J=6.6 Hz, —O—C—CH$_2$—C), 0.32 (s, 72H, —C—CH$_3$).

Example 54

(5,15-Bis[15'-benzo[c][1,2,5]thiadiazole-ethyn-4'-yl-(10''',20'''-bis[2'''',6''''-bis(3''''',3'''''-dimethyl-1'''''-butyloxy)phenyl]porphinato)zinc(II)ethyn-5'-yl]-10,20-bis[2',6'-bis(3'',3''-dimethyl-1''butyloxy)phenyl]porphinato)zinc(II)(BTD-EPZnE-PZn-EPZnE-BTD) (15)

Compound 13 (60 mg, 5.42×10$^{-5}$ mol) and (5,15-dibromo-10,20-bis[2',6'-bis(3,3-dimethyl-1-butyloxy)phenyl]porphinato)zinc(II) (24.5 mg, 2.26×10$^{-5}$ mol) were charged into a Schlenk flask with Pd$_2$dba$_3$ (6.2 mg, 6.78×10$^{-6}$ mol) and P(o-tol)$_3$ (16.5 mg, 5.42×10$^{-5}$ mol). A 9:1 THF:TEA (10 ml) solvent mixture was degassed with an Ar purge for 30 min and transferred to the Schlenk flask. The reaction mixture was stirred at 60° C. overnight, following which it chromatographed on using 49:1 CHCl$_3$:MeOH as the eluent. The product band was collected, evaporated, taken up in THF, and purified via size exclusion chromatography (BioRad Biobeads, SX-1). The first band was collected, evaporated, and further purified by silica gel chromatography using 49:1 CHCl$_3$:MeOH as the eluent. Yield=48.4 mg (68.2% based on the (dibromoporphinato)zinc(II) starting material). $^1$H NMR (500 MHz, CDCl$_3$): δ 10.16 (d, 4H, J=4.4 Hz, β-H), 10.14 (d, 4H, J=4.3 Hz, β-H), 9.81 (d, 4H, J=4.4 Hz, β-H), 8.87 (d, 4H, J=4.4 Hz, β-H), 8.85 (d, 4H, J=4.4 Hz, β-H), 8.81 (d, 4H, J=4.4 Hz, β-H), 8.02 (d, 2H, J=6.0 Hz, Ph-H), 7.90 (d, 2H, J=8.7 Hz, Ph-H), 7.63 (m, 8H, Ph-H), 6.96 (m, 12H, J=4.6 Hz, Ph-H), 3.89 (m, 24H, —O—CH$_2$—C), 0.81 (m, 24H, —O—C—CH$_2$—C), 0.28 (s, 36H, —C—CH$_3$), 0.26 (s, 72H, —C—CH$_3$).

Example 55

(5,15-Bis[(15'-triisopropylsilylethynyl-10',20'-bis[2''',6'''-bis(3'''',3''''-dimethyl-1''''butyloxy)phenyl]porphinato)zinc(II)ethyn-5'-yl]-10,20-bis[2',6'-bis(3'',3''-dimethyl-1''butyloxy)phenyl]porphinato)zinc(II) (16)

(5-Bromo-15-triisopropylsilylethynyl-10,20-bis[2',6'-bis(3'',3''-dimethyl-1''butyloxy)phenyl]porphinato)zinc(II) (120 mg, 1.01×10$^{-4}$ mol) and (5,15-diethynyl-10,20-bis[2',6'-bis(3'',3''dimethyl-1''-butyloxy)phenyl]porphinato)zinc (II) (41.1 mg, 4.21×10$^{-5}$ mols) were charged into a Schlenk flask with AsPh$_3$ (30.9 mg, 1.01×10$^{-4}$ mols) and Pd$_2$dba$_3$ (11.6 mg, 1.26×10$^{-5}$ mol). A 9:1 THF:TEA (10 mL) solvent mixture was degassed with an Ar purge for 30 min, and transferred to the reaction flask. The reaction mixture was stirred at 60° C. under Ar overnight, and chromatographed on silica using 49:1 CHCl$_3$:MeOH as the eluent. The product band was collected, evaporated, taken up in THF, and purified via size exclusion chromatography (BioRad Biobeads, SX-1). The first band was collected, evaporated, and further purified by silica gel chromatography using 49:1 CHCl$_3$:MeOH as the eluent. Yield=114 mg (85% based on diethynyl starting material). $^1$H NMR (500 MHz, CDCl$_3$): δ 10.35 (d, 8H, δ-H), 9.64 (d, 4H, δ-H), 9.01 (d, 8H, δ-H), 8.86 (d, 4H, δ-H), 7.72 (d, 6H, δ-H), 7.05 (d, 12H, J=4.6 Hz, Ph-H), 3.98 (m, 24H, —O—CH$_2$—C), 0.89 (m, 24H, —O—C—CH$_2$—C), 0.40 (s, 36H, —C—CH$_3$), 0.37 (s, 72H, —C—CH$_3$).

Example 56

(5,15-Bis[(15'-ethynyl-10',20'-bis[2''',6'''-bis(3'''',3''''-dimethyl-1''''''butyloxy)phenyl]porphinato)zinc(II) ethyn-5'-yl]-10,20-bis[2',6'-bis(3'',3''-dimethyl-1''-butyloxy)phenyl]porphinato)zinc(II) (17)

Compound 16 (114 mg, $3.58 \times 10^{-5}$ mol) was dissolved in THF and cooled to 0° C. under Ar. TBAF (0.716 mL, 0.1 M in THF, $7.16 \times 10^{-5}$ mol) was then added dropwise, and the reaction mixture was stirred for 15 min at 0° C. The mixture was then poured directly onto a short silica gel column and chromatographed using $CHCl_3$ as the eluent. Yield=101.2 mg (98.4% based on compound 16).

Example 57

[5,15-Bis(15'''-[(15''''''-benzo[c][1,2,5]thiadiazole-ethyn-4''''''-yl-10'''''',20''''''-bis[2'''''',6''''''-bis(3''''''',3'''''''dimethyl-1'''''''-butyloxy)phenyl]porphinato) zinc(II)-ethyn-5''''''-yl]-10',20'-bis[2''',6'''-bis(3'''',3''''-dimethyl-1''''''-butyloxy)phenyl]porphinato)zinc (II)-ethyn-5'''-yl)-10,20-bis[2',6'-bis(3'',3''-dimethyl-1''-butyloxy)phenyl]phenyl]porphinato]zinc(II) (BTD-EPZnE-PZn-EPZnE-PZn-EPZnE-BTD) (18).

Compound 11 (50 mg, $4.13 \times 10^{-5}$ mol) and compound 17 (47.4 mg, $1.65 \times 10^{-5}$ mol) were charged into a Schlenk flask with $Pd_2dba_3$ (5.7 mg, $4.95 \times 10^{-6}$ mol) and $AsPh_3$ (12.1 mg, $3.96 \times 10^{-5}$ mol). A 9:1 THF:TEA solvent mixture was degassed with an Ar purge for 30 min and transferred to the Schlenk flask. The reaction mixture was stirred at 60° C. overnight, and chromatographed on silica using 49:1 $CHCl_3$:MeOH as the eluent. The product band was collected, evaporated, taken up in THF, and purified via size exclusion chromatography (BioRad Biobeads, SX-1). The first band was collected, evaporated, and further purified by silica gel chromatography using 49:1 $CHCl_3$:MeOH as the eluent. Yield=55 mg (68.2% based on compound 17). $^1$H NMR (500 MHz, $CDCl_3$): δ 10.39 (m, 8H, β-H), 10.35 (m, 8H, β-H), 9.84 (d, 4H, β-H), 9.04 (m, 16H, β-H), 8.88 (d, 4H, β-H), 7.77 (d, 2H, Ph-H), 7.74 (m, 12H, Ph-H), 7.55 (d, 2H, Ph-H), 7.07 (m, 20H, Ph-H), 4.03 (m, 40H, —O—$CH_2$—C), 0.89 (m, 40H, —O—C—$CH_2$—C), 0.38 (m, 180H, —C—$CH_3$).

Example 58

(5-Triisopropylsilylethynyl-15-[10',20'-bis[2''',6'''-bis(3'''',3''''-dimethyl-1''''''butyloxy)phenyl]porphinato) zinc(II)-ethyn-5'-yl]-10,20-bis[2',6'-bis(3'',3''-dimethyl-1''butyloxy)phenyl]porphinato)zinc(II) (19)

(5-Bromo-15-triisopropylsilylethynyl-10,20-bis[2',6'-bis (3,3-dimethyl-1-butyloxy)phenyl]porphinato)zinc(II) (50 mg, $5.26 \times 10^{-5}$ mol) and (5-triisopropylsilylethynyl-10,20-bis[2',6'-bis(3,3-dimethyl-1-butyloxy)phenyl]porphinato) zinc(II) (74.8 mg, $6.31 \times 10^{-5}$ mol) were charged into a Schlenk flask with $Pd_2dba_3$ (7.2 mg, $7.89 \times 10^{-6}$ mol) and $AsPh_3$ (19.2 mg, $6.31 \times 10^{-5}$ mol). A 9:1 THF:TEA (10 ml) solvent mixture was degassed with an Ar purge for 30 min and transferred to the Schlenk flask. The reaction mixture was stirred at 60° C. overnight, and chromatographed on silica using 49:1 $CHCl_3$:MeOH as the eluent. The product band was collected, evaporated, taken up in THF, and purified via size exclusion chromatography (BioRad Biobeads, SX-1). The first band was collected, evaporated, and further purified by silica gel chromatography using 49:1 $CHCl_3$:MeOH as the eluent. Yield=82 mg (75.8% based on the 50 mg of the [5-bromo-15-triisopropylsilylethynylporphinato]zinc(II) starting material). $^1$H NMR (500 MHz, $CDCl_3$): δ10.43 (d, 2H, J=4.6 Hz, β-H), 10.42 (d, 2H, J=4.4 Hz, β-H), 10.03 (s, 1H, meso-H), 9.65 (d, 2H, J= 4.5 Hz, β-H), 9.23 (d, 2H, J=4.4 Hz, β-H), 9.10 (d, 2H, J=4.6 Hz, β-H), 8.99 (d, 2H, J=4.4 Hz, β-H), 8.95 (d, 2H, J=4.4 Hz, β-H), 8.86 (d, 2H, J=4.4 Hz, β-H), 7.73 (m, 4H, Ph-H), 7.05 (m, 8H, Ph-H), 3.98 (m, 16H, —O—$CH_2$—C), 0.89 (m, 16H, —O—C—$CH_2$—C), 0.45 (s, 36H, —C—$CH_3$), 0.42 (s, 36H, —C—$CH_3$).

Example 59

(5-Ethynyl-15-[1040 ,20'-bis[2''',6'''-bis(3'''',3''''-dimethyl-1''''''butyloxy)phenyl]porphinato)zinc(II)-ethyn-5'-yl]-10,20-bis[2',6'-bis(3'',3''-dimethyl-1''butyloxy) phenyl]porphinato)zinc(II) (20)

Compound 19 (80 mg, $3.89 \times 10^{-5}$ mol) was dissolved in THF and cooled to 0° C. under Ar. TBAF (0.778 mL, 0.1 M in THF, $7.78 \times 10^{-5}$ mol) was then added dropwise and the reaction mixture was stirred for 15 min at 0° C. The reaction mixture was then poured directly onto a silica gel column and chromatographed using $CHCl_3$ as the eluent. Yield=65 mg (87.9% based on compound 16).

Example 60

4,7-Diiodobenzo[c][1,2,5]thiadiazole (21)

Benzo[c][1,2,5]thiadiazole (3.20 g, $2.35 \times 10^{-2}$ mol), $I_2$ (13.2 g, $5.20 \times 10^{-2}$ mol), and $Ag_2SO_4$ (7.34 g, $2.35 \times 10^{-2}$ mol) were added to a 100-mL three neck round bottom flask. Concentrated $H_2SO_4$ (35 mL) was added, and the reaction mixture was stirred at 110° C. for 14 h under $N_2$. After cooling to ambient temperature, the reaction mixture was poured into ice water, and the precipitate was collected by filtration. This material was washed with $CHCl_3$, following which the filtrated was washed thrice successively with saturated aq $NaHSO_3$ and brine, and dried over $Na_2SO_4$. The product was chromatographed on silica using 1:1 hexanes:$CHCl_3$ as the eluent. Yield=3.95 g (43.3% based on 3.20 g of benzothiadiazole). $^1$H NMR (500 MHz, $CDCl_3$): δ 7.75 (s, 12H, Ph-H).

Example 61

4,7-Bis[(15-(10',20'-bis[2'',6''-bis(3''',3'''-dimethyl-'''-butyloxy)phenyl]porphinato)zinc(II)ethyn-5'-yl)-10, 20-bis[2',6'-bis(3'',3''-dimethyl-1'''-butyloxy)phenyl] porphinato)zinc(II)-5-ylethynyl]benzo[c][1,2,5] thiadiazole(PZn-EPZnE-BTD-EPZnE-PZn) (22).

Compound 20 (50.0 mg, $2.63 \times 10^{-5}$ mol) and compound 21 (4.27 mg, $1.10 \times 10^{-6}$ mol) were charged into a Schlenk Flask with $Pd_2dba_3$ (3.03 mg, $3.31 \times 10^{-7}$ mol) and $AsPh_3$ (8.05 g, $2.63 \times 10^{-5}$ mol). A 9:1 THF:$iPr_2NH$ (10 ml) solvent mixture was degassed with an Ar purge for 30 min and transferred to the Schlenk flask. The reaction mixture was stirred at 60° C. overnight under Ar, and chromatographed on silica using 49:1 CHCl$_3$:MeOH as the eluent. The product band was collected, evaporated, taken up in THF, and purified via size exclusion chromatography (BioRad Biobeads, SX-1). The first band was collected, evaporated, and further purified by silica gel chromatography using 49:1 CHCl$_3$:MeOH as the eluent. Yield=35 mg (80.6% based on 4.27 mg of compound 21). $^1$H NMR (500 MHz, THF-d8): δ 10.33 (d, 4H, J=7.3 Hz, β-H), 10.28 (d, 4H, J=7.0 Hz, β-H), 10.07 (d, 4H, J=8.3 Hz, β-H), 9.90 (s, 2H, meso-H), 9.13 (d, 4H, J=7.0 Hz, β-H), 9.06 (d, 4H, J=7.4 Hz, β-H), 8.94 (m, 8H, β-H), 8.88 (d, 4H, J=4.2 Hz, β-H), 8.40 (s, 2H, Ph-H), 7.79 (m, 8H, Ph-H), 7.17 (m, 16H, Ph-H), 4.01 (m, 32H, —O—CH$_2$—C), 0.87 (m, 32H, —O—C—CH$_2$—C), 0.41 (d, 72H, J=5.2 Hz, —C—CH$_3$), 0.36 (d, 72H, J=5.1 Hz, —C—CH$_3$).

Example 62

1,2-Bis[(15-triisopropylsilylethynyl-10,20-bis[2',6'-bis(3",3"-dimethyl-1"butyloxy)phenyl]porphinato)zinc(II)-5-yl]ethyne (23)

(5-Bromo-15-triisopropylsilylethynyl-10,20-bis[2',6'-bis(3",3"-dimethyl-1"butyloxy)phenyl]porphinato)zinc(II) (150 mg, 1.26×10$^{-4}$ mol) and (5-ethynyl-15-triisopropylsilylethynyl-10,20-bis[2',6'-bis(3",3"-dimethyl-1"butyloxy) phenyl]porphinato)zinc(II) (106 mg, 9.40×10$^{-5}$ mol) were charged into a Schlenk flask with AsPh$_3$ (46.3 mg, 1.51×10$^{-4}$ mols) and Pd$_2$dba$_3$ (17 mg, 1.89×10$^{-5}$ mol). A 9:1 THF:TEA (10 mL) solvent mixture was degassed with an Ar purge for 30 min and then transferred to the reaction flask. The reaction mixture was stirred at 60° C. overnight, and chromatographed on silica using 49:1 CHCl$_3$:MeOH as the eluent. The product band was collected, evaporated, taken up in THF, and purified via size exclusion chromatography (BioRad Biobeads, SX-1). The first band was collected, evaporated, and further purified by silica gel chromatography using 49:1 CHCl$_3$:MeOH as the eluent. Yield=164 mg (78.1% based on 106 mg of the (5-ethynyl-15-triisopropylsilylethynylporphinato)zinc (II) starting material). $^1$H NMR (500 MHz, CDCl$_3$): δ 10.36 (d, 4H, /3-H), 9.67 (d, 4H, β-H), 9.00 (d, 4H, /3-H), 8.88 (d, 4H, β-H), 7.75 (m, 4H, Ph-H), 7.06 (m, 8H, Ph-H), 3.98 (m, 16H, —O—CH$_2$—C), 1.46 (m, 21H, —SiCH(CH$_3$)$_2$), 0.91 (m, 16H, —O—C—CH$_2$-Q, 0.38 (d, 72H, —C—CH$_3$).

Example 63

1,2-Bis[(15-ethynyl-10,20-bis[2',6'-bis(3",3"-dimethyl-1"butyloxy)phenyl]porphinato)zinc(II)-5-yl]ethyne (24)

Compound 23 (150 mg, 6.71×10$^{-5}$ mol) was charged in a Schlenk flask, dissolved in THF, and cooled to 0° C. under Ar. Tetrabutylammonium fluoride (TBAF) (1.34 mL, 0.1 M in THF, 1.34×10$^{-4}$ mol) was added dropwise to the reaction mixture and stirred for 15 min at 0° C. After 15 min, the reaction mixture was poured down a pre-packed silica gel plug and eluted with CHCl$_3$. Yield=115 mg (89.1% based on compound 23).

Example 64

(5-(10',20'-Bis[2",6"-bis(3"',3"'-dimethyl-1"'butyloxy)phenyl]porphinato)zinc(II)-ethyn-5'-yl)-15-[7'-bromobenzo[c][1,2]thiadiazole-ethyn-4'-yl]-10,20-bis[2',6'-bis(3",3"-dimethyl-1"butyloxy)phenyl]porphinato)zinc(II) (25)

Compound 20 (0.200 g, 1.05×10$^{-4}$ mol) and 4,7-dibromobenzo[c][1,2,5]thiadiazole (123.8 mg, 4.21×10$^{-4}$ mol) were charged into a Schlenk flask with Pd$_2$dba$_3$ (14.4 mg, 1.57×10$^{-5}$ mol) and AsPh$_3$ (38.6 mg, 1.26×10$^{-4}$ mol). A 9:1 THF:TEA (10 ml) solvent mixture was degassed with an Ar purge for 30 min and transferred to the flask. The reaction mixture was stirred at 50° C. overnight and chromatographed on silica using 49:1 CHCl$_3$:MeOH as the eluent. The product band was collected, evaporated, taken up in THF, and purified via size exclusion chromatography (BioRad Biobeads, SX-1). The second band was collected, evaporated, and further purified by silica gel chromatography using 49:1 CHCl$_3$:MeOH as the eluent. Yield=108 mg (48.7% based on 0.200 mg of the porphyrinic starting material). $^1$H NMR (500 MHz, CDCl$_3$): δ 10.45 (m, 4H, β-H), 10.38 (d, 2H, J=4.2 Hz, β-H), 10.07 (s, 1H, meso-H), 9.95 (d, 2H, J=4.2 Hz, β-H), 9.26 (d, 2H, J=4.3 Hz, β-H), 9.13 (d, 2H, J=4.3 Hz, β-H), 9.01 (d, 2H, J=4.4 Hz, β-H), 8.97 (m, 4H, β-H), 8.03 (m, 2H, Ph-H), 7.75 (m, 5H, Ph-H), 7.08 (m, 8H, Ph-H), 3.98 (m, 16H, —O—CH$_2$—C), 0.91 (m, 16H, —O—C—CH$_2$—C), 0.41 (s, 36H, —C—CH$_3$), 0.35 (s, 36H, —C—CH$_3$).

Example 65

Comparative Electrochemistry

The following table shows the comparative electrochemistry of conjugated porphyrin compounds. Cyclic voltammetric experimental conditions: solvent=CH$_2$Cl$_2$; [TBAPF$_6$]= 0.10 M; scan rate=200 mV/s; reference electrode=SCE; working electrode=Pt disk. All potentials are reported relative to the ferrocene/ferrocenium redox couple, which was used as an internal standard in these experiments.

| Compound | $E_{1/2}^{ox}$ | $E_{1/2}^{red}$ |
|---|---|---|
| PZnE-BTD-EPZn | 0.27 | −1.61 |
|  |  | −1.75 |
|  |  | −2.12 |
| PZnE-BTD-EPZnE-BTD-EPZn | 0.07 | −1.51 |
|  |  | −1.72 |
| BTD-EPZnE-BTD | 0.32 | −1.55 |
|  | 0.79 | −1.75 |
| BTD-EPZnE-PZnE-BTD | 0.06 | −1.64 |
|  | 0.34 | −1.88 |
|  | 0.88 |  |
| BTD-EPZnE-PZn-EPZnE-BTD | 0.06 | −1.68 |
|  | 0.30 | −1.85 |
|  | 0.58 | −1.96 |
|  |  | −2.11 |

Example 66

Comparative Integrated Oscillator Strengths

The following table shows the comparative integrated oscillator strengths and absorptive domains of the blue and red spectral regions of the conjugated porphyrin compounds.

| Compound | FWHM[b] B-band region [cm$^{-1}$, (nm)] | Oscillator Strength B-band region[d] | FWHM[c] Q-band region [cm$^{-1}$, (nm)] | Oscillator Strength Q-band region[f] | Total Oscillator Strength[g] |
|---|---|---|---|---|---|
| PZnE-BTD-EPZn | 2770 (425) | 2.39 | 1094 (689) | 1.01 | 4.10 |
| PZnE-BTD-EPZnE-BTD-EPZn | 2341 (428) | 3.08 | 1427 (752) | 1.05 | 5.10 |
| BTD-EPZnE-BTD | 1912 (469) | 1.88 | 682 (674) | 0.34 | 2.81 |
| BTD-EPZnE-PZnE-BTD | 2772 (495) | 3.56 | 1700 (765) | 0.88 | 4.44 |
| BTD-EPZnE-PZn-EPZnE-BTD | 4621 (492) | 3.56 | 1679 (811) | 0.82 | 4.38 |

[a]From electronic absorption spectra recorded in THF solvent.
[b]Taken as twice value of half the spectral width of the B-band region at half the height of the absorption noted.
[c]Oscillator strengths calculated over the following wavelength domains: PZnE-BTD-EPZn (380~520 nm); PZnE-BTD-EPZnE-BTD-EPZn (380~510 nm); BTD-EPZnE-BTD (380~550 nm); BTD-EPZnE-PZnE-BTD (360~560 nm); BTD-EPZnE-PZn-EPZnE-BTD (360~560 nm).
[d]Entries correspond to the spectral breadth of the transition envelope centered at the wavelength in parentheses.
[e]Oscillator strengths calculated over the following wavelength domains: PZnE-BTD-EPZn (520~850 nm); PZnE-BTD-EPZnE-BTD-EPZn (510~790 nm); BTD-EPZnE-BTD (550~730 nm); BTD-EPZnE-PZnE-BTD (560~840 nm); BTD-EPZnE-PZn-EPZnE-BTD (560~900 nm).
[f]Oscillator strengths calculated over the following wavelength domains: PZnE-BTD-EPZn (300~850 nm); PZnE-BTD-EPZnE-BTD-EPZn (300~790 nm); BTD-EPZnE-BTD (300~730 nm); BTD-EPZnE-PZnE-BTD (300~840 nm); BTD-EPZnE-PZn-EpZnE-BTD (300~900 nm).

Example 67

Prominent Absorption Band Wavelength, Energies, and Extinction Coefficients of Conjugated Porphyrin Compounds in THF Solvent The following table shows the prominent absorption band wavelength, energies, and extinction coefficients of conjugated porphyrin compounds in THF solvent.

| | region | | | | | | | | |
|---|---|---|---|---|---|---|---|---|---|
| | UV-region | | | B-band region | | | Q-band | | |
| | λ (nm) | ν (cm$^{-1}$) | Log (ε) | λ (nm) | ν (cm$^{-1}$) | Log (ε) | λ (nm) | ν (cm$^{-1}$) | Log (ε) |
| PZnE-BTD-EPZn | 311 | 32,154 | (4.60) | 425 | 23,529 | (5.35) | 526 | 19,011 | (4.73) |
| | | | | | | | 561 | 17,825 | (4.52) |
| | | | | | | | 689 | 14,514 | (4.94) |
| PZnE-BTD-EPZnE-BTD-EPZn | 310 | 32,258 | (4.45) | 428 | 23,364 | (5.20) | 525 | 19,047 | (4.71) |
| | | | | | | | 632 | 15,823 | (4.22) |
| | | | | | | | 752 | 13,298 | (5.01) |
| BTD-EPZnE-BTD | 314 | 31,847 | (4.45) | 469 | 21,321 | (5.21) | 592 | 16,892 | (3.85) |
| | 322 | 31,056 | (4.48) | | | | 674 | 14,837 | (4.91) |
| BTD-EPZnE-PZuE-BTD | 308 | 32,467 | (4.60) | 468 | 21,367 | (5.20) | 584 | 17,123 | (4.26) |
| | | | | 495 | 20,202 | (5.40) | 765 | 13,072 | (5.04) |
| BTD-EPZnE-PZn-EPZNE-BTD | 308 | 32,467 | (4.49) | 492 | 20,325 | (5.20) | 588 | 17,007 | (4.10) |
| | 323 | 30,960 | (4.47) | | | | 620 | 16,129 | (4.03) |
| | | | | | | | 811 | 12,330 | (4.94) |

Example 68

Spectroscopic Parameters of the Porphyrin Compounds in THF Solvent

The following table shows spectroscopic parameters of the porphyrin compounds in THF solvent.

| Compound | λmax ($S_0 \rightarrow S_1$) [nm][a] | $\epsilon_g$ @ λmax($S_0 \rightarrow S_1$) [$M^{-1} cm^{-1}$] | λmax ($S_1 \rightarrow S_0$) [nm][a] | $\phi_f^b$ | λmax ($S_1 \rightarrow S_n$) [nm][a,c] | $\tau_F^d$ (τ0)[e] [ns] |
|---|---|---|---|---|---|---|
| PZnE-BTD-EPZn | 689 (1094) | 121 000 | 741 (1648) | 0.37 (0.015) | | |
| PZnE-BTD-EPZnE-BTD-EPZn | 752 (1427) | 112 000 | 784 (995) | 0.36 (0.015) | | 1.26 |
| BTD-EPZnE-BTD | 674 (682) | 81 000 | 687 (723) | 0.17 (0.005) | | |
| BTD-EPZnE-PZnE-BTD | 765 (1700) | 109 000 | 787 (789) | 0.33 (0.006) | | 1.61 |
| BTD-EPZnE-PZn-EPZNE-BTD | 811 (1679) | 87 000 | 846 (880) | 0.25 (0.015) | | 0.86 |

[a]Numbers in parentheses are spectral breadths (fwhm) of the respective transitions in units of $cm^{-1}$.
[b]Quantum yields were determined relative to H$_2$TPP in benzene ($\Phi_f$= 0.13) (Quimby, D. J.; Longo, F. R. J. Am. Chem. Soc. 1975, 97, 5111-5117.), parenthetical values represent standard deviations from the mean.
[c]Excited state λmax values were determined by FTAS 300fs after photoexcitation.
[d]Determined via TCSPC.
[e]Parenthetical values are natural radiative lifetimes calculated by the Strickler-Berrg method (Strickler, S. J.; Berg, R. A. J. Chem. Phys. 1962, 37, 814-820)

All patents, patent applications, and publications referenced in this application are incorporated herein in their entirety.

What is claimed:

1. A compound, oligomer, or polymer that contains:

PM-(Sp-PQ-Sp-PM)$_n$, wherein:
n is an integer greater than or equal to 1;
PM is a (porphinato)(metal) moiety;
Sp is ethynyl;
PQ is

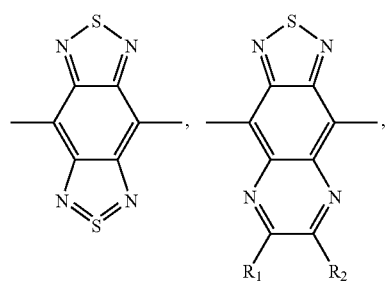

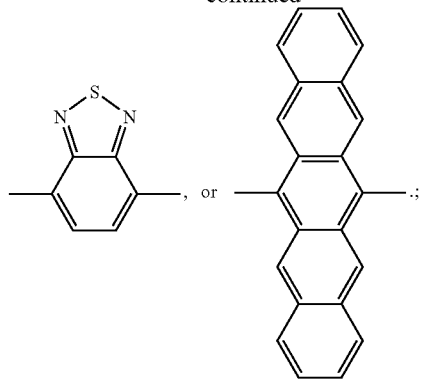

where "-" indicates points of attachment;

and R$_1$ and R$_2$ are H, C$_1$-C$_{12}$ alkyl, alkoxy, aryl, or glycol.

2. The compound, oligomer, or polymer of claim 1 wherein PQ is

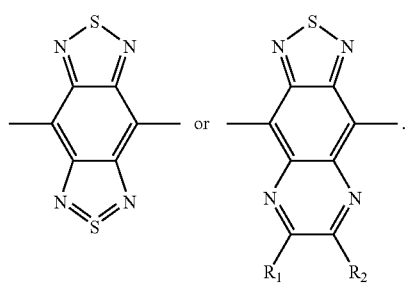

3. The compound, oligomer, or polymer of claim 1 wherein PM is a (porphinato)zinc(II) moiety.

4. The compound, oligomer, or polymer of claim 1 wherein n is 1 or 2.

5. The compound, oligomer, or polymer of claim 1 where Sp-PM is [(10,20-bis[2',6'-bis(3,3-dimethyl-1-butyloxy)phenyl]porphinato)zinc(II)-5-ylethynyl; [(10,20-bis[aryl]porphinato)metal-5-ylethynyl; [(10,20-bis[alkyl]porphinato)metal-5-ylethynyl; [(10,20-bis[alkoxy]porphinato)metal-5-ylethynyl; or a [(10,20-bis[alkyl]porphinato)metal-5-ylethynyl, [(10,20-bis[alkoxy]porphinato)metal-5-ylethynyl, or [(10,20-bis[aryl]porphinato)metal-5-ylethynyl moiety that bears net charge.

6. The compound, oligomer, or polymer of claim 1 wherein PM is ethynyl-10-20-bis(2',6'-bis(3,3-dimethyl)-butoxy)phenyl]porphinato)zinc(II).

7. The compound, oligomer, or polymer of claim 1 wherein PM is a (porphinato)metal compound where the metal is Zn, Mg, Si, Sc, Ti, V, Cr, Fe, Co, Ni, Cu, Zr, Nb, Mo, Ru, Rh, Pd, As, Cd, Ge, Sn, Hf, Ta, W, Re, Os, Lr, Pt, Au, or Pb.

8. The compound, oligomer, or polymer of claim 1 wherein PM is free base (metal free) porphyrin derivative.

9. The compound, oligomer, or polymer of claim 1 wherein PM-Sp is [(10,20-bis[aryl]porphinato)metal-5-ylethynyl, [(10,20-bis[alkyl]porphinato)(metal)-5-ylethynyl, or [(10,20-bis[alkoxy]porphinato)metal-5-ylethynyl where the metal is Zn, Mg, Si, Sc, Ti, V, Cr, Fe, Co, Ni, Cu, Zr, Nb, Mo, Ru, Rh, Pd, As, Cd, Ge, Sn, Hf, Ta, W, Re, Os, Ir, Pt, Au, or Pb.

10. The compound, oligomer, or polymer of claim 9 wherein PM is free base (metal free) porphyrin derivative.

11. A compound, oligomer, or polymer that contains: PQ-(Sp-PQ)$_n$, PQ-(Sp-PQ-Sp'-PQ')$_n$, PQ-(Sp'-PQ'-Sp-PQ)$_n$, PQ-(Sp-PQ-X)$_n$, X-Sp-PQ-(Sp-PQ-X)$_n$, PQ-(Sp-PQ-Sp, —PQ'-X)$_n$, X-Sp-PQ-(Sp-PQ-Sp, —PQ'-X)$_n$, X-Sp*-PQ'-(Sp-PQ-Sp'-PQ'-X)$_n$, PQXSp'-PQ'-Sp-PQ-X)$_n$, X-Sp'-PQ'-(Sp'-PQ'-Sp-PQ-X)$_n$, X-Sp-PQ-(Sp'-PQ'-Sp-PQ-X)$_n$, or X-(Sp-PQ-X-Sp'-PQ'-X)$_n$
wherein:
n is an integer greater than or equal to 1;
Sp is ethynyl;
PQ is

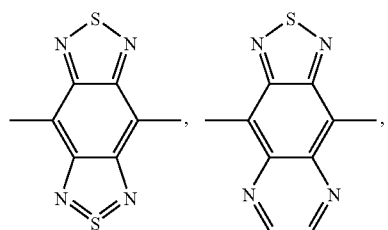

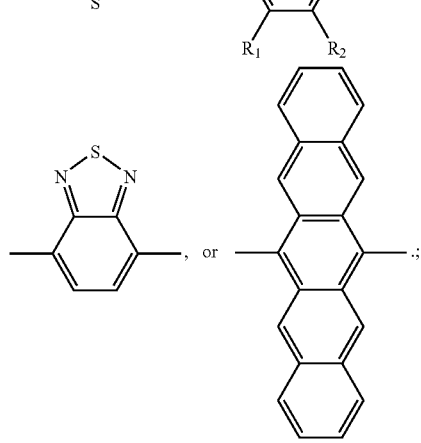

where "-" indicates points of attachment;
$R_1$ and $R_2$ are H, $C_1$-$C_{12}$ alkyl, alkoxy, aryl, or glycol;
Sp' is ethenyl, ethynyl,

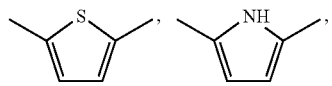

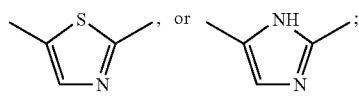

PQ' is

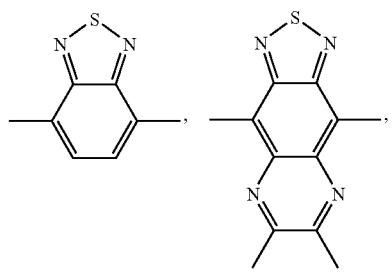

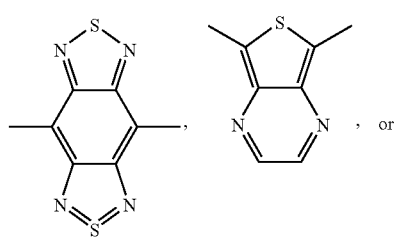

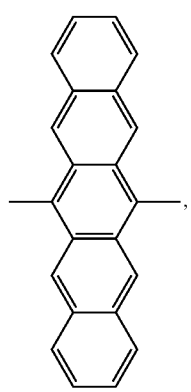

where "-" indicates points of attachment; and
X is a conjugated structure;
wherein at least one of PQ is

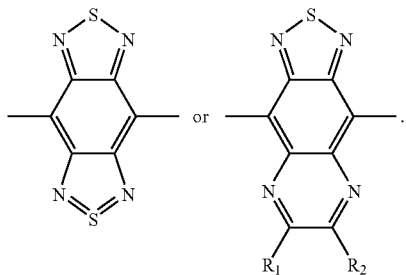

12. The compound, oligomer, or polymer of claim 11 wherein X is:
a porphycene, porphyrin, rubyrin, rosarin, hexaphyrin, sapphyrin, chlorophyl, chlorin, phthalocyanine, porphyrazine, bacteriochlorophyl, pheophytin, or a texaphyrin macrocyclic-based component, or a structure based on one of the corresponding metalated derivatives of these species,
or a fluorophore, lumophore, or phosphore,
or is the residue of p-terphenyl, sulforhodamine B, p-quaterphenyl, rhodamine 101, curbostyryl 124, cresyl violet perchlorate, popop, DODC iodide, coumarin 120, sulforhodamine 101, coumarin 2, oxozine 4 perchlorate, coumarin 339, PCM, coumarin 1, oxazine 170 perchlorate, coumarin 138, nile blue A perchlorate, coumarin 106, oxatine 1 perchlorate, coumarin 102, pyridine 1, coumarin 314T, styryl 7, coumarin 338, HJDC iodide, coumarin 151, PTPC iodide, coumarin 4, cryptocyanine, coumarin 314, DOTC iodide, coumarin 30, HITC iodide, coumarin 500, HITC perchlorate, coumarin 307, PTTC iodide, coumarin 334, DTTC perchlorate, coumarin 7, IR-144, coumarin 343, HDITC perchlorate, coumarin 337, IR-NO, coumarin 6, IR132, coumarin 152, IR-125, coumarin 153, boron-dipyrromethere, HPTS, flourescein, rhodamine 110, 2,7-dichlorofluorescein, rhodamine 65, rhodamin 19 perchlorate, or rhodamine b,
or ethynyl, ethenyl, allenyl, naphthyl, butadiynyl, polyvinyl, thiophenyl, furanyl, pyrrolyl, p-diethylylarenyl, pyridinyl, pyrenyl, anthracenyl, phenanthracenyl, pentacenyl, anilinyl, a conjugated heterocycle, or any conjugated heterocycle that bears diethynyl, di(polyynynyl), divinyl, di(polyvinyl), di(thiophenyl), or dipyrrolyl,
or aryl having about 3-20 carbon atoms, heteroaryl having about 4 to about 20 carbon atoms, alkenyl or heteroalkenyl having from 2 to about 20 carbon atoms, alkynyl or heteroalkynyl having from 2 to about 20 carbon atoms.

13. The compound, oligomer, or polymer of claim 12 that contains PQ-(Sp-PQ)$_n$.

14. The compound, oligomer, or polymer of claim 11 that contains PQ-(Sp-PQ-Sp'-PQ')$_n$ or PQ-(Sp'-PQ'-Sp-PQ)$_n$.

15. The compound, oligomer, or polymer of claim 11 that contains PQ-(Sp-PQ-X)$_n$ or X-Sp-PQ-(Sp-PQ-X)$_n$.

16. The compound, oligomer, or polymer of claim 11 that contains PQ-(Sp-PQ-Sp'-PQ-X)$_n$, X-Sp-PQ-(Sp-PQ-Sp'-PQ'-X)$_n$, X-Sp'-PQ'-(Sp-PQ-Sp'-PQ'-X)$_n$, PQ'-(Sp'-PQ'-Sp-PQ-X)$_n$, X-Sp'-PQ'-(Sp'-PQ'-Sp-PQ-X)$_n$, X-Sp-PQ-(Sp'-PQ'-Sp-PQ-X)$_n$, or X-(Sp-PQ-X-Sp'-PQ'-X)$_n$.

17. The compound, oligomer, or polymer of claim 11 wherein X is a porphyrin.

18. A device comprising a compound, oligomer, or polymer of claim 1.

19. The device of claim 18 that is a light-emitting diode, a photovoltaic cell, a supercapacitor, a field-effect transistor, or a non-linear optical device, or a device in which a compound of claim 13 serves as a 2-photon-absorbing material, a hole transport material, an electron transport material, a photoconductive material, an electrooptic material, a photorefractive material, an imaging agent, an electro-optic modulator, a waveguiding material, a phase-shifting, material, a signal processing material, a frequency doubling material, an optical limiting material, a lasing material, or a nonlinear optical material.

20. A device comprising a compound, oligomer, or polymer of claim 11.

21. The device of claim 20 that is a light-emitting diode, a photovoltaic cell, a supercapacitor, a field-effect transistor, or a non-linear optical device, or a device in which a compound of claim 13 serves as a 2-photon-absorbing material, a hole transport material, an electron transport material, a photoconductive material, an electrooptic material, a photorefractive material, an imaging agent, an electro-optic modulator, a waveguiding material, a phase-shifting, material, a signal processing material, a frequency doubling material, an optical limiting material, a lasing material, or a nonlinear optical material.

22. A composition comprising a polymersome comprising a plurality of amphiphilic copolymers and at least one compound, oligomer, or polymer of claim 1.

23. The composition of claim 22 wherein said amphiphilic copolymer is an amphiphilic block copolymer comprising at least one hydrophilic polymer bonded to at least one hydrophobic polymer.

24. The composition of claim 22 where at least a portion of said polymersome additionally comprises at least one targeting moiety associated with the surface of said polymersome.

25. The composition of claim 22 wherein said polymersome is bioresorbable.

26. A composition comprising a polymersome comprising a plurality of amphiphilic copolymers and at least one compound, oligomer, or polymer of claim 11.

27. The composition of claim 26 wherein said amphiphilic copolymer is an amphiphilic block copolymer comprising at least one hydrophilic polymer bonded to at least one hydrophobic polymer.

28. The composition of claim 26 where at least a portion of said polymersome additionally comprises at least one targeting moiety associated with the surface of said polymersome.

29. The composition of claim 26 wherein said polymersome is bioresorbable.

* * * * *